United States Patent
Shelton, IV et al.

(10) Patent No.: US 11,369,380 B2
(45) Date of Patent: Jun. 28, 2022

(54) METHOD OF APPLYING A BUTTRESS TO A SURGICAL STAPLER

(71) Applicant: Ethicon LLC, Guaynabo, PR (US)

(72) Inventors: Frederick E. Shelton, IV, Hillsboro, OH (US); Rao S. Bezwada, Whitehouse Station, NJ (US); Jason L. Harris, Lebanon, OH (US); Prudence A. Turner, Independence, KY (US); Mark S. Zeiner, Mason, OH (US); Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 108 days.

(21) Appl. No.: 16/401,234

(22) Filed: May 2, 2019

(65) Prior Publication Data

US 2019/0314020 A1 Oct. 17, 2019

Related U.S. Application Data

(63) Continuation of application No. 14/667,842, filed on Mar. 25, 2015, now Pat. No. 10,349,939.

(51) Int. Cl.
*A61B 17/10* (2006.01)
*A61B 17/072* (2006.01)
(Continued)

(52) U.S. Cl.
CPC .......... *A61B 17/105* (2013.01); *A61B 17/068* (2013.01); *A61B 17/07207* (2013.01);
(Continued)

(58) Field of Classification Search
CPC .......... A61B 2017/00951; A61B 2017/00004; A61B 17/07292; A61B 17/07207; A61B 17/068; A61B 17/105
(Continued)

(56) References Cited

U.S. PATENT DOCUMENTS 2,642,375 A 6/1953 Henderson et al.
4,805,823 A 2/1989 Rothfuss
(Continued)

FOREIGN PATENT DOCUMENTS

CN 1799650 A 7/2006
CN 101018572 A 8/2007
(Continued)

OTHER PUBLICATIONS

Chinese Office Action dated Oct. 12, 2019 for Application No. 201680030404.2, 12 pages.
(Continued)

*Primary Examiner* — Robert F Long
*Assistant Examiner* — Xavier A Madison
(74) *Attorney, Agent, or Firm* — Frost Brown Todd LLC

(57) ABSTRACT

A method of applying a buttress to a surgical stapler end effector comprises positioning a buttress assembly between an anvil and a staple cartridge of the end effector. The buttress assembly comprises a buttress body and an adhesive material. The adhesive material faces either an underside of the anvil or a deck of the staple cartridge. The anvil is in an open position relative to the staple cartridge during the act of positioning the buttress assembly between the anvil and the staple cartridge. The method further comprises moving the anvil toward the staple cartridge then moving the anvil back to the open position. The buttress assembly is adhered to the underside of the anvil or the deck of the staple cartridge via the adhesive material with the anvil moved back to the open position. The adhesive material comprises a bioabsorbable polymer.

19 Claims, 60 Drawing Sheets

(51) Int. Cl.
*A61B 17/068* (2006.01)
*A61B 17/00* (2006.01)

(52) U.S. Cl.
CPC .............. *A61B 17/07292* (2013.01); *A61B 2017/00004* (2013.01); *A61B 2017/00951* (2013.01)

(58) Field of Classification Search
USPC .......................................... 227/175.1–182.1
See application file for complete search history.

(56) References Cited

U.S. PATENT DOCUMENTS

| | | | |
|---|---|---|---|
| 5,415,334 A | 5/1995 | Williamson et al. | |
| 5,465,895 A | 11/1995 | Knodel et al. | |
| 5,597,107 A | 1/1997 | Knodel et al. | |
| 5,599,852 A | 2/1997 | Scopelianos et al. | |
| 5,632,432 A | 5/1997 | Schulze et al. | |
| 5,673,840 A | 10/1997 | Schulze et al. | |
| 5,686,090 A | 11/1997 | Schilder et al. | |
| 5,704,534 A | 1/1998 | Huitema et al. | |
| 5,752,965 A | 5/1998 | Francis et al. | |
| 5,792,135 A | 8/1998 | Madhani et al. | |
| 5,814,055 A | 9/1998 | Knodel et al. | |
| 5,817,084 A | 10/1998 | Jensen | |
| 5,824,333 A | 10/1998 | Scopelianoss et al. | |
| 5,878,193 A | 3/1999 | Wang et al. | |
| 5,978,921 A | 11/1999 | Ryu | |
| 6,231,565 B1 | 5/2001 | Tovey et al. | |
| 6,355,699 B1 | 3/2002 | Vyakarnam et al. | |
| 6,364,888 B1 | 4/2002 | Niemeyer et al. | |
| 6,503,257 B2* | 1/2003 | Grant .............. | A61B 17/07207 606/151 |
| 6,783,524 B2 | 8/2004 | Anderson et al. | |
| 6,978,921 B2 | 12/2005 | Shelton, IV et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 7,950,561 B2 | 5/2011 | Aranyi | |
| 8,141,762 B2 | 3/2012 | Bedi et al. | |
| 8,210,411 B2 | 7/2012 | Yates et al. | |
| 8,308,041 B2 | 11/2012 | Kostrzewski | |
| 8,371,491 B2 | 2/2013 | Huitema et al. | |
| 8,408,439 B2 | 4/2013 | Huang et al. | |
| 8,453,904 B2 | 6/2013 | Eskaros et al. | |
| 8,453,914 B2 | 6/2013 | Laurent et al. | |
| 8,479,969 B2 | 7/2013 | Shelton | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm et al. | |
| 8,783,541 B2 | 7/2014 | Shelton et al. | |
| 8,800,838 B2 | 8/2014 | Shelton | |
| 8,814,025 B2* | 8/2014 | Miller .............. | A61B 17/00491 227/180.1 |
| 8,820,605 B2 | 9/2014 | Shelton | |
| 8,844,789 B2 | 9/2014 | Shelton et al. | |
| 8,899,464 B2 | 12/2014 | Hueil et al. | |
| 8,998,060 B2 | 4/2015 | Bruewer et al. | |
| 9,005,243 B2* | 4/2015 | Stopek .................. | B29C 39/123 606/215 |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,211,120 B2 | 12/2015 | Scheib et al. | |
| 9,301,759 B2 | 4/2016 | Spivey et al. | |
| 9,386,984 B2 | 7/2016 | Aronhalt et al. | |
| 9,393,018 B2 | 7/2016 | Wang et al. | |
| 9,398,911 B2 | 7/2016 | Auld | |
| 9,999,408 B2* | 6/2018 | Boudreaux ...... | A61B 17/00491 |
| 10,349,939 B2 | 7/2019 | Shelton et al. | |
| 2005/0070929 A1 | 3/2005 | Dalessandro et al. | |
| 2008/0169328 A1 | 7/2008 | Shelton | |
| 2009/0001122 A1* | 1/2009 | Prommersberger .... | B29C 39/22 227/176.1 |
| 2009/0206143 A1 | 8/2009 | Huitema et al. | |
| 2012/0241492 A1* | 9/2012 | Shelton, IV ....... | A61B 17/0643 227/175.1 |
| 2012/0241493 A1 | 9/2012 | Baxter et al. | |
| 2013/0037596 A1 | 2/2013 | Bear et al. | |
| 2013/0062391 A1 | 3/2013 | Boudreaux et al. | |
| 2013/0068816 A1 | 3/2013 | Vasudevan et al. | |
| 2013/0068820 A1* | 3/2013 | Miller .............. | A61B 17/07207 227/180.1 |
| 2013/0075447 A1 | 3/2013 | Weisenburgh et al. | |
| 2013/0153635 A1* | 6/2013 | Hodgkinson .... | A61B 17/07207 227/176.1 |
| 2013/0206813 A1 | 8/2013 | Nalagatla | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239042 A1 | 8/2014 | Simms et al. | |
| 2014/0239043 A1 | 8/2014 | Simms et al. | |
| 2014/0239044 A1 | 8/2014 | Hoffman | |
| 2014/0263563 A1 | 9/2014 | Stokes et al. | |
| 2015/0136831 A1* | 5/2015 | Baxter, III ......... | A61B 17/0644 227/176.1 |
| 2015/0272575 A1 | 10/2015 | Leimbach et al. | |
| 2015/0351754 A1 | 12/2015 | Harris et al. | |
| 2015/0351763 A1 | 12/2015 | Shelton et al. | |
| 2015/0374360 A1 | 12/2015 | Scheib et al. | |
| 2015/0374373 A1 | 12/2015 | Rector et al. | |
| 2016/0089146 A1 | 3/2016 | Harris et al. | |
| 2016/0278774 A1* | 9/2016 | Shelton, IV ......... | A61B 17/105 |
| 2021/0196277 A1 | 7/2021 | Shelton, IV et al. | |
| 2021/0204947 A1 | 7/2021 | Shelton, IV et al. | |

FOREIGN PATENT DOCUMENTS

| | | |
|---|---|---|
| CN | 102459408 A | 5/2012 |
| EP | 1256317 | 11/2002 |
| EP | 1520525 | 4/2005 |
| EP | 1256317 B1 | 12/2006 |
| EP | 1520525 B1 | 3/2010 |
| EP | 2604196 | 6/2013 |
| EP | 2698118 | 2/2014 |
| JP | 2831439 B | 12/1998 |
| JP | 2003-524435 A | 8/2003 |
| JP | 2005-519654 A | 7/2005 |
| JP | 2007-533796 | 11/2007 |
| JP | 2014-121599 | 7/2014 |
| JP | 2015-516838 A | 6/2015 |
| WO | WO 91/09079 | 6/1991 |

OTHER PUBLICATIONS

European Communication dated Nov. 16, 2018 for Application No. 16162067.9, 5 pages.
Japanese Notification of Reasons for Refusal dated Dec. 13, 2019 for Application No. 2017-549692, 9 pages.
Webster, et al., "PEGylated Proteins: Evaluation of Their Safety in the absence of Definitive Metabolism Studies," Drug Metabolism and Disposition, 2007, 35(1):9-16.
International Search Report and Written Opinion dated Oct. 12, 2016 re Application No. PCT/US2016/023061.
Partial European Search Report dated Jul. 26, 2016 for Application No. 16162067.9.
European Search Report, Extended, and Written Opinion dated Oct. 31, 2016 for Application No. 16162067.9, 10 pages.

(56) References Cited

OTHER PUBLICATIONS

U.S. Appl. No. 17/130,927.
U.S. Appl. No. 17/130,929.
Brazilian Search Report dated Apr. 24, 2020 for Application No. BR 112017020354-5, 4 pgs.
Chinese Office Action, Notification of Second Office Action, and Search Report, dated Jun. 23, 2020 for Application No. CN 201680030404.2, 10 pgs.
European Search Report, Partial, and Provisional Written Opinion dated Sep. 14, 2020 for Application No. EP 20167229.2, 17 pgs.
European Search Report, Extended, and Written Opinion dated Dec. 17, 2020 for Application No. EP 20167229.2, 15 pgs.
Indian Search Report dated Oct. 23, 2020 for Application No. IN 201717032833, 6 pgs.
Japanese Office Action, Notification of Reasons for Refusal, Final, dated Jun. 16, 2020 for Application No. JP 2017-549692, 8 ps.

* cited by examiner

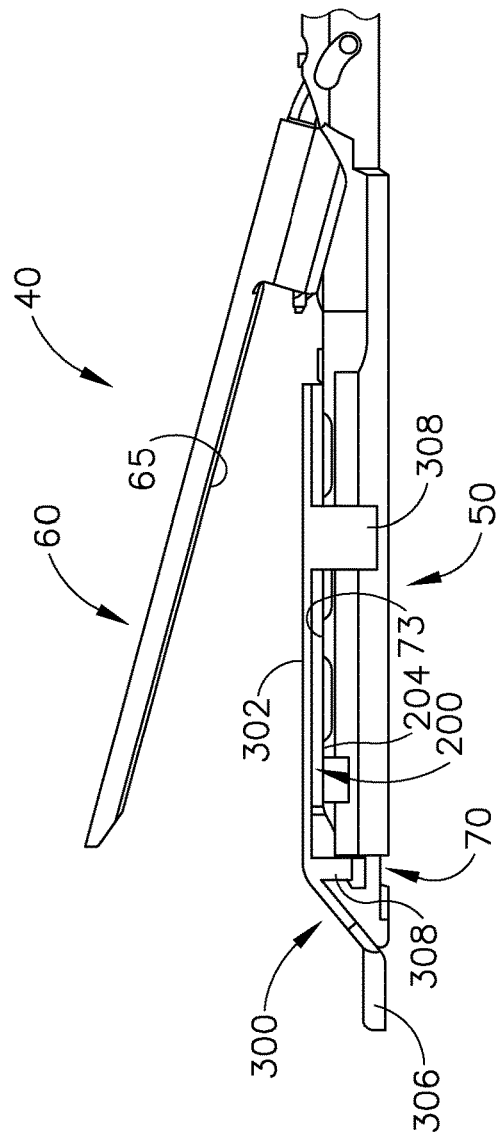
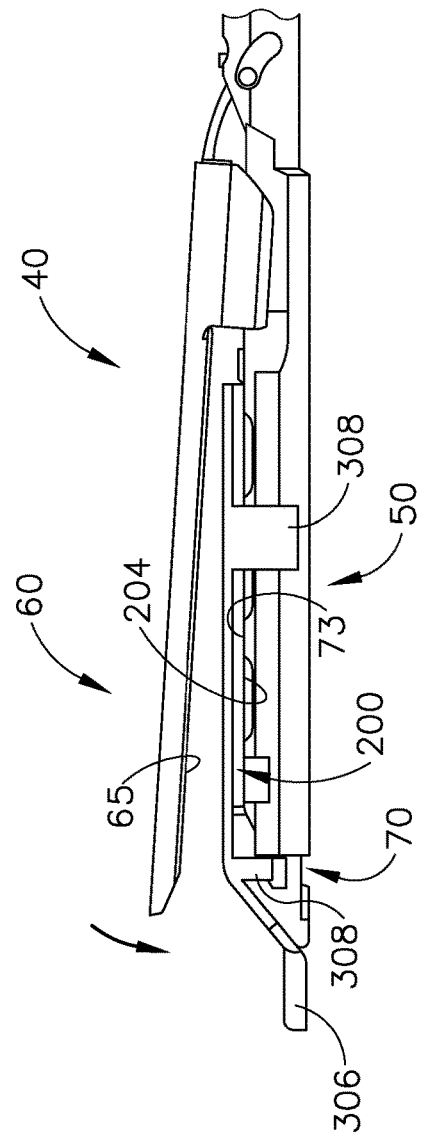

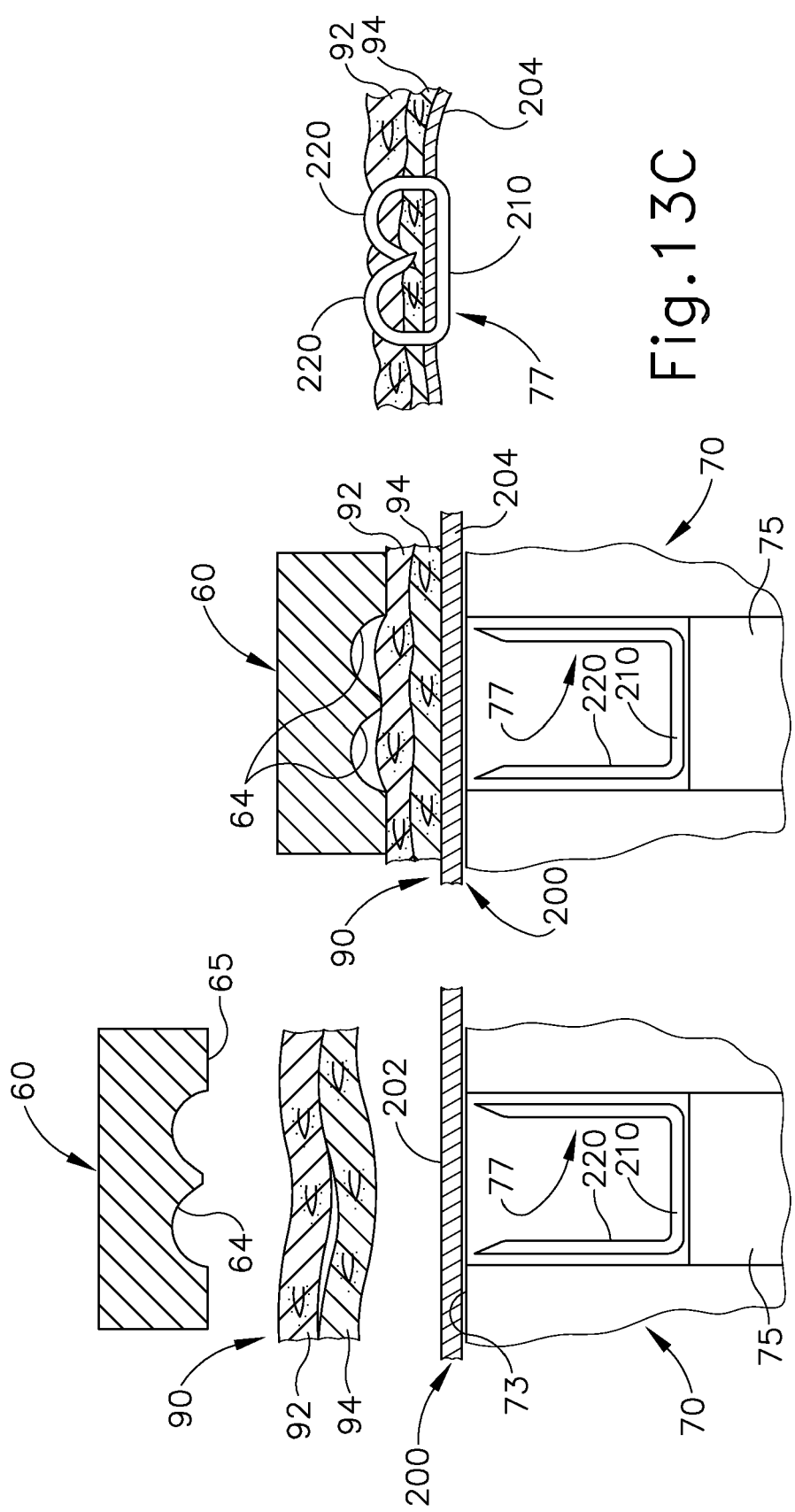

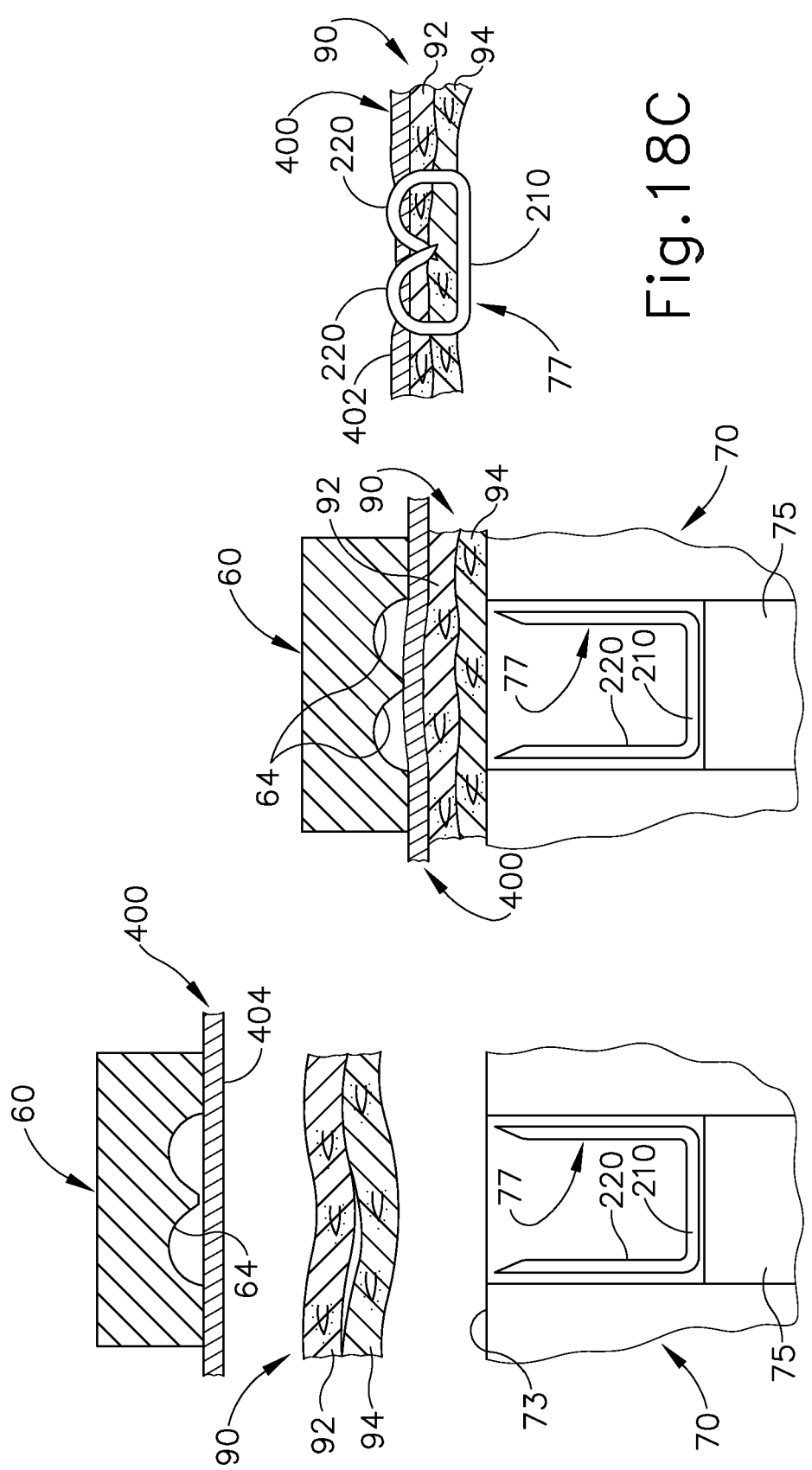

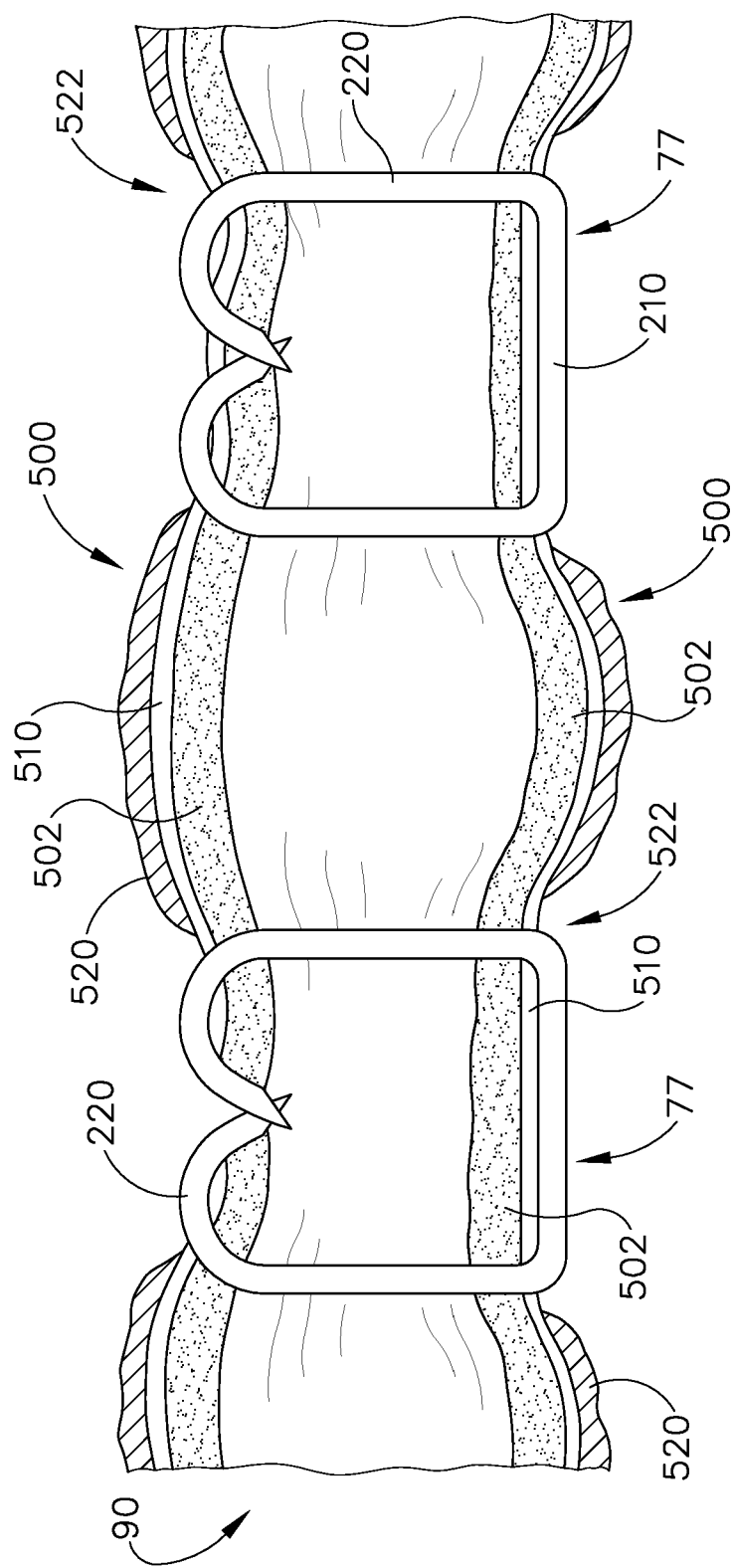

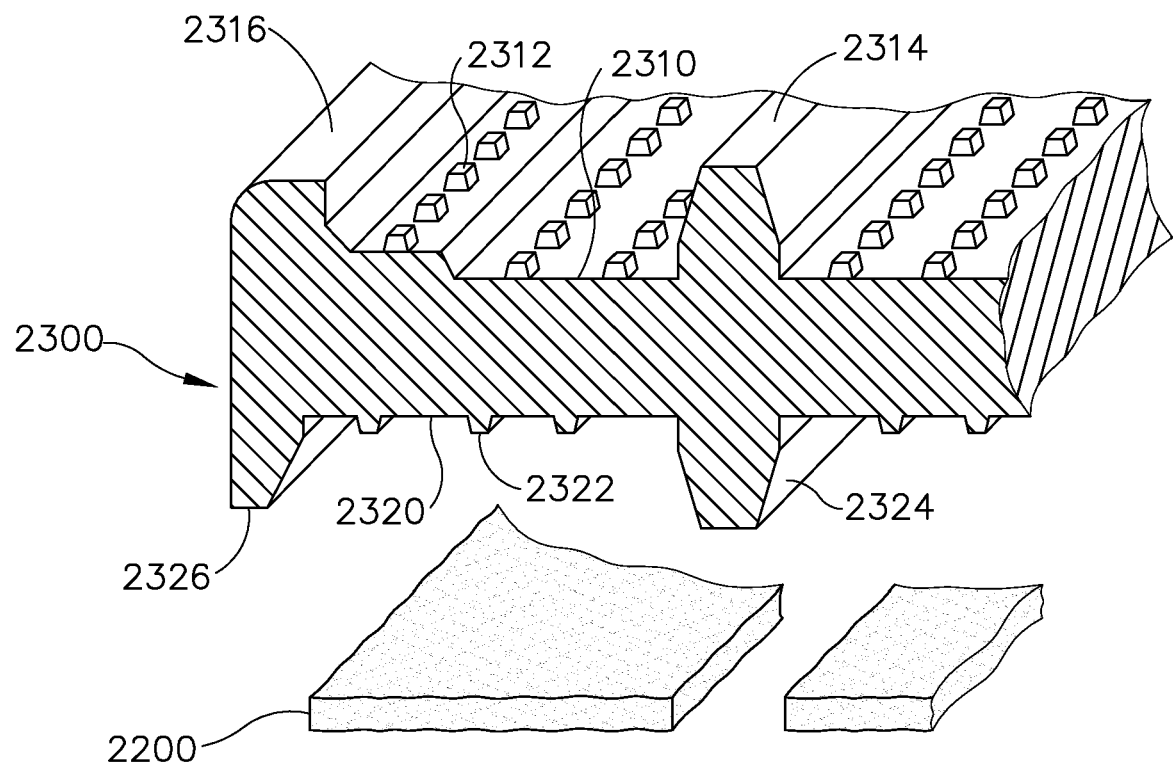
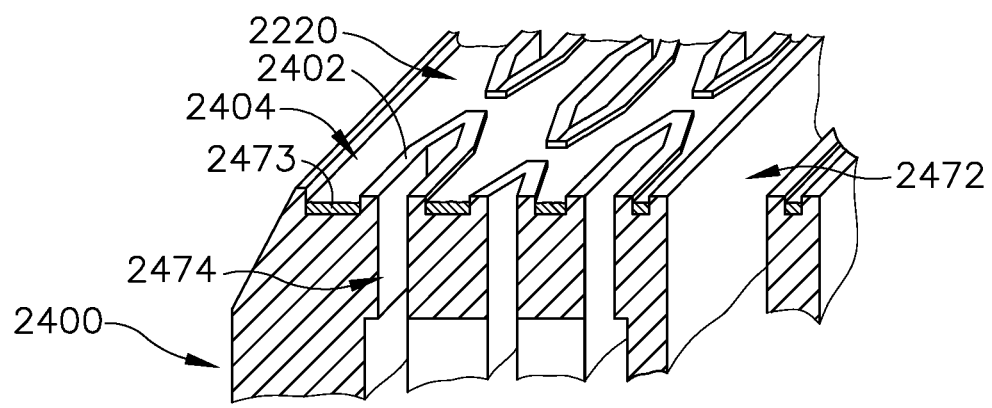
Fig.38

METHOD OF APPLYING A BUTTRESS TO A SURGICAL STAPLER

This application is a continuation of U.S. patent application Ser. No. 14/667,842, filed Mar. 25, 2015 and published as U.S. Pat. Pub. No. 2016/0278774 on Sep. 29, 2016, issued as U.S. Pat. No. 10,349,939 on Jul. 16, 2019.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2107; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2017; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 17, 2017. The disclosure of each of the above-cited U.S. Patent Publications is incorporated by reference herein.

Additional surgical stapling instruments are disclosed in U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No.

2014/0263563, entitled "Method and Apparatus for Sealing End-to-End Anastomosis" published Sep. 18, 2014, issued as U.S. Pat. No. 9,597,082 on Mar. 21, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue", issued as U.S. Pat. No. 9,936,954 on Apr. 10, 2018; and U.S. patent application Ser. No. 14/498,070, entitled "Radically Expandable Staple Line" filed Sep. 26, 2014, published as U.S. Pub. No. 2016/0089146 on Mar. 31, 2016, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 12B depicts a side elevational view of the buttress and retainer of FIG. 10 engaging the end effector of FIG. 3, with the anvil of the end effector in an open position;

FIG. 12C depicts a side elevational view of the buttress and retainer of FIG. 10 engaging the end effector of FIG. 3, with the anvil of the end effector moving toward a closed position;

FIG. 13A depicts a cross-sectional view of a portion of the end effector and buttress assembly of FIG. 12D, with tissue positioned between the buttress and the anvil, and with the anvil in an open position;

FIG. 13B depicts a cross-sectional view of a portion of the end effector and buttress assembly of FIG. 12D, with tissue positioned between the buttress and the anvil, and with the anvil in a closed position;

FIG. 13C depicts a cross-sectional view of a staple and the buttress of FIG. 12D being secured to tissue by the end effector of FIG. 12D;

FIG. 18A depicts a cross-sectional view of a portion of the end effector and buttress assembly of FIG. 17B, with tissue positioned between the buttress and the staple cartridge, and with the anvil in an open position;

FIG. 18B depicts a cross-sectional view of a portion of the end effector and buttress assembly of FIG. 17B, with tissue positioned between the buttress and the staple cartridge, and with the anvil in a closed position;

FIG. 18C depicts a cross-sectional view of a staple and the buttress of FIG. 17B being secured to tissue by the end effector of FIG. 17B;

FIG. 21 depicts a cross-sectional view of staples and a buttress secured to tissue;

FIG. 38 depicts a partial, exploded, perspective cross-sectional view of an exemplary alternative staple cartridge with a buttress and retainer;

Figure 1:
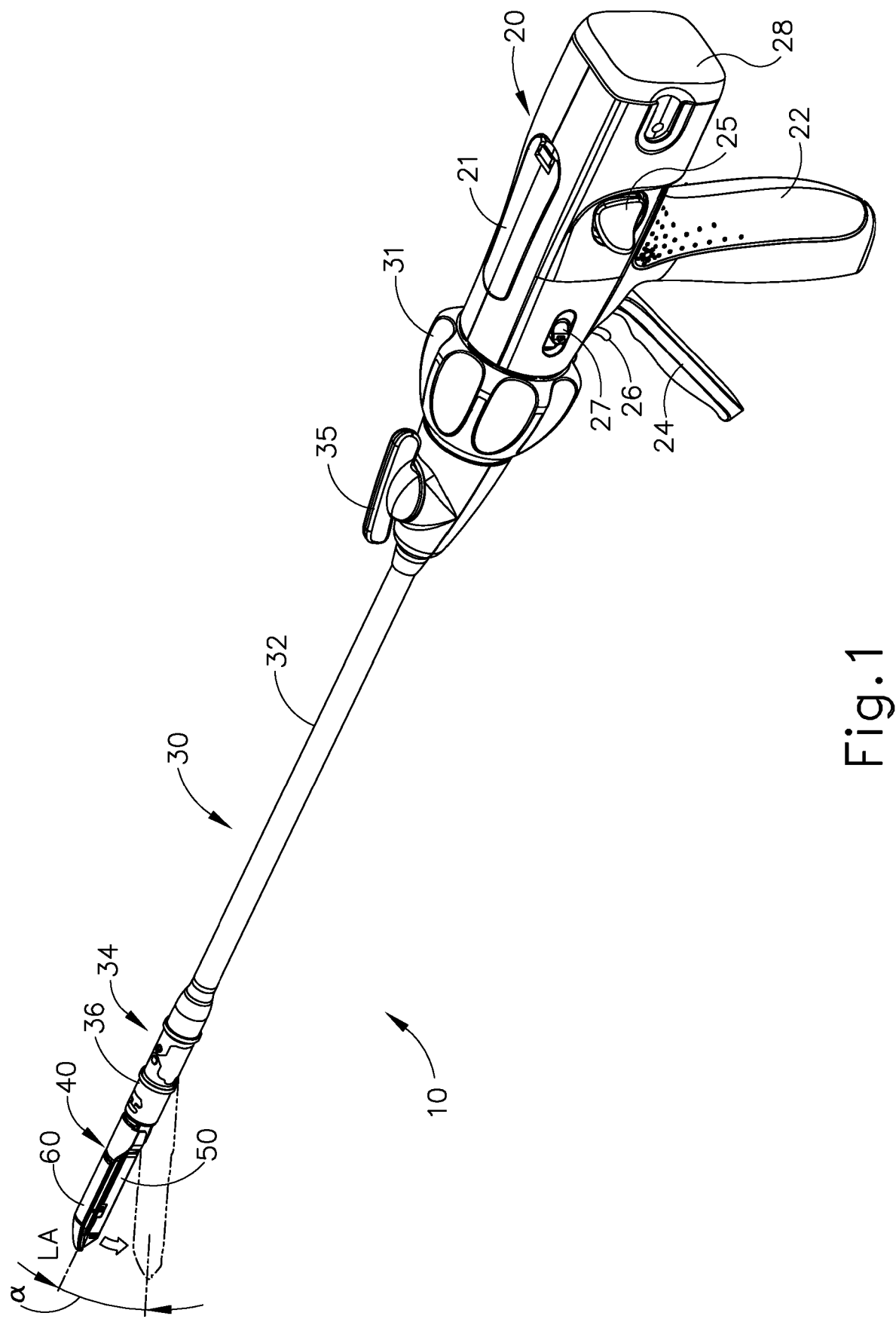
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
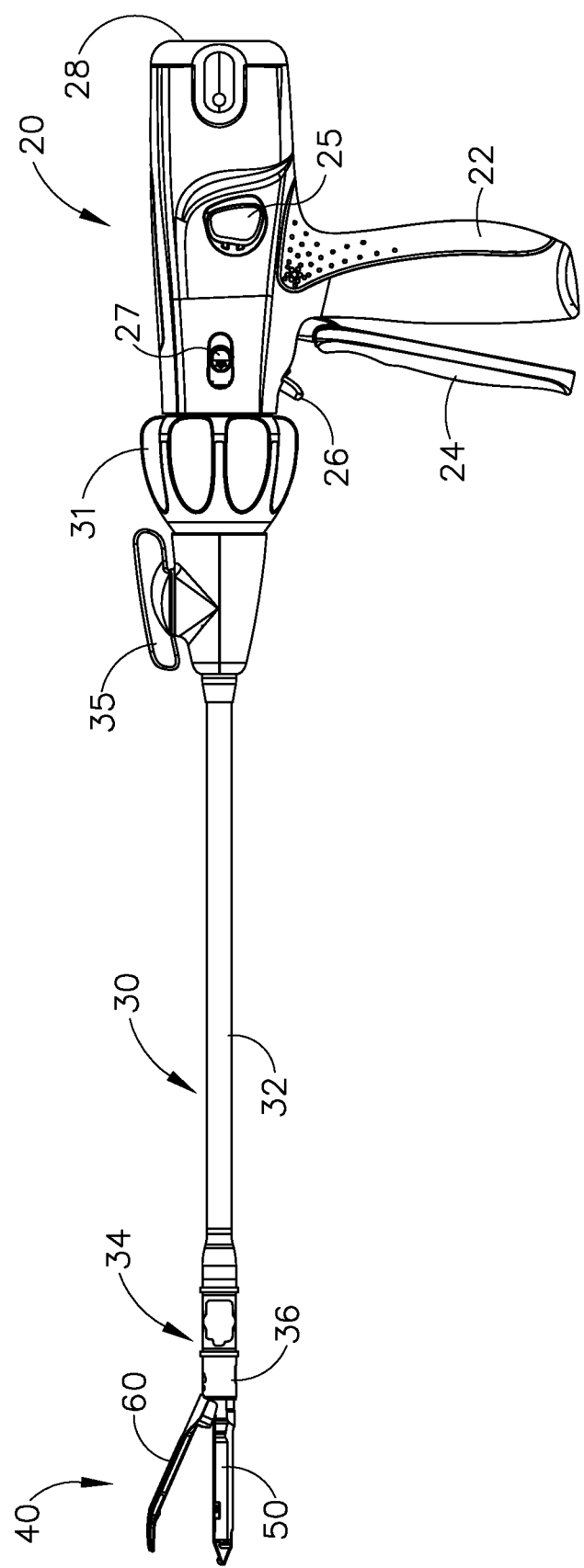
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
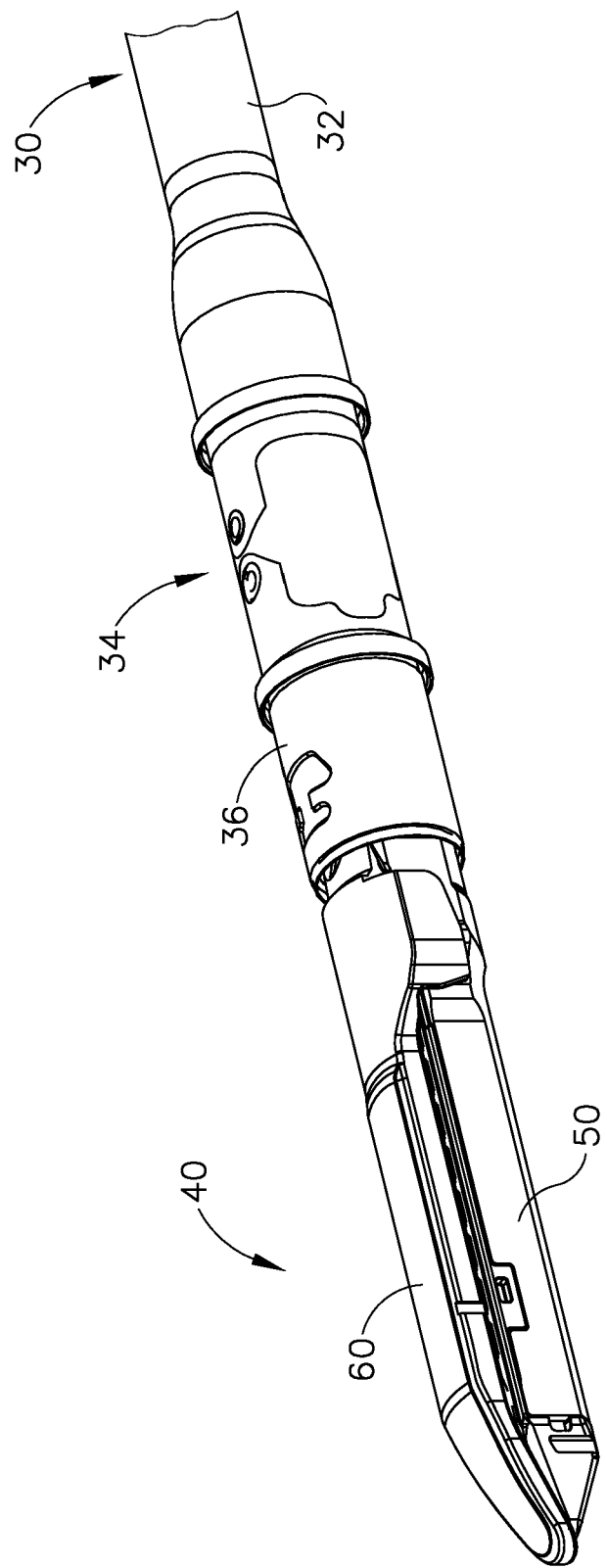
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein. Articulation section (34) may also be constructed and operable in accordance with at least some of the teachings of U.S. patent application Ser. No. 14/314,125, entitled "Articulation Drive Features for Surgical Stapler," filed Jun. 25, 2014, published as U.S. Pub. No. 2015/0374360 on Dec. 31, 2015, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

Figure 4:
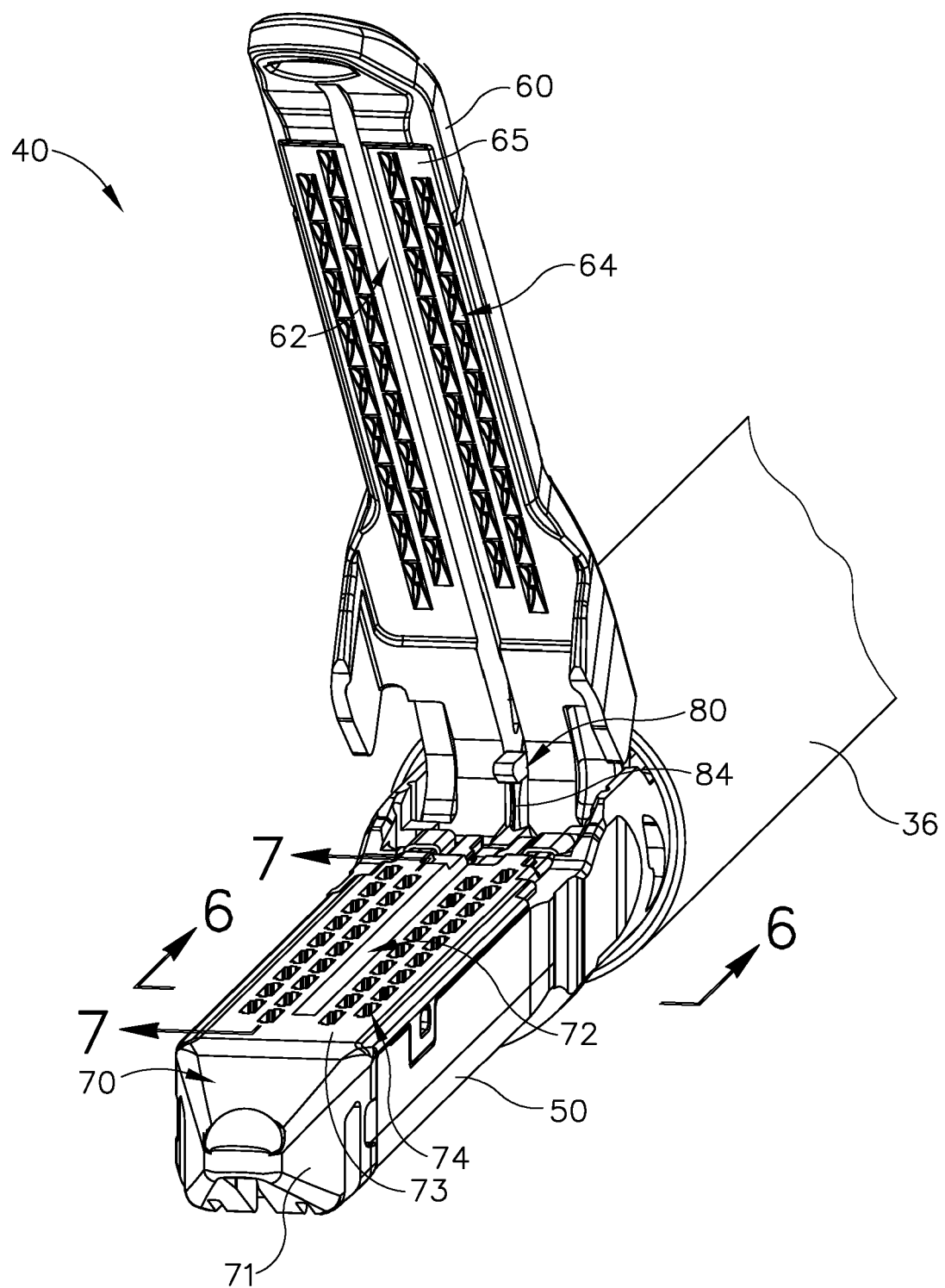
FIG. 4 depicts a perspective view of the end effector of FIG. 3, with the end effector in an open configuration.
Figure 5:
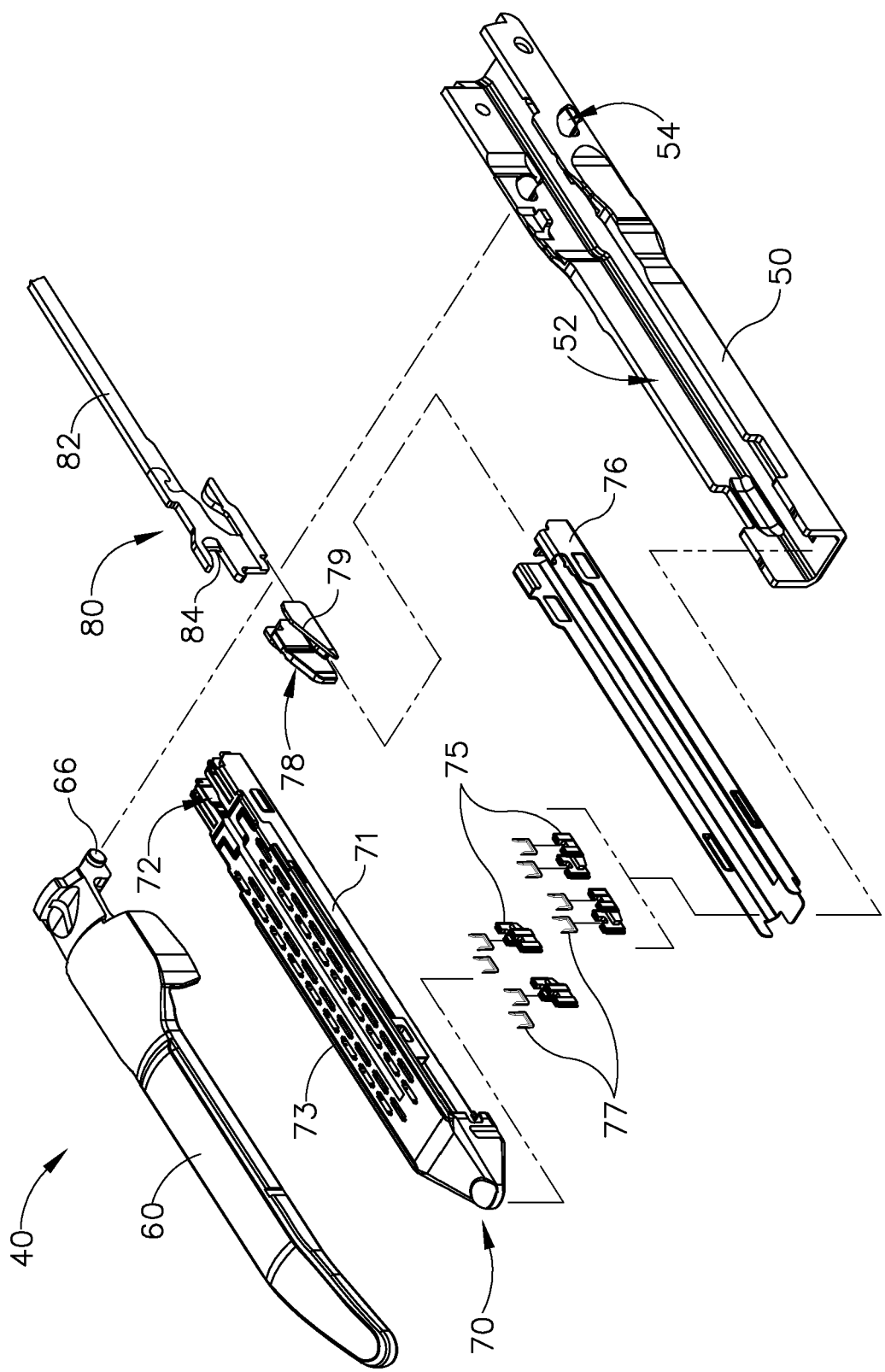
FIG. 5 depicts an exploded perspective view of the end effector of FIG. 3.
Figure 6:
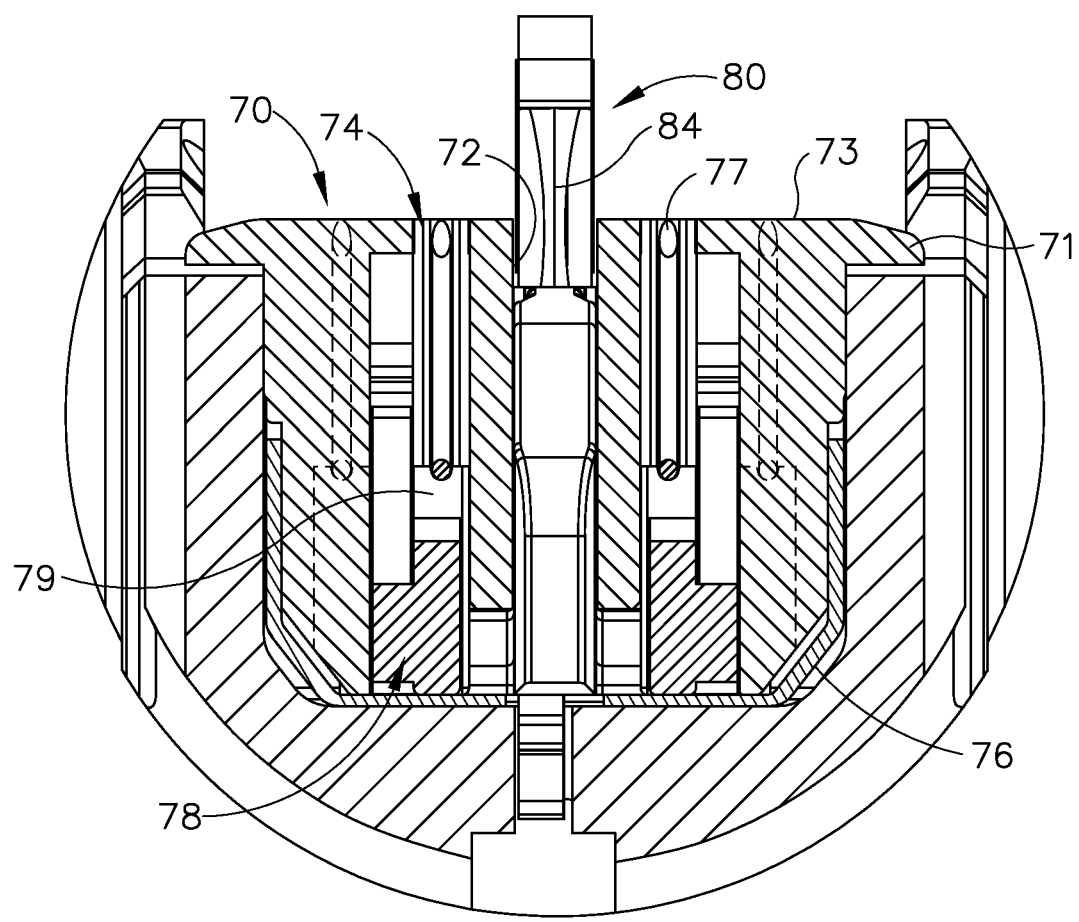
FIG. 6 depicts a cross-sectional end view of the end effector of FIG. 3, taken along line 6-6 of FIG. 4.
Figure 7A:
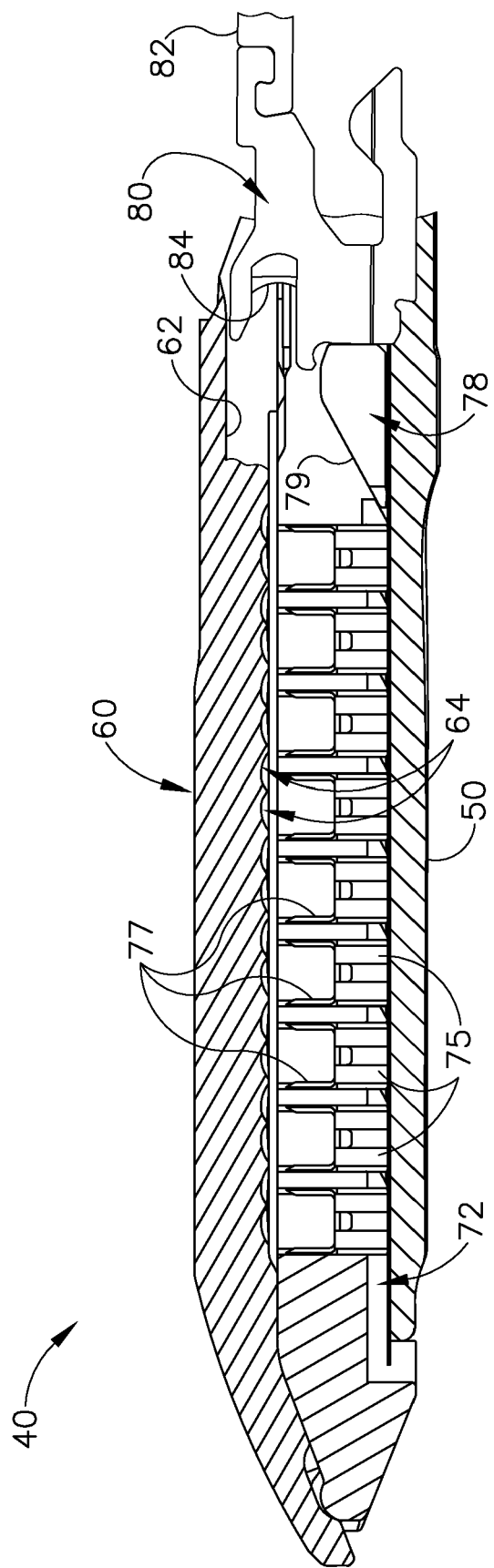
FIG. 7A depicts a cross-sectional side view of the end effector of FIG. 3, taken along line 7-7 of FIG. 4, with a firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64) that are formed in the underside (65) of anvil (60). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U. U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

Figure 7B:
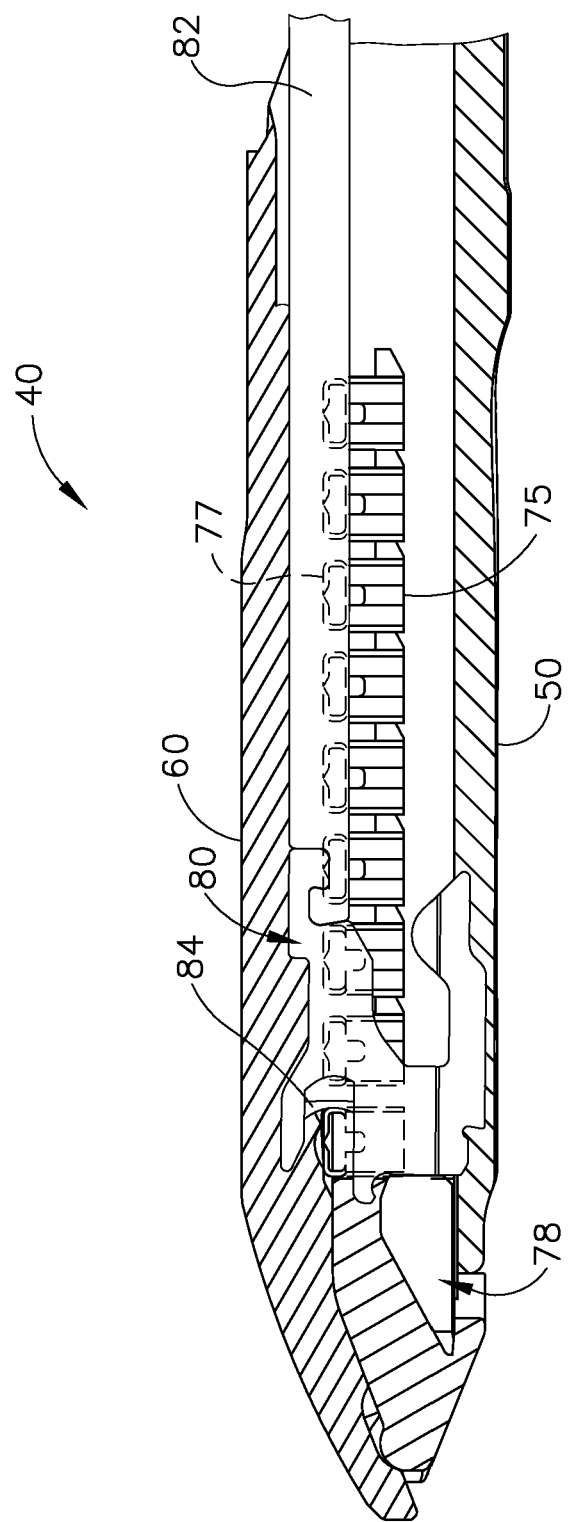
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. Pub. No. 2014/0239041, entitled "Lockout Feature for Movable Cutting Member of Surgical Instrument," published Aug. 28, 2014, issued as U.S. Pat. No. 9,717,497 on Aug. 1, 2017 the disclosure of which is incorporated by reference herein; and/or at least some of the teachings of U.S. patent application Ser. No. 14/314,108, entitled "Method of Using Lockout Features for Surgical Stapler Cartridge," filed on Jun. 25, 2014, published as U.S. Pub. No. 2015/0374373 on Dec. 31, 2015, issued as U.S. Pat. No. 10,335,147 on Jul. 2, 2019, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, published as U.S. Pub. No. 2015/0374373 on Dec. 31, 2015, issued as U.S. Pat. No. 10,335,147 on Jul. 2, 2019, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

In the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). In some such versions, firing beam (82) may only be advanced distally when anvil (60) is in a fully closed position relative to lower jaw (50). After firing beam (82) is advanced distally to sever tissue and drive staples (77) as described above with reference to FIGS. 7A-7B, the drive assembly for firing beam (82) may be automatically reversed to drive firing beam (82) proximally back to the retracted position (e.g., back from the position shown in FIG. 7B to the position shown in FIG. 7A). Alternatively, the operator may actuate firing beam reverse switch (27), which may reverse the drive assembly for firing beam (82) in order to retract firing beam (82) to a proximal position. Handle assembly (20) of the present example further includes a bailout feature (21), which is operable to provide a mechanical bailout allowing the operator to manually retract firing beam (82) proximally (e.g., in the event of power loss while firing beam (82) is in a distal position, etc.).

By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein. As another merely illustrative example, the features that are operable to provide motorized actuation of firing beam (82) may be configured and operable in accordance with at least some of the teachings of U.S. Pat. No. 8,453,914, entitled "Motor-Driven Surgical Cutting Instrument with Electric Actuator Directional Control Assembly," issued Jun. 4, 2013, the disclosure of which is incorporated by reference herein. As yet another merely illustrative example, the features that are operable to provide motorized actuation of firing beam (82) may be configured and operable in accordance with at least some of the teachings of U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

Other suitable components, features, and configurations that may be used to provide motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be manually actuated in accordance with at least some of the teachings of any other reference cited herein.

Figure 8:
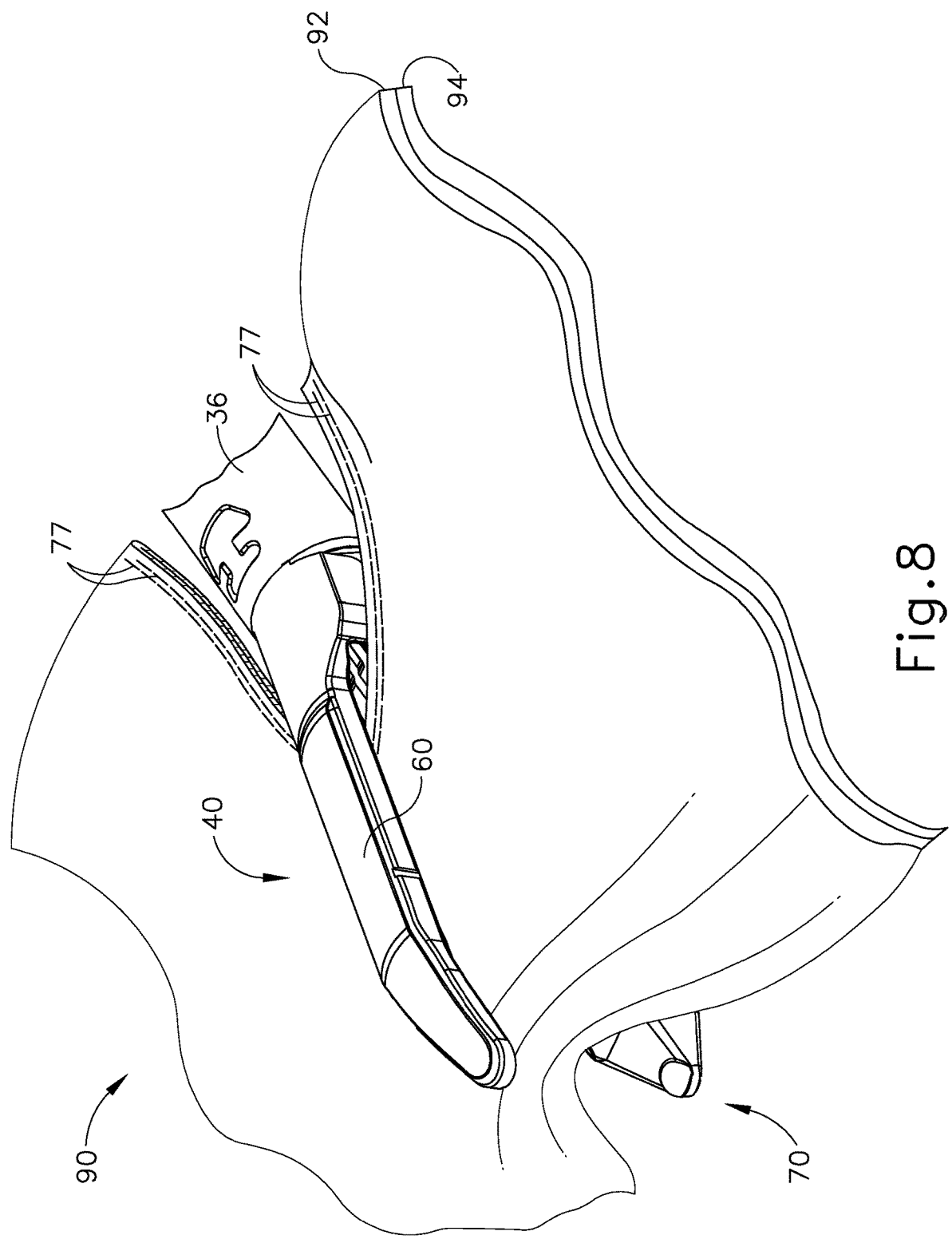
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress for Surgical Stapler

As noted above, it may be desirable in some instances to equip end effector (40) with a buttress material to reinforce the mechanical fastening of tissue (90) provided by staples (77). Such a buttress may prevent the applied staples (77) from pulling through tissue (90) and may otherwise reduce a risk of tissue (90) tearing at or near the site of applied staples (77). In addition to or as an alternative to providing structural support and integrity to a line of staples (77), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress for Surgical Stapler

Figure 9:
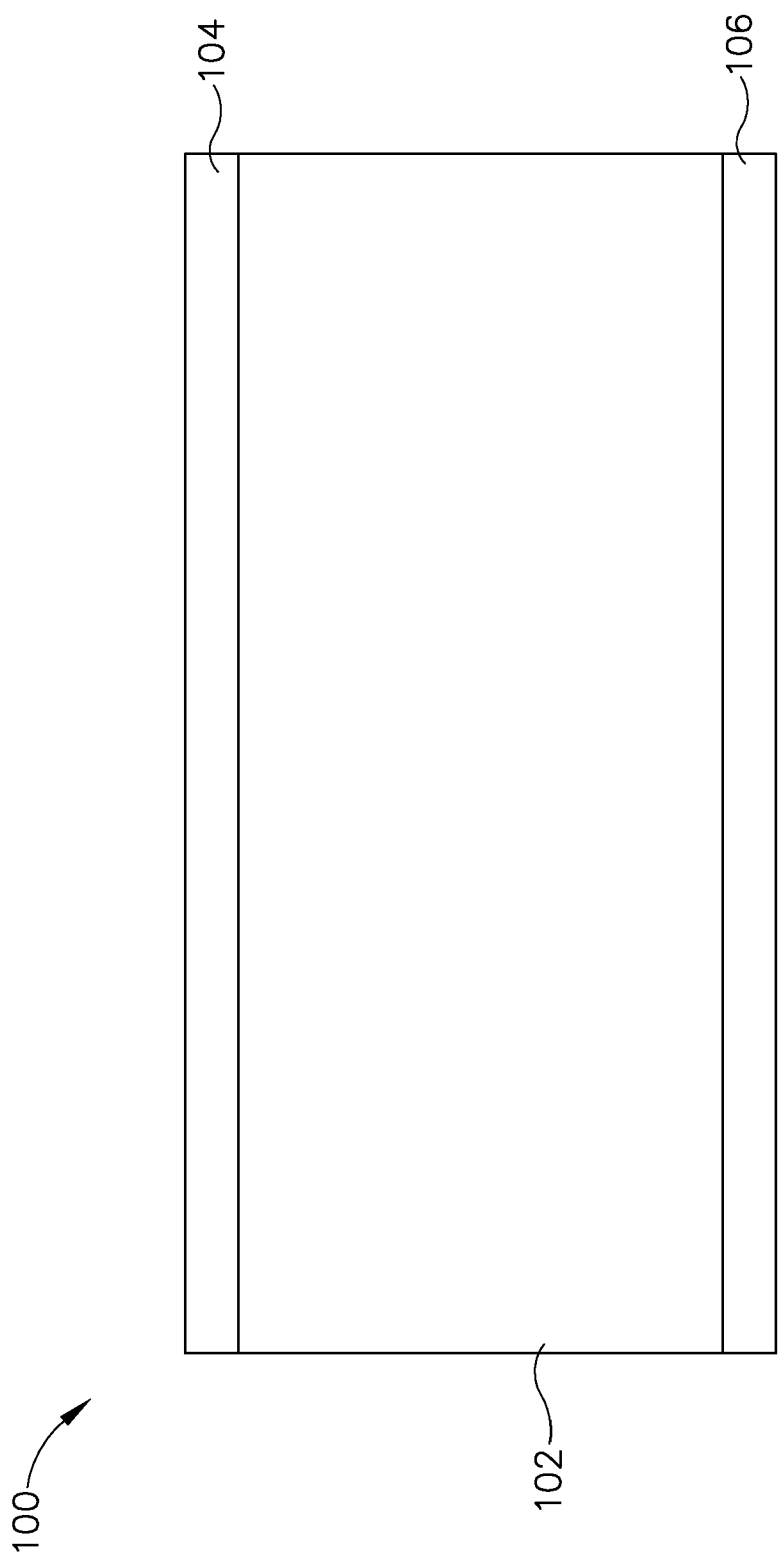
FIG. 9 depicts a cross-sectional view of an exemplary buttress assembly that may be used with the end effector of FIG. 3.
Figure 10:
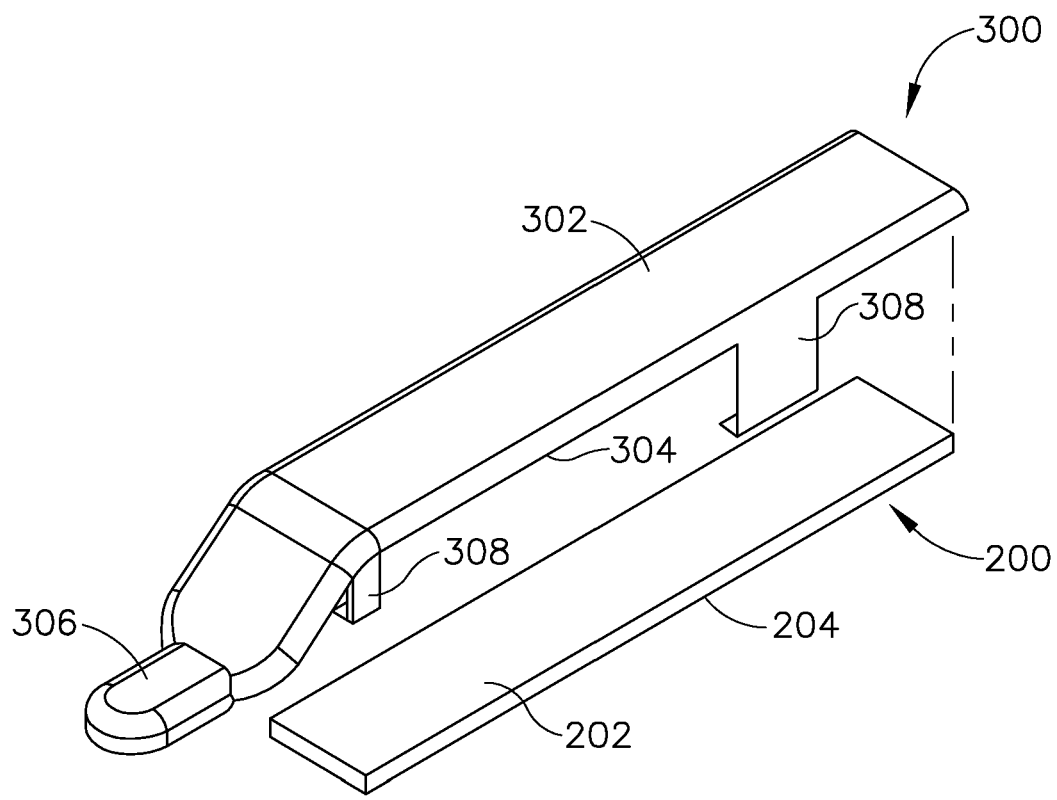
FIG. 10 depicts an exploded perspective view of an exemplary buttress and retainer.
Figure 11:
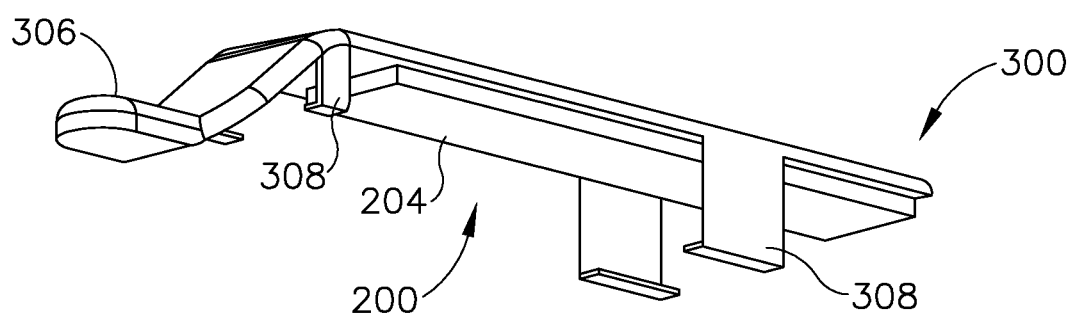
FIG. 11 depicts a perspective view of the buttress and retainer of FIG. 10, with the buttress secured to the underside of the retainer.

FIG. 9 shows an exemplary buttress assembly (100) with a basic composition. Buttress assembly (100) of this example comprises a buttress body (102), an upper adhesive layer (104), and a lower adhesive layer (106). In the present example, buttress body (102) comprises a strong yet flexible material configured to structurally support a line of staples (77). In addition or in the alternative, buttress body (102) may comprise a material including, for example, a hemostatic agent such as fibrin to assist in coagulating blood and reduce bleeding at the severed and/or stapled surgical site along tissue (90).

As another merely illustrative example, buttress body (102) may comprise other adjuncts or hemostatic agents such as thrombin may be used such that buttress body (102) may assist to coagulate blood and reduce the amount of bleeding at the surgical site. The hemostatic abilities of such adjuncts may also contribute to the use of such adjuncts as adhesives and sealants. The agents may assist to coagulate blood at a surgical site, which allows tissue surrounding such blood to stick together and may prevent leaks along the stapled tissue site, for example. Other adjuncts or reagents that may be incorporated into buttress body (102) may further include but are not limited to medical fluid or matrix components. By way of example only, buttress body (102) may include natural or genetically engineered absorbable polymers or synthetic absorbable polymers, or mixtures thereof. Merely illustrative examples of natural or genetically engineered absorbable polymers are proteins, polysaccharides and combinations thereof. Merely illustrative examples of proteins that may be used include prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of synthetic absorbable polymers are aliphatic polyester polymers, copolymers, and/or combinations thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one). Other suitable compounds, materials, substances, etc., that may be used in a medical fluid or matrix will be apparent to those of ordinary skill in the art in view of the teachings herein.

Buttress body (102) may alternatively comprise a fibrous pad, a foam, a mesh, a weave, and/or another structure capable of containing an adhesive and/or other type of medical fluid. In addition or in the alternative, buttress body (102) may simply comprise a mesh, a weave, and/or some other structure that is constructed to provide structural support or integrity to a line of staples (77) applied through tissue (90). Such a material and structure may be relatively thin and in some instances may be substantially non-compressible. By way of further example only, buttress body (102) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018 the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014 the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,383,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; and/or U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein.

In the present example, buttress body (102) comprises a woven mesh of VICRYL® (polyglactin 910) material by Ethicon US, LLC. VICRYL® woven mesh is prepared from a synthetic absorbable copolymer of glycolide and lactide, derived respectively from glycolic and lactic acids. This tightly woven mesh is prepared from uncoated, undyed fiber identical in composition to that used in VICRYL® synthetic absorbable suture, which has been found to be inert, nonantigenic, nonpyrogenic, and to elicit only a mild tissue reaction during absorption. VICRYL® woven mesh is intended for use as a buttress to provide temporary support during the healing process. Alternatively, any other suitable materials or combinations of materials may be used in addition to or as an alternative to VICRYL® material to form buttress body (102).

In versions where buttress body (102) is formed as a mesh, it should be understood that various kinds of mesh geometry may be used. By way of example only, buttress body (102) may be formed as a woven mesh, a knitted mesh, or a warp knitted mesh. Regardless of whether buttress body (102) is formed as a mesh or not, buttress body (102) is porous in some examples. As described in greater detail below, an adhesive layer (104, 106) may be provided on buttress body (102) in order to adhere buttress body (102) to underside (65) of anvil (60) or deck (73) of staple cartridge (70). In some versions where buttress body (102) is porous, the material forming adhesive layer (104, 106) may pass through buttress body (102) to reach the outer surface of buttress body (102) that is opposite to the surface on which adhesive layer (104, 106) is disposed.

By way of example only, upper adhesive layer (104) may be used to secure buttress assembly (100) to the underside (304) of a retainer (300) as will be described in greater detail below; while lower adhesive layer (106) is used to secure buttress assembly (100) to deck (73) of staple cartridge (70). In some versions of this example, lower adhesive layer (106) is configured to provide stronger adherence than upper adhesive layer (104). In some illustrative variations of this example, one or more features of retainer (300) (e.g., flanges, clips, etc.) are configured to selectively retain buttress assembly (100) against underside (304) of retainer (300), such that upper adhesive layer (104) is omitted; while lower adhesive layer (106) is used to secure buttress assembly (100) to deck (73) of staple cartridge (70). In addition or in the alternative, an adhesive material may be applied to the lower surface of a porous version of buttress body (102) to form lower adhesive layer (106), and some of that adhesive material may pass through buttress body (102) to form upper adhesive layer (104). In some such versions, lower adhesive layer (106) ultimately has more adhesive material than upper adhesive layer (104), such that lower adhesive layer (106) provides greater adhesion than upper adhesive layer (104).

In yet another merely illustrative example, lower adhesive layer (106) may be used to secure buttress assembly (100) to the upper side (302) of a retainer (300) as will be described in greater detail below; while upper adhesive layer (104) is used to secure buttress assembly to underside (65) of anvil (60) of end effector (40). In some versions of this example, upper adhesive layer (104) is configured to provide stronger adherence than lower adhesive layer (106). In some illustrative variations of this example, one or more features of retainer (300) (e.g., flanges, clips, etc.) are configured to selectively retain buttress assembly (100) against upper side (302) of retainer (300), such that lower adhesive layer (106) is omitted; while upper adhesive layer (104) is used to secure buttress assembly (100) to underside (65) of anvil (60). In addition or in the alternative, an adhesive material may be applied to the upper surface of a porous version of buttress body (102) to form upper adhesive layer (104), and some of that adhesive material may pass through buttress body (102) to form lower adhesive layer (106). In some such versions, upper adhesive layer (104) ultimately has more adhesive material than lower adhesive layer (106), such that upper adhesive layer (104) provides greater adhesion than lower adhesive layer (106).

Various suitable compositions that may be used to form each adhesive layer (104, 106), as well as various forms that each adhesive layer (104, 106) may take, will be described in greater detail below.

It should also be understood that buttress assembly (100) may include an impermeable layer or a semi impermeable layer interposed between buttress body (102) and adhesive layer (102), to prevent or restrict migration of adhesive material from adhesive layer (104, 106) into buttress body (100). By way of example only, body (102) may be formed of a porous media (e.g., ETHISORB™ by Codman of Raynham, Mass.); while the semi impermeable layer may comprise polydioxanone (PDS). In versions where buttress assembly (100) comprises an impermeable layer or a semi impermeable layer to prevent or restrict migration of adhesive material from adhesive layer (104, 106) into buttress body (100), such a layer may be integrated into buttress body (102) such that the layer permits the adhesive to migrate at least partially into buttress body (102) but not across the full thickness of buttress body (102). Various suitable ways in which an impermeable layer or a semi impermeable layer may be integrated into buttress assembly (100) to prevent or restrict migration of an adhesive material will be apparent to those of ordinary skill in the art in view of the teachings herein.

B. Exemplary Instrument and Technique for Securing Buttress to Deck of Staple Cartridge FIGS. 10-12D show a combination of an exemplary buttress (200) with an exemplary retainer (300). Buttress (200) of this example may be constructed in accordance with the teachings above relating to buttress assembly (100) and/or in accordance with other teachings herein. Buttress (200) includes an upper side (202) and an underside (204). In the present example, underside (204) includes an adhesive (e.g., like lower adhesive layer (106)) to secure buttress (200) to deck (73) of staple cartridge (70) as described in greater detail below.

Retainer (300) of this example comprises an upper side (302), an underside (304), a distally projecting tongue (306), and a set of resilient latches (308). Upper side (302) and underside (304) are each generally flat in the present example, though it should be understood that upper side (302) and/or underside (304) may include various kinds of features as described elsewhere herein. Tongue (306) is configured to provide a grip for an operator, thereby facilitating grasping and handling of retainer (300) during use. Latches (308) are configured to releasably secure retainer (300) to lower jaw (50) of end effector (40) as will be described in greater detail below. By way of example only, retainer (300) may be formed of molded plastic. Alternatively, retainer (300) may be formed using any other suitable material(s) or technique(s).

In the present example, buttress (200) is secured to underside (304) of retainer (300), such that upper side (202) of buttress (200) apposes underside (304) of retainer (300). In some versions, an adhesive such as upper adhesive layer (104) provides releasable adhesion of buttress (200) to underside (304) of retainer (300). In some other versions, retainer (300) includes one or more features (e.g., flanges, clips, etc.) that are configured to selectively retain buttress (200) against underside (304) of retainer (300). Various suitable ways in which buttress (200) may be releasably secured to underside (304) of retainer (300) will be apparent to those of ordinary skill in the art in view of the teachings herein.

Figure 12A:
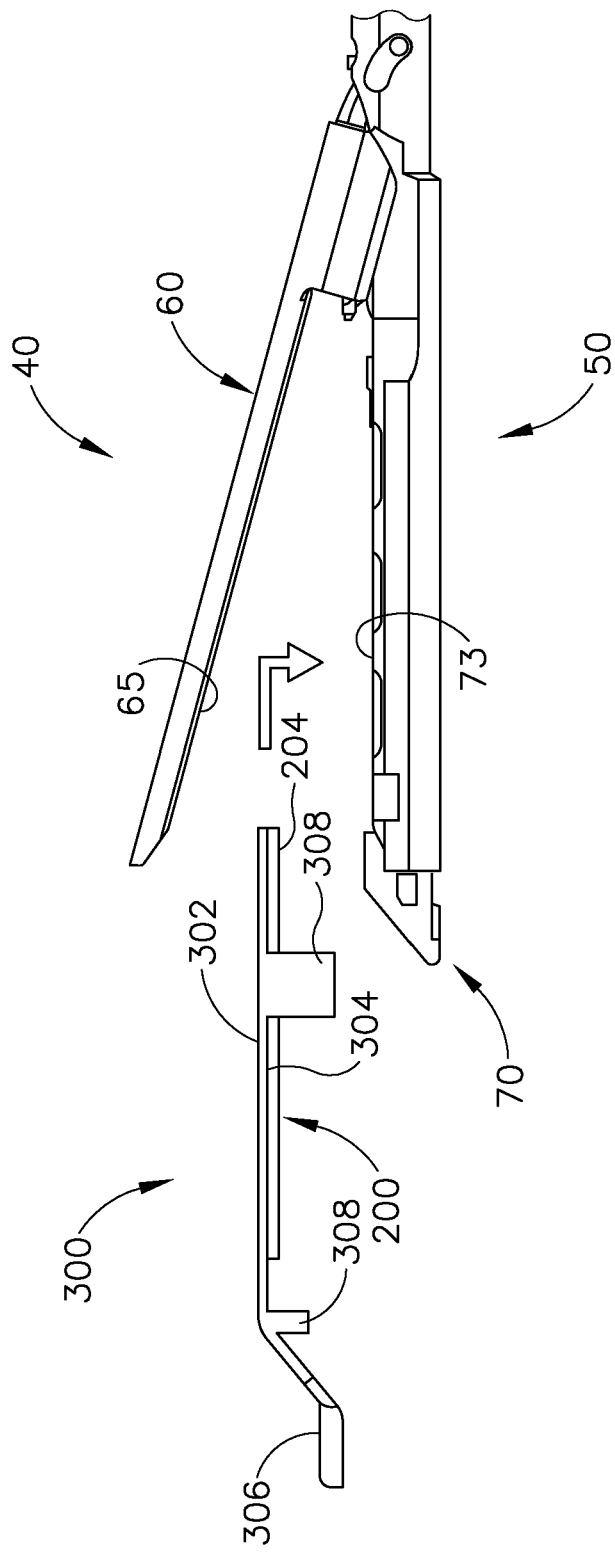
FIG. 12A depicts a side elevational view of the buttress and retainer of FIG. 10 positioned for engagement with the end effector of FIG. 3.
Figure 12D:
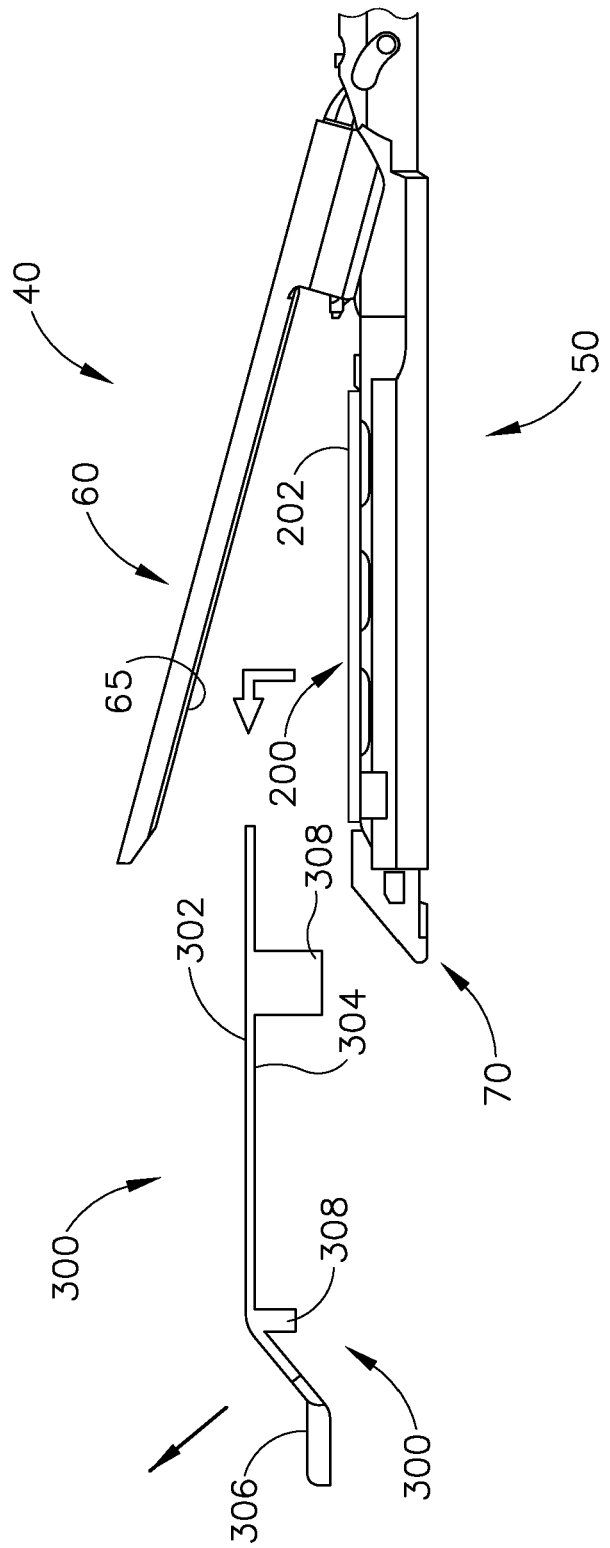
FIG. 12D depicts a side elevational view of the retainer of FIG. 10 being moved away from the end effector of FIG. 3, with the buttress of FIG. 10 being left behind on the end effector to form an end effector and buttress assembly.

As shown in FIG. 12A, the assembly formed by buttress (200) and retainer (300) may be placed before end effector (40) with anvil (60) in the open position. In some instances, a peel-away film (not shown) is positioned over underside (204) of buttress (200) to protect buttress (200) and/or any adhesive material on underside (204) of buttress (200). In such versions, the film is peeled away to expose underside (204) of buttress (200) before reaching the stage shown in FIG. 12A. Such a film may comprise polytetrafluoroethylene (PTFE) and/or any other suitable material(s). After reaching the stage shown in FIG. 12A, the assembly formed by buttress (200) and retainer (300) may then be placed on staple cartridge (70) such that underside (204) of buttress (200) apposingly contacts deck (73) of staple cartridge (70); and such that latches (308) are releasably secured to lower jaw (50) as shown in FIG. 12B. The operator may then drive anvil (60) toward the closed position as shown in FIG. 12C, eventually compressing buttress (200) against deck (73) of staple cartridge (70). Such compression may promote adhesion between underside (204) of buttress (200) and deck (73) of staple cartridge (70). After anvil (60) has been used to compress buttress (200) against deck (73) of staple cartridge (70), anvil (60) may be moved back to the open position as shown in FIG. 12D. As also shown in FIG. 12D, retainer (300) may then be pulled away from end effector (40), leaving behind buttress (200) adhered to deck (73) of staple cartridge (70). Upper side (202) of buttress (200) is exposed. End effector (40) is thus loaded with buttress (200) and ready for use in severing and stapling tissue (90).

Figure 14:
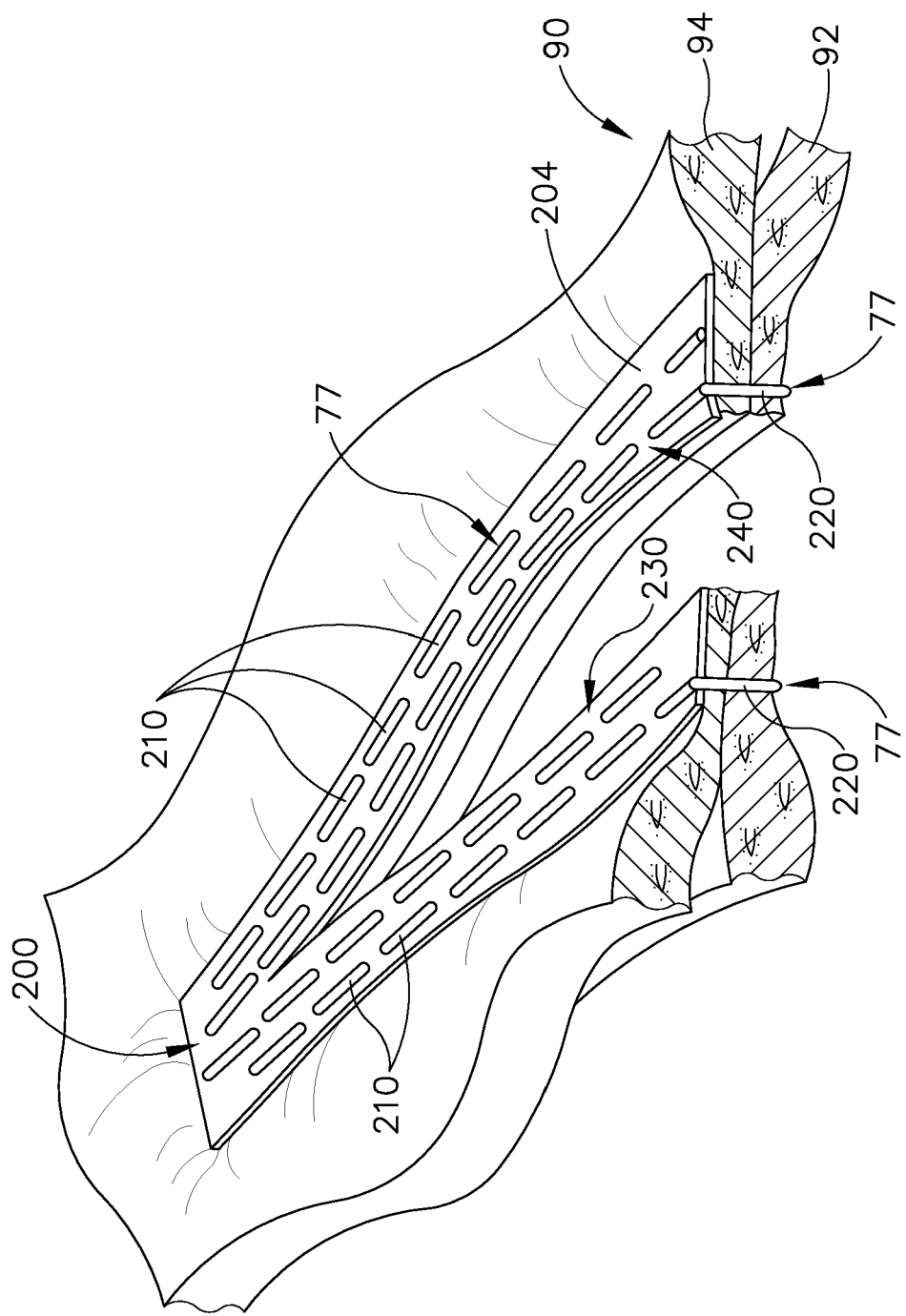
FIG. 14 depicts a perspective view of staples and the buttress of FIG. 12D having been secured to tissue by the end effector of FIG. 12D.
Figure 15:
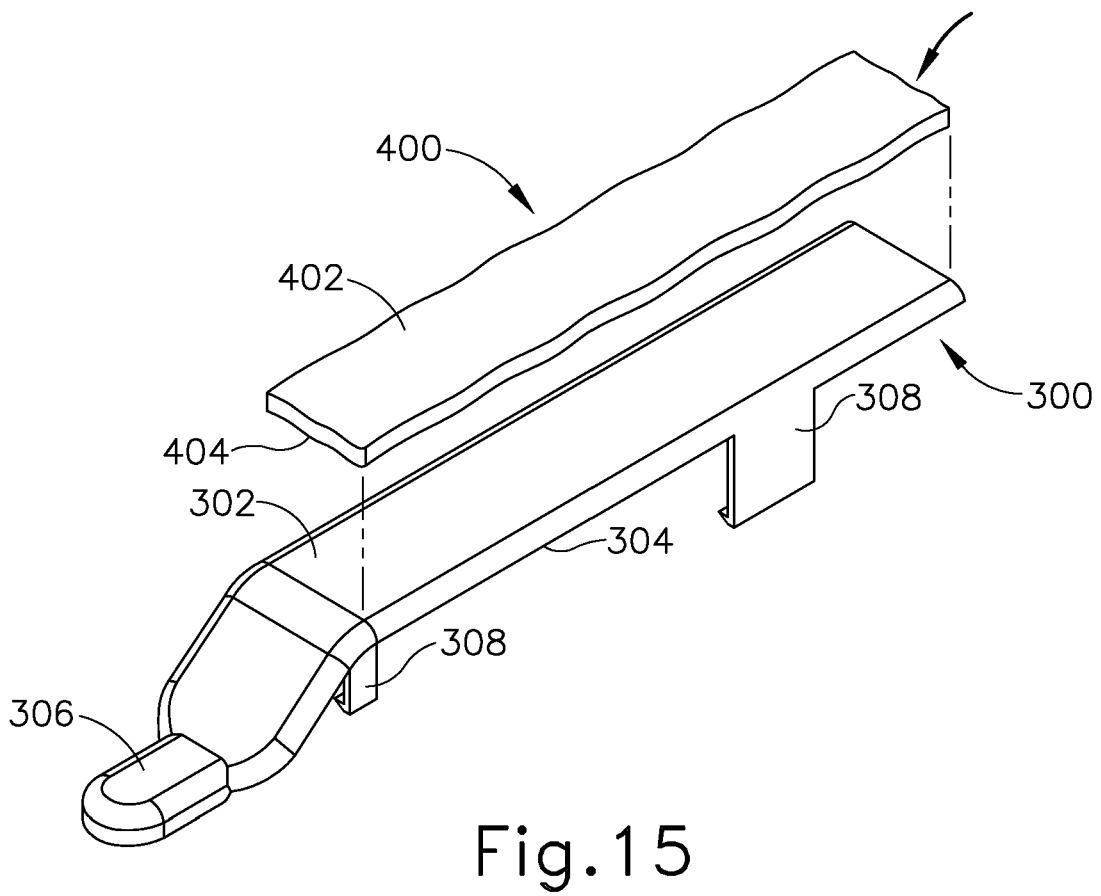
FIG. 15 depicts an exploded perspective view of an exemplary buttress and retainer.
Figure 16:
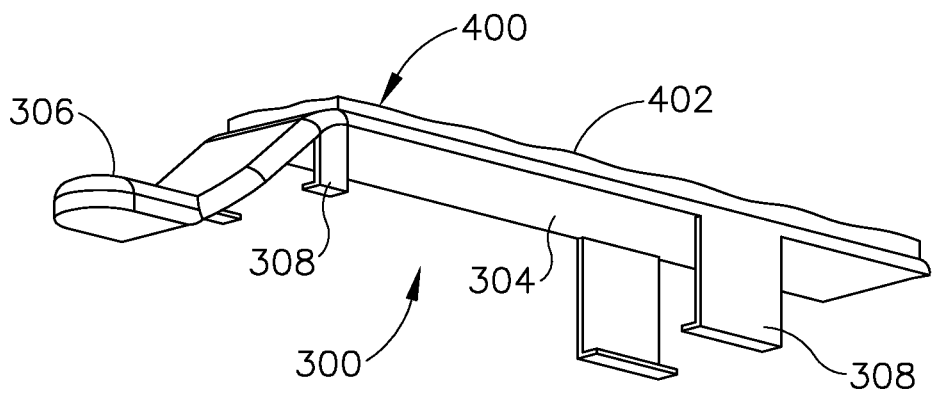
FIG. 16 depicts a perspective view of the buttress and retainer of FIG. 15, with the buttress secured to the top side of the retainer.

FIGS. 13A-13C show an end effector (40) loaded with buttress (200) being used to drive a staple (77) through tissue (90). In FIG. 13A, tissue (90) is placed between anvil (60) and staple cartridge (70), above buttress (200), with anvil (60) in the open position. In FIG. 13B, anvil (60) is driven to the closed position, compressing tissue (90) against buttress (200) and staple cartridge (70). End effector (40) is then actuated as described above, driving staple (77) through buttress (200) and tissue (90). As shown in FIG. 13C, crown (210) of driven staple (77) captures and retains buttress (200) against layer (94) of tissue (90). It should be understood that a series of staples (77) will similarly capture and retain buttress (200) against layer (94) of tissue (90), thereby securing buttress (200) to tissue (90) as shown in FIG. 14. As end effector (40) is pulled away from tissue (90) after deploying staples (77) and buttress (200), buttress (200) disengages deck (73) of staple cartridge (70), such that buttress (200) remains secured to tissue (90) with staples (77). Buttress (200) thus provides structural reinforcement to the lines of staples (77). As can also be seen in FIG. 14, knife member (80) also cuts through a centerline of buttress (200), separating buttress (200) into two sections (230, 240), such that each section (230, 240) remains secured to a respective severed region of tissue (90).

C. Exemplary Instrument and Technique for Securing Buttress to Anvil of End Effector FIGS. 15-17B show a combination of an exemplary buttress (400) with retainer (300). Buttress (400) of this example may be constructed in accordance with the teachings above relating to buttress assembly (100) and/or in accordance with other teachings herein. Buttress (400) includes an upper side (402) and an underside (404). In the present example, upper side (402) includes an adhesive (e.g., like upper adhesive layer (1064) to secure buttress (200) to underside (65) of anvil (60) as described in greater detail below.

In the present example, buttress (400) is secured to upper side (302) of retainer (300), such that underside (404) of buttress (400) apposes upper side (302) of retainer (300). In some versions, an adhesive such as lower adhesive layer (106) provides releasable adhesion of buttress (400) to upper side (302) of retainer (300). In some other versions, retainer (300) includes one or more features (e.g., flanges, clips, etc.) that are configured to selectively retain buttress (400) against upper side (302) of retainer (300). Various suitable ways in which buttress (200) may be releasably secured to upper side (302) of retainer (300) will be apparent to those of ordinary skill in the art in view of the teachings herein.

Figure 17A:
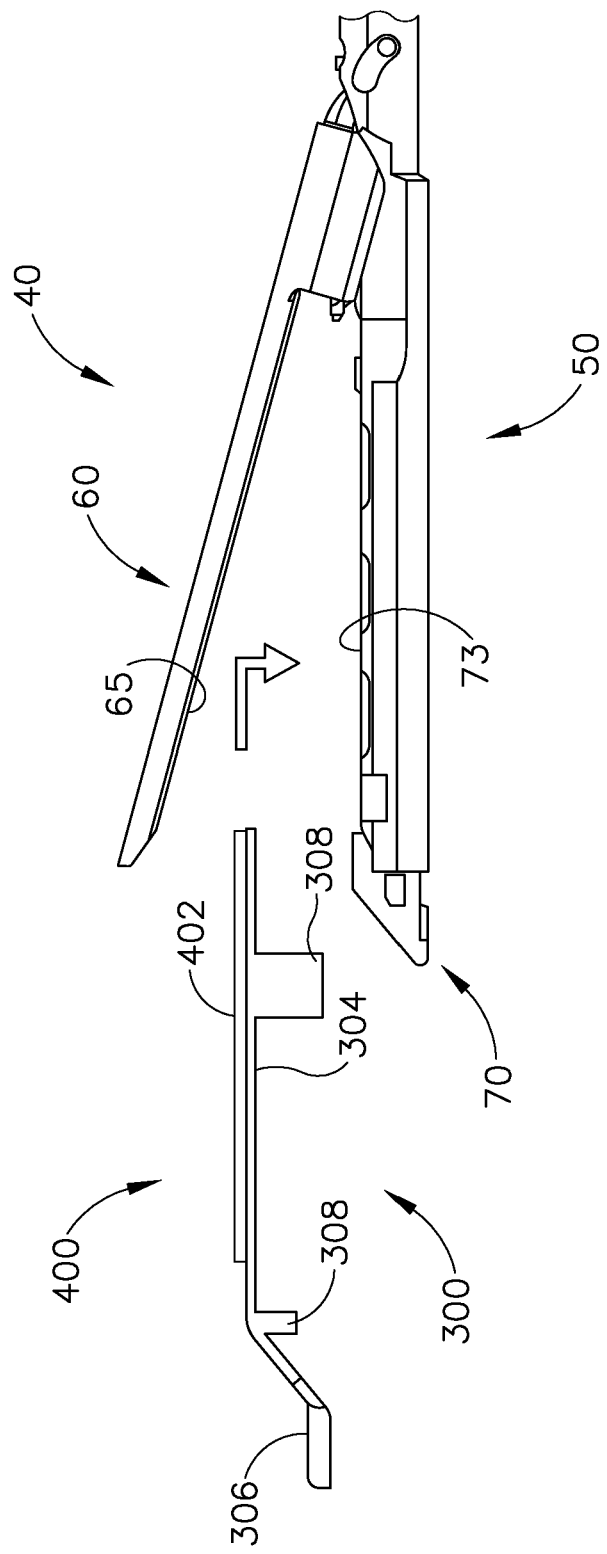
FIG. 17A depicts a side elevational view of the buttress and retainer of FIG. 15 positioned for engagement with the end effector of FIG. 3.
Figure 17B:
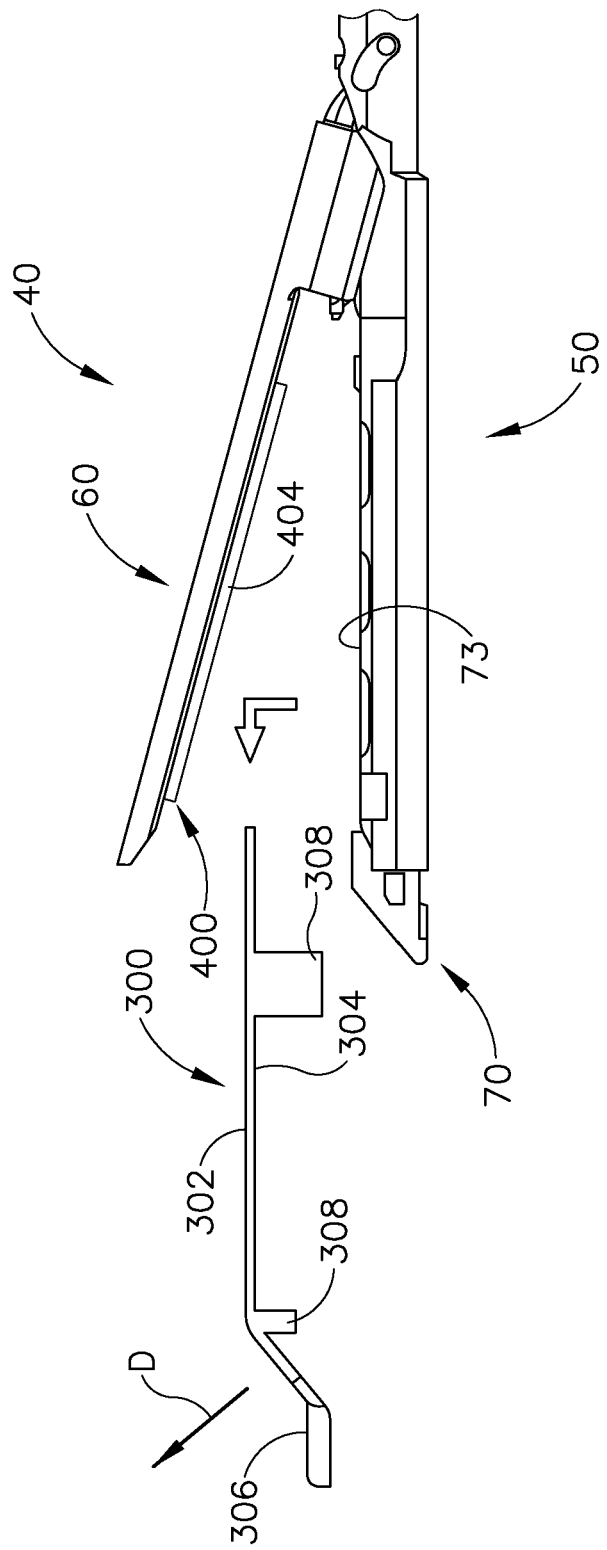
FIG. 17B depicts a side elevational view of the retainer of FIG. 15 being moved away from the end effector of FIG. 3, with the buttress of FIG. 15 being left behind on the end effector to form an end effector and buttress assembly.

As shown in FIG. 17A, the assembly formed by buttress (400) and retainer (300) may be placed before end effector (40) with anvil (60) in the open position. In some instances, a peel-away film (not shown) is positioned over upper side (402) of buttress (400) to protect buttress (400) and/or any adhesive material on upper side (402) of buttress (400). In such versions, the film is peeled away to expose upper side (402) of buttress (400) before reaching the stage shown in FIG. 17A. Such a film may comprise polytetrafluoroethylene (PTFE) and/or any other suitable material(s). After reaching the stage shown in FIG. 17A, the assembly formed by buttress (400) and retainer (300) may then be placed on staple cartridge (70) such that latches (308) are releasably secured to lower jaw (50) as described above. The operator may then drive anvil (60) toward the closed position as described above, eventually compressing buttress (400) underside (65) of anvil (60). Such compression may promote adhesion between upper side (402) of buttress (400) and underside (65) of anvil (60). After anvil (60) has been used to compress buttress (200) against underside (65) of anvil (60), anvil (60) may be moved back to the open position as shown in FIG. 17B. As also shown in FIG. 17B, retainer (300) may then be pulled away from end effector (40), leaving behind buttress (400) adhered to underside (65) of anvil (60). Underside (402) of buttress (400) is exposed. End effector (40) is thus loaded with buttress (400) and ready for use in severing and stapling tissue (90).

Figure 19:
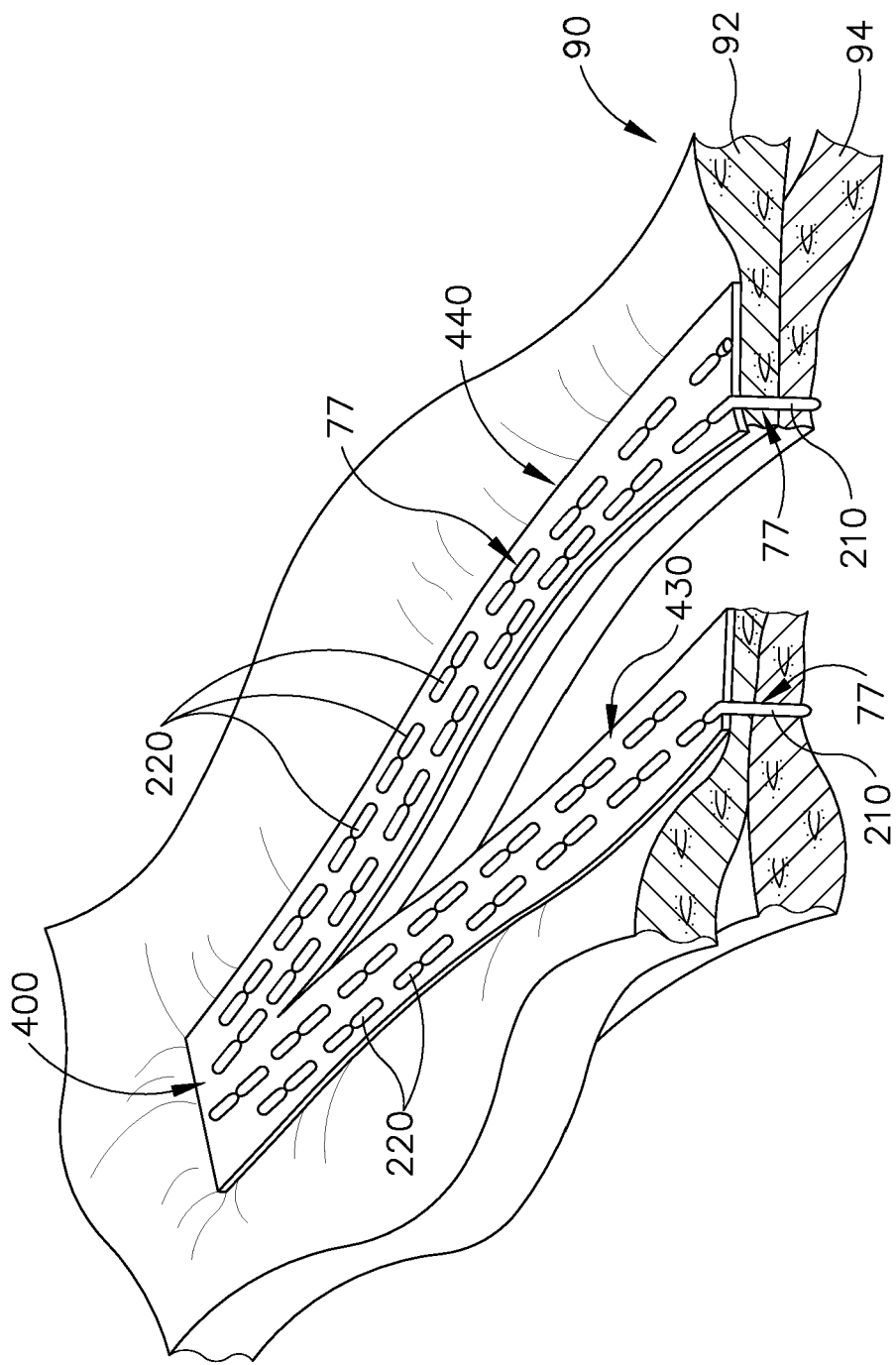
FIG. 19 depicts a perspective view of staples and the buttress of FIG. 17B having been secured to tissue by the end effector of FIG. 17B.

FIGS. 18A-18C show an end effector (40) loaded with buttress (400) being used to drive a staple (77) through tissue (90). In FIG. 18A, tissue (90) is placed between anvil (60) and staple cartridge (70), below buttress (400), with anvil (60) in the open position. In FIG. 18B, anvil (60) is driven to the closed position, compressing tissue (90) against buttress (400) and staple cartridge (70). End effector (40) is then actuated as described above, driving staple (77) through buttress (400) and tissue (90). As shown in FIG. 18C, bent legs (220) of driven staple (77) capture and retains buttress (400) against layer (92) of tissue (90). It should be understood that a series of staples (77) will similarly capture and retain buttress (400) against layer (92) of tissue (90), thereby securing buttress (400) to tissue (90) as shown in FIG. 19. As anvil (60) is returned to the open position to enable end effector (40) to be pulled away from tissue (90) after deploying staples (77) and buttress (400), buttress (400) disengages underside (65) of anvil (60), such that buttress (400) remains secured to tissue (90) with staples (77). Buttress (400) thus provides structural reinforcement to the lines of staples (77). As can also be seen in FIG. 19, knife member (80) also cuts through a centerline of buttress (400), separating buttress (400) into two sections (430, 440), such that each section (430, 440) remains secured to a respective severed region of tissue (90).

While the examples above provide either buttress (200) on underside (304) of retainer (300) or buttress (400) on upper side (302) of retainer (300), it should be understood that both retainers (200, 400) may be provided on the same retainer (300) if desired. In particular, retainer (200) may be provided on underside (304) of retainer (300) while buttress (400) is provided on upper side (302) of retainer (300). This may result in buttress (200) being provided on deck (73) of staple cartridge (70) and buttress (400) being provided on underside (65) of anvil (60) in the same end effector (400). This may ultimately result in buttress (200) being secured against layer (94) of tissue (90) by crowns (210) of staples (77) while buttress (400) is secured against layer (92) of tissue (90) by bent legs (220) of the same staples (77).

III. Exemplary Materials and Techniques for Providing Adhesion of Buttress to Surgical Stapler As noted above, a buttress assembly (100) may include at least one layer (104, 106) of adhesive material (or other form of adhesive material) that adheres buttress body (102) to either underside (65) of anvil (60) or deck (73) of staple cartridge (70). Such an adhesive material may provide proper positioning of buttress body (102) before and during actuation of end effector (40); then allow buttress body (102) to separate from end effector (40) after end effector (40) has been actuated, without causing damage to buttress body (102) that is substantial enough to compromise the proper subsequent functioning of buttress body (102). It may be desirable to minimize the impact of such an adhesive material on the functioning of firing beam (82) wedge sled (78), and staple drivers (75). For instance, it may be desirable to prevent the adhesive material from blocking or otherwise providing significant resistance to movement of firing beam (82) wedge sled (78), and staple drivers (75). Moreover, the adhesive material should allow buttress body (102) to detach easily enough from an actuated end effector (40) to avoid tearing tissue (90) after staples (77) have been fired through the tissue and anvil (60) is moved to the open position.

In some instances, it may be desirable for the adhesive material to provide additional effects, beyond merely adhering buttress body (102) to either underside (65) of anvil (60) or deck (73) of staple cartridge (70). For instance, the adhesive material may include one or more components that provide a therapeutic effect, hemostatic effect, or other desired effect on tissue (90). As another merely illustrative example, the adhesive material may fill in at least part of the paths that are formed through tissue (90) and/or buttress body (102) by legs (220) of staple (77) being driven through tissue (90) and buttress body (102).

In some instances, the adhesive material for a buttress body (102) may be pressure sensitive. In addition or in the alternative, the adhesive material may be configured to take the form of surface irregularities of buttress body (102); in addition to or in lieu of taking the form of surface irregularities in underside (65) of anvil (60) and/or deck (73) of staple cartridge (70).

The above noted characteristics of an adhesive material for a buttress body (102) are merely illustrative examples. Suitable adhesive materials may possess various other characteristics in addition to or in lieu of those above. Suitable adhesive materials may also be provided in various different kinds of compositions. Examples of various suitable compositions and configurations that may be used to form and provide an adhesive material for a buttress body (102), as well as various exemplary characteristics that such adhesive material may possess, are described in greater detail below.

A. Exemplary Polymeric Adhesive Materials with Synthetic Base

In some instances, an adhesive material (e.g., one or more of layers (104, 106)) for a buttress body (102) comprises an absorbable synthetic based polymer. Various physiomechanical properties of synthetic based polymers may be modified in order to provide different adhesive properties. Such variable characteristics include but are not limited to copolymer composition, glass transition temperature (Tg), molecular weight, inherent viscosity (IV), crystallinity, sequence distribution, copolymer chain composition, melting temperature (Tm), and surface tension. Several exemplary combinations of these variables will be provided below, though it should be understood that these examples are merely illustrative. It should also be understood that these examples of adhesive materials may be provided in upper adhesive layer (104). In addition or in the alternative, these examples of adhesive materials may be provided in lower adhesive layer (106). In addition or in the alternative, these examples of adhesive materials may be otherwise integrated into buttress body (102). It should therefore be understood that the adhesive material need not necessarily constitute a separate layer that is discretely identifiable as being different from a layer defined by buttress body (102).

In some examples, the adhesive material is formed by a copolymer of lactide and caprolactone (PLA/PCL). This composition may be provided at a ratio in the range of 20/80 to 60/40; or more particularly the range of 35/65 to 50/50. This composition may have a glass transition temperature (Tg) that is below 4° C., or more particularly below −10° C. This composition may have a molecular weight in the range of 10,000 g/mol to 145,000 g/mol; or more particularly below 200,000 g/mol. The composition may have an inherent viscosity (IV) in the range of 1.0 dL/g to 2.0 dL/g.

In some other examples, the adhesive material is formed by a copolymer of lactide and trimethylene carbonate (PLA/TMC). This composition may be provided at a ratio in the range of 20/80 to 50/50. The other characteristics may be within the same parameters set forth above with respect to the exemplary PLA/PCL composition. Alternatively, the PLA/TMC composition may have any other suitable characteristics.

In some other examples, the adhesive material is formed by a copolymer of trimethylene carbonate and caprolactone (TMC/PCL). This composition may be provided at a ratio in the range of 20/80 to 80/20; or more particularly in the range of 50/50 to 60/40. This composition may have an inherent viscosity (IV) in the range of 0.3 dL/g to 3.0 dL/g; or more particularly in the range of 0.5 dL/g to 1.0 dL/g. This composition may have a crystallinity below 20%; or more particularly below 5%; or more particularly at 0% (i.e., a completely amorphous polymer). This composition may have a glass transition temperature (Tg) below 0° C.; or more particularly below −20° C.

In some other examples, the adhesive material is formed by a copolymer of caprolactone and glycolide (PCL/PGA). This composition may be provided at a ratio in the range of 45/55 to 85/15; or more particularly in the range of 40/60 to 65/35; or more particularly in the range of 50/50 to 65/35. This composition may have an inherent viscosity (IV) in the range of 0.2 dL/g to 3.0 dL/g; or more particularly in the range of 1.0 dL/g to 2.0 dL/g. This composition may have a molecular weight in the range of 100,000 g/mol to 200,000 g/mol. This composition may have a crystallinity below 20%; or more particularly below 5%; or more particularly at 0% (i.e., a completely amorphous polymer). This composition may have a glass transition temperature (Tg) below 0° C.; or more particularly below −20° C. One particular example of this composition has a ratio of 50/50 PCL/PGA; an inherent viscosity (IV) of 0.2; a molecular weight of 83,000 g/mol; and a glass transition temperature (Tg) of −19.4°. Another particular example of this composition has a ratio of 65/35 PCL/PGA; an inherent viscosity (IV) of 1.04 to 1.07; a molecular weight of 110,000 g/mol to 118,000 g/mol; and a glass transition temperature (Tg) in the range of −37.3° to −38.6°.

Other exemplary synthetic based polymer compositions that may be used to form the adhesive material include the following: propanediol and caprolactone (PDO/PCL); a combination of propanediol, caprolactone, and trimethylene carbonate (PDO/PCL/TMC), with very low to no crystallinity and a glass transition temperature (Tg) below 0° C.; and a homopolymer poly(TMC), with an inherent viscosity (IV) of approximately 0.5 dL/g. Other suitable synthetic based polymer compositions will be apparent to those of ordinary skill in the art in view of the teachings herein.

The adhesive material may include a blocky copolymer. For instance, one example of a blocky copolymer that may be used in the adhesive material comprises blocky poly (TMC), with a low glass transition temperature (Tg). In some instances, the blocky copolymer may be randomized. In some other instances, such as when the copolymer is amorphous (e.g., 0% crystallinity), the blocky copolymer may be ordered.

The adhesive material may include various kinds of copolymer chain compositions. For instance, the copolymer chain composition may be branched with relatively short segments. This may further enhance the malleability experience. Alternatively, the copolymer chain may be linear. As another alternative, the copolymer may be cross-linked or star pattern. However, in versions where the copolymer is cross-linked, it may be desirable for the base copolymer segments to be more amorphous the more that those segment are cross-linked.

As noted above, the melting temperature (Tm) is a physiomechanical property of a polymer that may be selected to provide desired adhesive characteristics. In some instances, the lower melting temperature (Tm) of a monomer component could limit the amount of the co-monomer needed to create a desired adhesive effect. By way of example only, polydioxanone (PDS) has a melting temperature (Tm) around approximately 110° C. and a glass transition temperature (Tg) around approximately −10° C. Thus, polydioxanone (PDS) may need less caprolactone (PCL) to make a suitable pressure sensitive adhesive (PSA) copolymer. It should also be understood that polydioxanone (PDS) copolymers with polyglycolide (PGA) or lactide (PLA) may provide desired adhesive effects. It may be desirable for such copolymers to have a glass transition temperature (Tg) that is below room temperature; a melting temperature (Tm) that is at or below room temperature; a crystallinity in the range of 10% to 0%; and an inherent viscosity (IV) that is less than 2.0 dL/g, or more particularly less than 1.0 dL/g.

In some examples the adhesive material may comprise a blended copolymer. For instance, the high and low molecular weight of the same pressure sensitive adhesive (PSA) copolymer may allow for the degradation rate to be adjusted without adjusting the polymer chemistry. As the low molecular weight version breaks down, its acid byproducts would then change the pH and effect the breakdown of the high molecular weight parts. Preferred blends of copolymers would include those that will not affect the crystallinity, low melting temperature (Tm), and low glass transition temperature (Tg) of the copolymers.

Some examples of the adhesive material may comprise polyurethane. For instance, the polyurethane may be provided as a pressure sensitive adhesive (PSA). By of example only, polyurethane based pressure sensitive adhesives (PSAs) may be prepared from isocyanates, polyols, and chain extenders. Pressure sensitive adhesives (PSAs) may also be prepared from 100% solids, waterborne, or solvent borne systems. The properties of polyurethane based pressure sensitive adhesives (PSAs) may be controlled by varying the ratio of isocyanates to polyols and chain extenders. As another merely illustrative example, the polyurethane may be provided in a flowable form. For instance, a flowable polyurethane based adhesive material may have an inherent viscosity (IV) that is less than 1.0 dL/g, or more particularly less than 0.5 dL/g; a glass transition temperature (Tg) that is in the range of −10° C. and 10° C.; or more particularly closer to −10° C.; and a consistency similar to that of honey or oil, if desired, with the proper inherent viscosity (IV).

The foregoing examples of absorbable synthetic based polymers are provided for merely illustrative purposes. Other suitable examples will be apparent to those of ordinary skill in the art in view of the teachings herein. It should also be understood that the foregoing examples of absorbable synthetic based polymers may be readily incorporated into the various teachings and examples provided below. In other words, the foregoing examples of absorbable synthetic based polymers may be readily incorporated into any example herein that refers to an adhesive material.

B. Exemplary Polymeric Adhesive Materials with Natural Base

While the above discussion provides various examples of synthetic based polymers that may be used as an adhesive material (e.g., one or more of layers (104, 106)) for a buttress body (102), it should also be understood that a natural based polymer may be used as an adhesive material. Several merely illustrative examples of natural based polymers that may be used as an adhesive material will be described in greater detail below. It should also be understood that these examples of adhesive materials may be provided in upper adhesive layer (104). In addition or in the alternative, these examples of adhesive materials may be provided in lower adhesive layer (106). In addition or in the alternative, these examples of adhesive materials may be otherwise integrated into buttress body (102). It should therefore be understood that the adhesive material need not necessarily constitute a separate layer that is discretely identifiable as being different from a layer defined by buttress body (102).

In some instances, the adhesive material comprises a hydrogel. The hydrogel may generally comprise a hydrophilic polymer network capable of absorbing and/or retaining fluids. An exemplary hydrogel material is glycol methacrylate. By way of further example only, suitable hydrogel materials may comprise homopolymer hydrogels, copolymer hydrogels, multipolymer hydrogels, interpenetrating polymer hydrogels, and combinations thereof. In further examples, the hydrogel may comprise microgels, nanogels, and combinations thereof. The hydrogel may further comprise a non-crosslinked hydrogel, a crosslinked hydrogel, and combinations thereof. The hydrogel may comprise chemical crosslinks, physical crosslinks, hydrophobic segments and/or water insoluble segments. The hydrogel may be chemically crosslinked by polymerization, small-molecule crosslinking, and/or polymer-polymer crosslinking. The hydrogel may be physically crosslinked by ionic interactions, hydrophobic interactions, hydrogen bonding interactions, sterocomplexation, and/or supramolecular chemistry. The hydrogel may be substantially insoluble due to the crosslinks, hydrophobic segments and/or water insoluble segments, but be expandable and/or swellable due to absorbing and/or retaining fluids. In some versions, the precursor may crosslink with endogenous materials and/or tissues.

Further examples of hydrogels that may be used include multifunctional acrylates, hydroxyethylmethacrylate (HEMA), and elastomeric acrylates. In additional or in the alternative, a hydrogel adhesive material may be constructed in accordance with at least some of the teachings of U.S. Pat. Pub. No. 2012/0241492, entitled "Tissue Thickness Compensator Comprising at Least One Medicament," published Sep. 27, 2012, issued as U.S. Pat. No. 9,839,420 on Dec. 12, 2017, the disclosure of which is incorporated by reference herein. Other suitable ways in which an adhesive material may be provided with hydrogel will be apparent to those of ordinary skill in the art in view of the teachings herein.

Further examples of naturally based polymers that may be used to form an adhesive material include alginate (e.g., calcium alginate, calcium sodium alginate, etc.); hyaluronic acid, collagen (including gelatin), and polysaccharide. In versions including a polysaccharide, the polysaccharide may include cellulose, chitin, pectin, or arabinoxylans. In versions including cellulose, the cellulose may comprise oxidized regenerated cellulose, carboxy-methylcellulose, carboxyethyl cellulose, hydroxypropyl cellulose, hydroxyethyl cellulose, or oxidized cellulose. In versions including chitin, the chitin may comprise chitosan (e.g., deacetylated chitin) or chitosan salts.

Some versions of naturally based polymers that may be used to form an adhesive material may include a putty or wax-like material. Some such versions may be non-absorbable and may be similar to a conventional bone wax. For instance, the material may comprise beeswax with one or more of the paraffin, petroleum jelly, isopropyl palmitate, sesame oil, carbolic acid; or any other conventional bone wax composition. Some other versions of a putty or wax-like material that may be used to form an adhesive material for buttress body (102) may be absorbable or resorbable. For instance, some such versions may comprise HEMASORB® putty by Abyrx, Ink of Irvington, N.Y., water-soluble alkylene copolymers (e.g., OSTENE by Baxter Healthcare Corporation of Deerfield, Ill.), glycerol, 1-lactide, glycolide, polyethylene glycol (PEG), polyethylene oxide (PEO), or polyolefin elastomer (POE). By way of further example, the adhesive material may comprise polyethylene glycol (PEG) or a polyethylene glycol (PEG) copolymer with a molecular weight of less than 20,000 g/mol. Having the molecular weight in such a range may promote passage of the dissolved form of the adhesive through the kidneys. See, e.g., Webster et al., "PEGylated Proteins: Evaluation of Their Safety in the Absence of Definitive Metabolism Studies," *Drug Metabolism and Disposition*, Vol. 35, No. 1, pp. 9-16 (2007), the disclosure of which is incorporated by reference herein. As yet another merely illustrative example, the adhesive material may be constructed in accordance with at least some of the teachings of U.S. Pat. No. 2,642,375, entitled "Hemostatic Compositions," issued Jun. 16, 1953, the disclosure of which is incorporated by reference herein.

Some polymer adhesives, including but not limited to the putty or wax-like compositions referred to above, may include oxidized regenerated cellulose (ORC), which is a hemostatic agent. For instance, a putty or wax-like composition may serve as a carrier for oxidized regenerated cellulose (ORC). U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018 the disclosure of which is incorporated by reference herein, discusses various ways in which oxidized regenerated cellulose (ORC) may be incorporated into various compositions. It should be understood that such teachings of U.S. Patent Pub. No. 2012/0241493, issued as U.S. Pat. No. 10,123,798 on Nov. 13, 2018, may be readily applied herein in the context of incorporating oxidized regenerated cellulose (ORC) into polymer adhesives, including but not limited to the putty or wax-like compositions referred to above.

The foregoing examples of natural based polymers are provided for merely illustrative purposes. Other suitable examples will be apparent to those of ordinary skill in the art in view of the teachings herein. It should also be understood that the foregoing examples of natural based polymers may be readily incorporated into the various teachings and examples provided below. In other words, the foregoing examples of natural based polymers may be readily incorporated into any example herein that refers to an adhesive material.

C. Exemplary Malleable Bioabsorbable Polymer Adhesive

In some instances, it may be desirable to provide one or more adhesive layers (104, 106) with a malleable bioabsorbable polymer adhesive. Such a polymer may be highly viscous yet still flowable at room temperature. A malleable polymer adhesive may, in response to pressure being applied to it, take the form of a surface with which it is engaged. In other words, if a malleable polymer adhesive is pressed against deck (73) of staple cartridge (70), the malleable polymer adhesive may take the form of the one or more features of the deck (73) that it the malleable polymer adhesive is pressed against. Similarly, if a malleable polymer adhesive is pressed against underside (65) of anvil (60), the malleable polymer adhesive may take the form of the one or more features of underside (65) that it the malleable polymer adhesive is pressed against. By deforming to the geometry that it is pressed against, the malleable polymer adhesive may adhere to the geometry; and may further provide re-applyable attachment. If the desired positioning of buttress assembly (100) on deck (73) or underside (65) is not achieved, the malleable polymer adhesive may permit buttress assembly (100) to be removed, repositioned, and re-adhered to deck (73) or underside (65). It should be understood that the examples provided below may be malleable at room temperature, such that additional heating or other treatment is not necessary in order to provide malleability.

Providing the adhesive material in the form of a malleable polymer may minimize the impact of fluids and debris on the adhesion of buttress assembly (100) to deck (73) of staple cartridge (70) or underside (65) of anvil (60). The malleable polymer adhesive material may also be hydrophilic (e.g., at least in certain regions of buttress assembly (100)), encouraging adhesion in a wet environment. In addition or in the alternative, adhesive layer (104, 102) of buttress assembly (100) may include a combination of adhesive material and hydrophobic material in respective localized regions. The hydrophobic material may drive fluids out of the adhesion areas, thereby improving adhesion at the localized regions of adhesive material.

In some instances, when a buttress assembly (100) having a malleable bioabsorbable polymer adhesive is sterilized using ethylene oxide at a high temperature, the ethylene oxide gas may act as a plasticizer, increasing the fluidic aspects of the adhesive. Buttress assembly (100) may include features that are configured to contain the adhesive at this stage (and/or at other stages where the adhesive may become more fluidic), to maintain the adhesive properties of the adhesive later in its life cycle. For instance, such containment features may be provided by buttress body (102). In addition or in the alternative, such containment features may be provided by a peel away film layer that is provided on the opposite side of adhesive layer (104, 106), such that the adhesive layer (104, 106) is interposed between buttress body (102) and the peel away film layer. Such a peel away film layer may comprise recesses or cavities, etc., as features that provide a predefined space where the viscous fluid adhesive may be retained. Other suitable forms of adhesive retention features will be apparent to those of ordinary skill in the art in view of the teachings herein.

The below examples include various compositions of malleable bioabsorbable polymer adhesives and various exemplary configurations through which a malleable bioabsorbable polymer adhesive may be combined with a buttress body (102). In the present example, it is contemplated that the adhesive material comprises a synthetic based polymer such as those referred to herein. However, it should also be understood that naturally based polymers may be incorporated with the below teachings. It should also be understood that, even if some of the below examples are provided specifically in the context of being applied to just deck (73) of staple cartridge (70), the same examples may be readily applied to underside (65) of anvil (60). Similarly, to the extent that some of the below examples are provided specifically in the context of being applied to just underside (65) of anvil (60), the same examples may be readily applied to deck (73) of staple cartridge (70).

1 Exemplary Compositions Providing Malleable Absorbable Polymer Adhesive

In some versions, the polymer adhesive is provided in a thin layer having properties in the range of malleable to flowable (high viscosity), with a tacky surface contact. In some versions, such polymer adhesives have a low inherent viscosity (IV) with low crystallinity. One such composition may comprise a 65/35 copolymer of caprolactone and glycolide (PCL/PGA). Another such composition may comprise a 65/35 copolymer of trimethylene carbonate and caprolactone (TMC/PCL). Another such composition may comprise a 75/25 copolymer of lactide and caprolactone (PLA/PCL). Another such composition may comprise a copolymer of trimethylene carbonate and lactide (TMC/PLA).

It should also be understood that some of the putty or wax-like compositions previously referred to may be used to provide a malleable polymer adhesive. Absorbable versions of such compositions include HEMASORB® putty by Abyrx, Ink of Irvington, N.Y., water-soluble alkylene copolymers (e.g., OSTENE by Baxter Healthcare Corporation of Deerfield, Ill.), glycerol, 1-lactide, glycolide, and polyethylene glycol (PEG). Non-absorbable versions of such compositions include beeswax with one or more of the paraffin, petroleum jelly, isopropyl palmitate, sesame oil, carbolic acid; or any other conventional bone wax composition. Some malleable polymer adhesives, including but not limited to the putty or wax-like compositions, may include oxidized regenerated cellulose (ORC), as further noted above.

The foregoing are just a few merely illustrative examples of malleable polymer compositions that may be used to adhere buttress body (102) to underside (65) of anvil (60) or deck (73) of staple cartridge (70). By way of further example only, other suitable compositions may include various other compositions referred to herein and variations thereof.

2. Exemplary Structural Configurations Incorporating a Malleable Absorbable Polymer Adhesive with a Buttress There are a variety of structural configurations that may be used to incorporate a malleable absorbable polymer adhesive with a buttress body (102) to form a buttress assembly (100) that may be adhered to underside (65) of anvil (60) or deck (73) of staple cartridge (70). Several merely illustrative examples are described in greater detail below. Further examples will be apparent to those of ordinary skill in the art in view of the teachings herein. It should also be understood that, while the following examples are provided as separate examples, the concepts and features of the following examples may be combined with each other in numerous ways as will be apparent to those of ordinary skill in the art in view of the teachings herein.

a. Thin Film Malleable Polymer Adhesive on Buttress

A malleable absorbable polymer adhesive may be provided as a thin film on buttress body (102). In one merely illustrative example, a copolymer adhesive film layer (104, 106) is compression molded in a 65/35 caprolactone and glycolide (PCL/PGA) form to a thickness in the range of 75 mils to 250 mils. The compressed adhesive film layer (104, 106) can then be pressed into adhesive contact with buttress body (102). A polytetrafluoroethylene (PTFE) film may be applied to the exposed face of adhesive film layer (104, 106) to protect the face of adhesive film layer (104, 106). Right before the resulting buttress assembly (100) is to be applied to deck (73) of staple cartridge (70) or underside (65) of anvil (60), the polytetrafluoroethylene (PTFE) film may be removed to expose the adhesive film layer (104, 106). The exposed adhesive film layer (104, 106) may then be pressed against deck (73) of staple cartridge (70) or underside (65) of anvil (60), thereby adhering buttress assembly (100) to deck (73) of staple cartridge (70) or underside (65) of anvil (60).

In another merely illustrative example, a fluidic composition of 50/50 caprolactone and glycolide (PCL/PGA) is heated and painted onto buttress body (102), thereby providing a thin adhesive film layer (104, 106). As the film adhesive film layer (104, 106) cools to room temperature, the adhesive film layer (104, 106) behaves like a thick compressed film element to adhere to deck (73) of staple cartridge (70) or underside (65) of anvil (60). As described above, a polytetrafluoroethylene (PTFE) film may be used to selectively protect and expose the adhesive film layer (104, 106).

In versions where a malleable absorbable polymer adhesive is provided as a thin film on buttress body (102), it should be understood that adhesion may occur as the thin adhesive film layer (104, 106) is deformed due to compression against deck (73) of staple cartridge (70) or underside (65) of anvil (60). The adhesive film layer (104, 106) has a tacky surface condition but the adhesion may actually be provided through a combination of cohesion, surface tension, deformation of the contact surface to mate directly to the geometry of deck (73) of staple cartridge (70) or underside (65) of anvil (60), and some tacky adhesion, rather than just adhesion alone.

b. Openings Formed Through Malleable Polymer Adhesive Layer to Limit Migration

Figure 20:
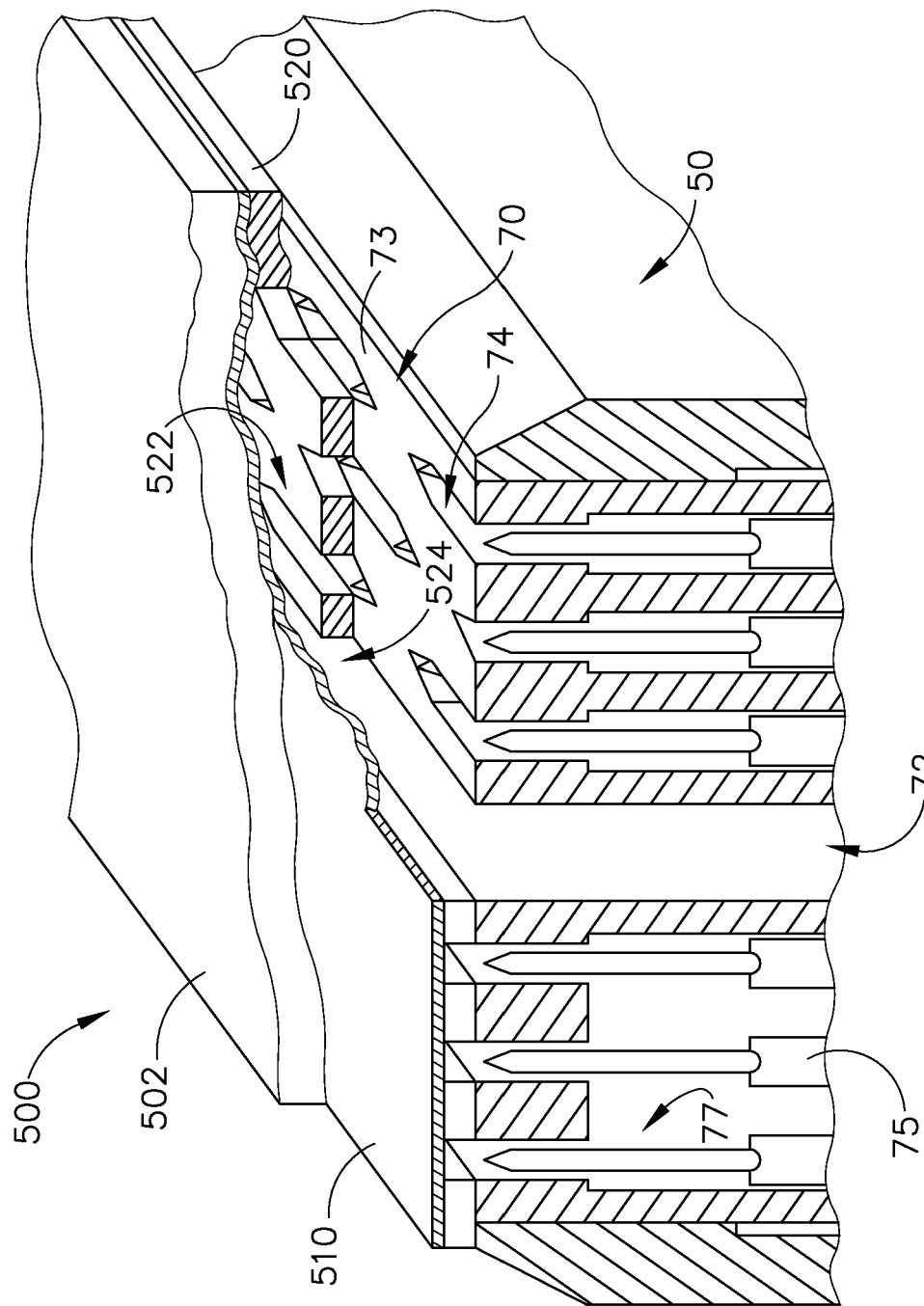
FIG. 20 depicts a partial, cross-sectional, perspective view of a staple cartridge with an exemplary buttress assembly secured thereto.

In some versions, buttress assembly (100) includes a geometry and/or other features that improve adhesion and/or prevent inadvertent flow of adhesive material into undesirable regions. FIGS. 20-21 show an exemplary buttress assembly (500) that is configured to provide such properties. Buttress assembly (500) of this example comprises a buttress body (502), an intermediate layer (510), and an adhesive layer (520). Buttress body (502) may be configured and operable just like buttress body (102) described above. Adhesive layer (520) may comprise any of the various adhesive materials referred to herein, including but not limited to any of the various absorbable malleable polymer compositions.

Intermediate layer (510) is interposed between buttress body (502) and adhesive layer (520). At least a portion of intermediate layer (510) may be impermeable or semi impermeable as described above, to prevent or restrict migration of adhesive material from adhesive layer (520) into buttress body (502). Intermediate layer (510) is configured to promote and prevent adhesion of the material forming adhesive layer (520) at different regions. In particular, as best seen in FIG. 20, in which buttress assembly (500) is applied to a deck (73) of a staple cartridge (70), adhesive layer (520) includes an opening (522) over each staple pocket (74) of staple cartridge (70). Openings (522) are configured to prevent the material forming adhesive layer (520) from entering or otherwise covering staple pockets (74), thereby preventing the adhesive layer from inhibiting the exit of staples (77) from staple pockets (74). Adhesive layer (520) further includes an opening (524) in the form of a longitudinal channel over channel (72) of staple cartridge (70). Opening (524) is configured to prevent the material forming adhesive layer (520) from entering or otherwise covering channel (72), thereby preventing the adhesive layer from inhibiting the distal motion of firing beam (82) through channel (72). In instances where buttress assembly (500) is applied to underside (65) of anvil (60), openings (522) may be sized and positioned to prevent the material forming adhesive layer (520) from entering or otherwise covering staple forming pockets (64). Similarly, opening (524) may be configured to prevent the material forming adhesive layer (520) from entering or otherwise covering channel (62).

In the present example, openings (522, 524) are formed due to the presence of features of intermediate layer (510) that are configured to prevent adhesion of the adhesive material. In other words, when the adhesive material is applied to intermediate layer during the process of forming adhesive assembly (500), those features of intermediate layer keep the adhesive material away from the regions where openings (522, 524) are intended to be formed. By way of example only, such features may comprise a micro and/or macro surface finish features and/or other kinds of features. As another merely illustrative example, intermediate layer (510) may comprise macro standing features that keep the adhesive material away from the regions where openings (522, 524) are intended to be formed. As yet another merely illustrative example, a die or other device may be used to keep the adhesive material away from the regions where openings (522, 524) are intended to be formed. Such a die may be removed at any suitable time before buttress assembly (500) is applied to deck (73) of staple cartridge (70) or underside (65) of anvil (60). Other suitable ways in which openings (522, 524) may be formed will be apparent to those of ordinary skill in the art in view of the teachings herein. It should also be understood that intermediate layer (510) may include a surface finish and/or other surface features that is/are configured to promote adhesion of the adhesive material to the regions outside of openings (522, 524).

FIG. 21 shows an example of a set of staples (77) driven through tissue (90), with two buttress assemblies (500) secured to the tissue (90). In this example, one buttress assembly (500) had been secured to deck (73) of staple cartridge (70) while another buttress assembly (500) had been secured to underside (65) of anvil (60). As can be seen, openings (522) are sized to accommodate staples (77) at each buttress assembly (500). Thus, neither crowns (210) nor legs (220) of staples (77) have passed through any of the material forming adhesive layer (520) in either buttress assembly (500).

c. Malleable Polymer Adhesive Rods

Figure 22A:
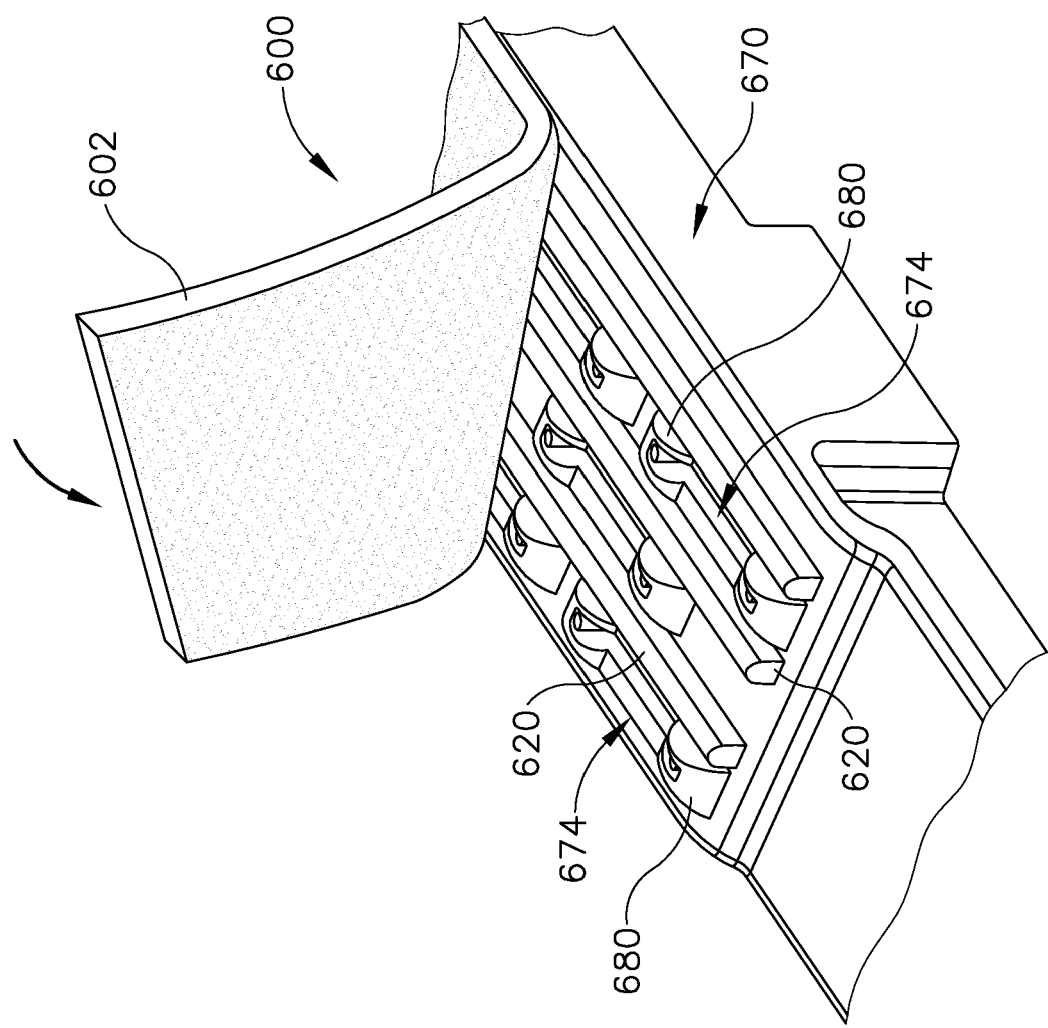
FIG. 22A depicts a partial perspective view of a staple cartridge with a buttress being laid over exemplary retention features.
Figure 22B:
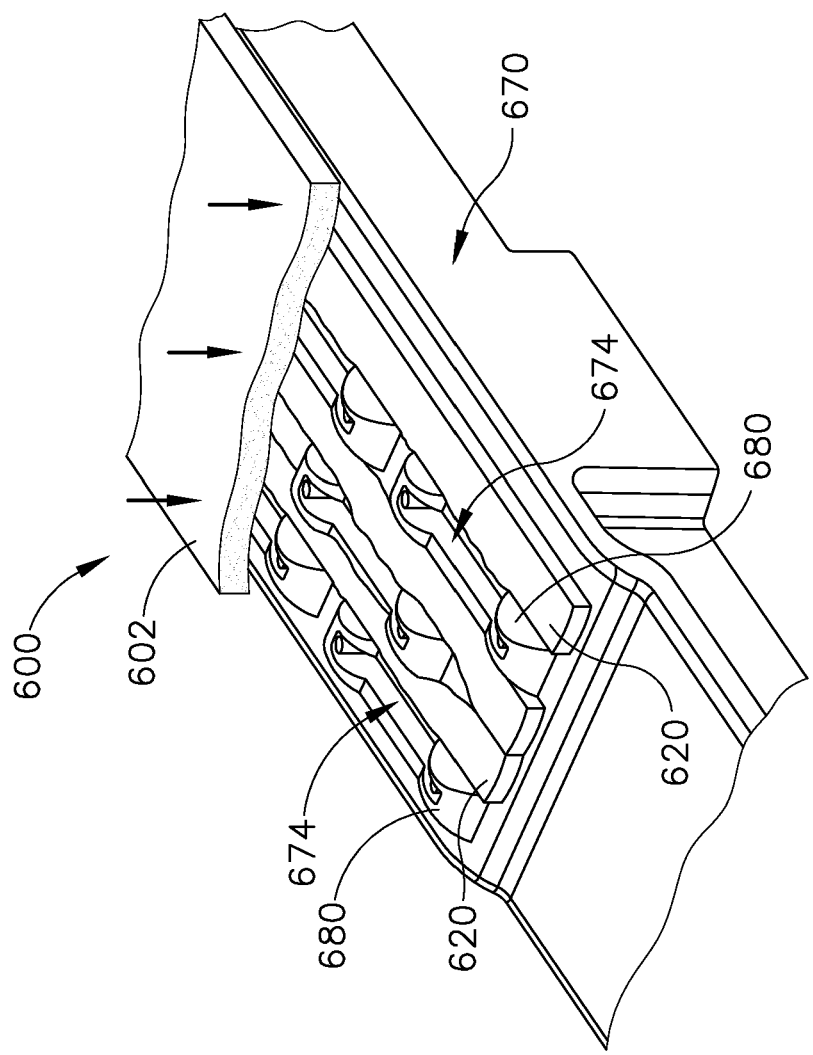
FIG. 22B depicts a partial perspective view of the staple cartridge of FIG. 22A, with the buttress being pressed against the retention features to thereby secure the buttress to the staple cartridge.

FIGS. 22A-22B show an exemplary buttress assembly (600) comprising a buttress body (602) and a set of adhesive rods (620). Buttress body (602) may be configured and operable just like buttress body (102) described above. Adhesive rods (620) may comprise any of the various adhesive materials referred to herein, including but not limited to any of the various absorbable malleable polymer compositions. By way of specific example only, adhesive layer (620) may comprise one of the putty or wax-like compositions previously referred to.

Buttress assembly (600) is shown as being used in combination with a staple cartridge (670) that is substantially similar to staple cartridge (70). However, staple cartridge (670) of this example comprises upwardly extending, U-shaped lip members (680) around the end of each staple pocket (674). Staple cartridge (670) is otherwise identical to staple cartridge (70).

Figure 23:
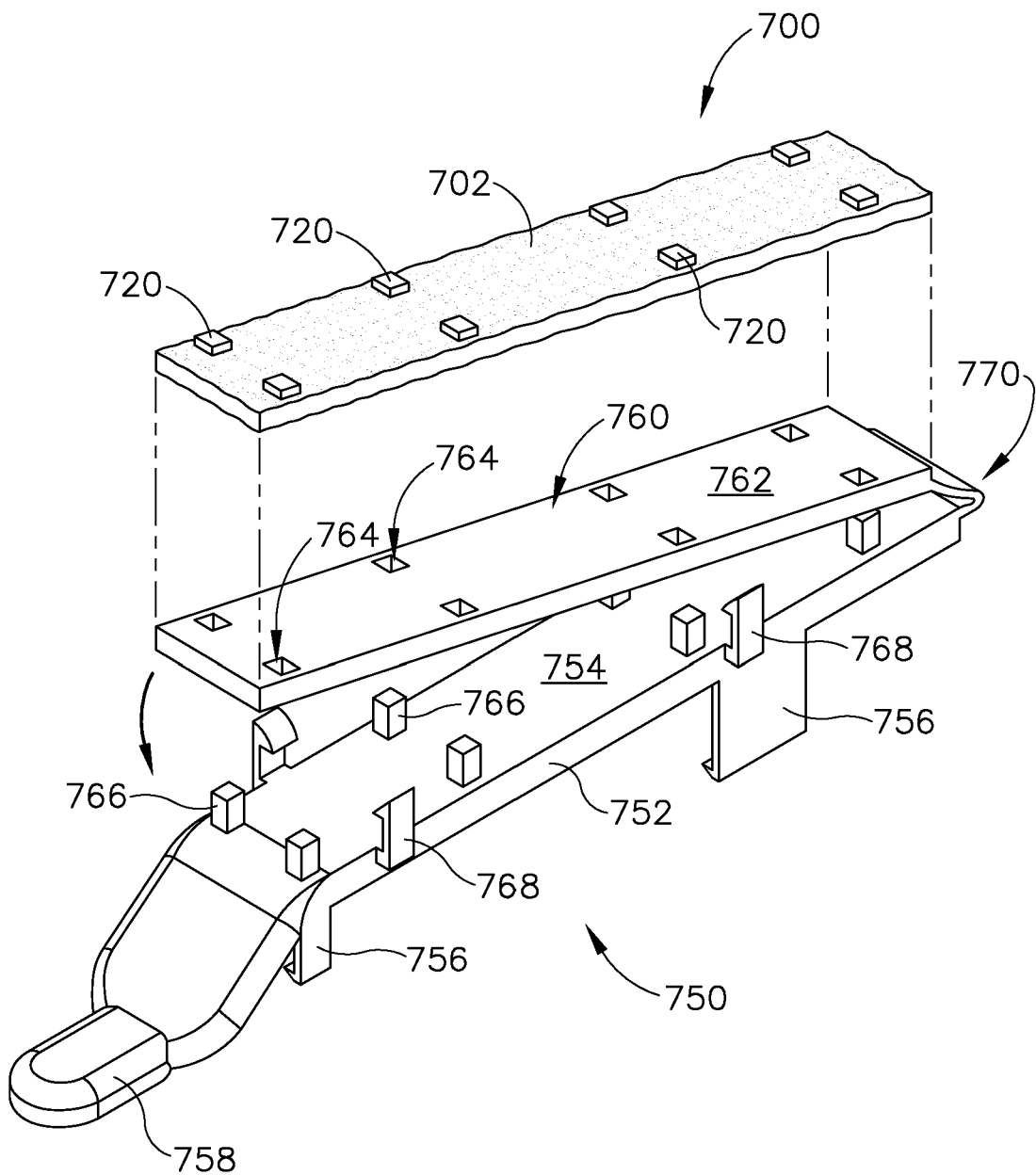
FIG. 23 depicts an exploded perspective view of an exemplary alternative retainer with a buttress positioned for engagement with an upper portion of the retainer.

Adhesive rods (620) are oriented to extend longitudinally, such that adhesive rods are parallel to each other and parallel to the longitudinal axis defined by staple cartridges (70). Adhesive rods (620) are positioned laterally between lip members (680), such that lip members (680) are configured to maintain the positioning of adhesive rods (620). During an initial stage of applying buttress assembly (600) as shown in FIG. 22A, to deck (674) of staple cartridge (670), adhesive rods (620) are cylindrical in form, each having a substantially circular cross section. Buttress body (602) is then pressed against adhesive rods (520), causing adhesive rods (620) to malleably deform as shown in FIG. 22B. This malleable deformation adheres buttress body (602) to deck (674) of staple cartridge (670). Lip members (680) prevent the material forming adhesive rods (620) from entering or otherwise blocking staple pockets (674) during and after this deformation of adhesive rods (620). With buttress body (602) secured to deck (674) of staple cartridge (670) by malleably deformed adhesive rods (620), the end effector that is equipped with staple cartridge (670) and buttress assembly (600) is ready for use as described herein. It should be understood that, with lip members (680) shielding staple pockets (674) from the adhesive material forming adhesive rods (620), the staples driven from staple cartridge (670) will not pass through the adhesive material when staple cartridge (670) is actuated. It should also be understood that adhesive rods (620) (or adhesive structures that are similar to adhesive rods (620) may be positioned on underside (65) of anvil (60) to secure a buttress body (602) to underside (65) of anvil (60). Such adhesive rods (620) may be laterally positioned between longitudinally extending rows of staple forming pockets (64).

d. Discrete Regions of Malleable Polymer Adhesive with Retainer Having Adhesive Driving Features FIG. 23 shows an exemplary alternative buttress assembly (700) with an exemplary alternative retainer (750). Buttress assembly (700) of this example comprises a buttress body (702) and a plurality of discretely formed adhesive regions (720). Buttress body (702) may be configured and operable just like buttress body (102) described above. Adhesive regions (720) may comprise any of the various adhesive materials referred to herein, including but not limited to any of the various absorbable malleable polymer compositions. In the present example, adhesive regions (720) are square shaped, though it should be understood that adhesive regions (720) may have any other suitable configuration.

Retainer (750) comprises a base member (752) having an upper surface (754), a plurality of latches (756), and a distally projecting tongue (758) that is configured to facilitate grasping and manipulation of retainer (750). Retainer (750) also includes an upper member (760) that is secured to base member (752) by a living hinge (770). Upper member (760) has an upper surface (762) that is configured to engage buttress body (702). A plurality of openings (764) are formed through upper member (760). Openings (764) are configured and arranged to correspond with the configuration and arrangement of adhesive regions (720) when buttress assembly (700) is laid over upper surface (762). A plurality of rigid posts (766) extend upwardly from upper surface (754) of base member (752). Posts (766) are configured and arranged to correspond with the configuration and arrangement of openings (764) and adhesive regions (720).

Figure 24:
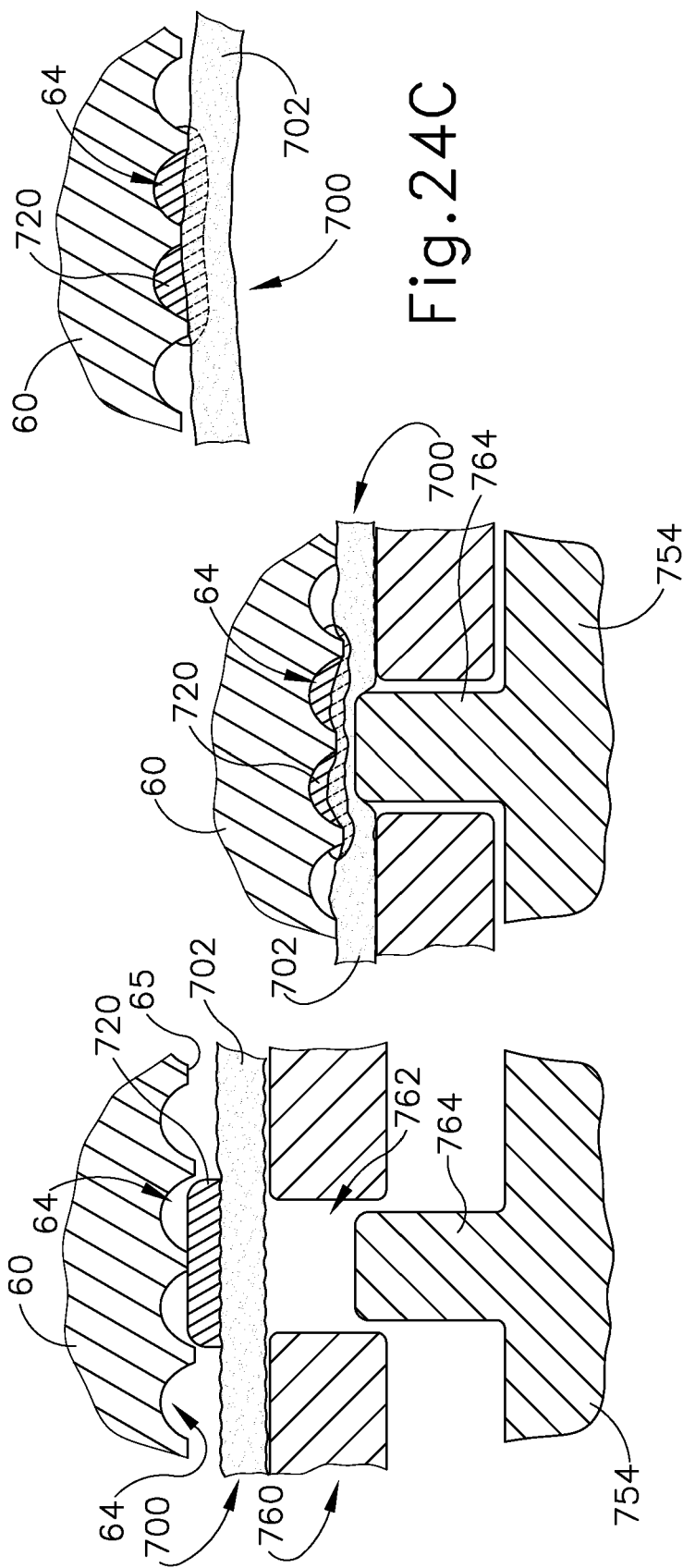
FIG. 24A depicts a cross-sectional view of the retainer and buttress of FIG. 23, with an adhesive portion of the buttress positioned to contact the anvil of the end effector of FIG. 3, and with a post of the retainer spaced away from the buttress.
FIG. 24B depicts a cross-sectional view of the retainer and buttress of FIG. 23, with the post of the retainer driving the adhesive portion of the buttress into the anvil.
FIG. 24C depicts a cross-sectional view of the buttress of FIG. 23 adhered to the anvil of the end effector of FIG. 3, with the retainer removed.

It should be understood that retainer (750) may be removably secured to end effector (40) in a manner similar to retainer (300) described above, with latches (756) releasably engaging lower jaw (50). At such a stage, upper member (760) is spaced away from upper surface (754) of base member (752) due to a resilient bias imposed by living hinge (770). Retainer (750) may thus be configured as shown in FIG. 24A, where anvil (60) is brought into initial contact with buttress assembly (700). As shown, an adhesive region (720) of buttress assembly (700) is positioned directly under a pair of staple forming pockets (64). Alternatively, adhesive region (720) may be positioned under some other feature of underside (65) of anvil (60). The resilient bias provided by living hinge (770) ensures that adhesive region (720) contacts the appropriate region of underside (65) of anvil (60) before anvil (60) reaches a fully closed position. The resilient bias provided by living hinge (770) may also provide and maintain a minimum consistent pressure during the closure of anvil (60) to enhance the attachment of adhesive region (720) to underside (65) of anvil (60).

As anvil (60) is driven further toward the closed position, anvil (60) bears down on adhesive region (720) and upper member (760), thereby causing upper member (760) to pivot toward base member (752). As upper member (760) pivots toward base member (752), post (764) passes through opening (762). The height of post (764) is greater than the vertical thickness of upper member (760), such that the top of post (764) protrudes above upper surface (762) of upper member (760) when upper member (760) is driven downwardly into apposition with upper surface (754) of base member (752). The protruding top of post (764) provides an opposing force against the underside of buttress body (702), in the region beneath adhesive region (720). Adhesive region (720) is thus compressed between underside (65) of anvil (60) and the region of buttress body (702) just above the top of post (764). This compression results in malleable deformation of adhesive region (720), such that the material forming adhesive region takes the form of the corresponding staple forming pockets (64), as shown in FIG. 24B.

Figure 25:
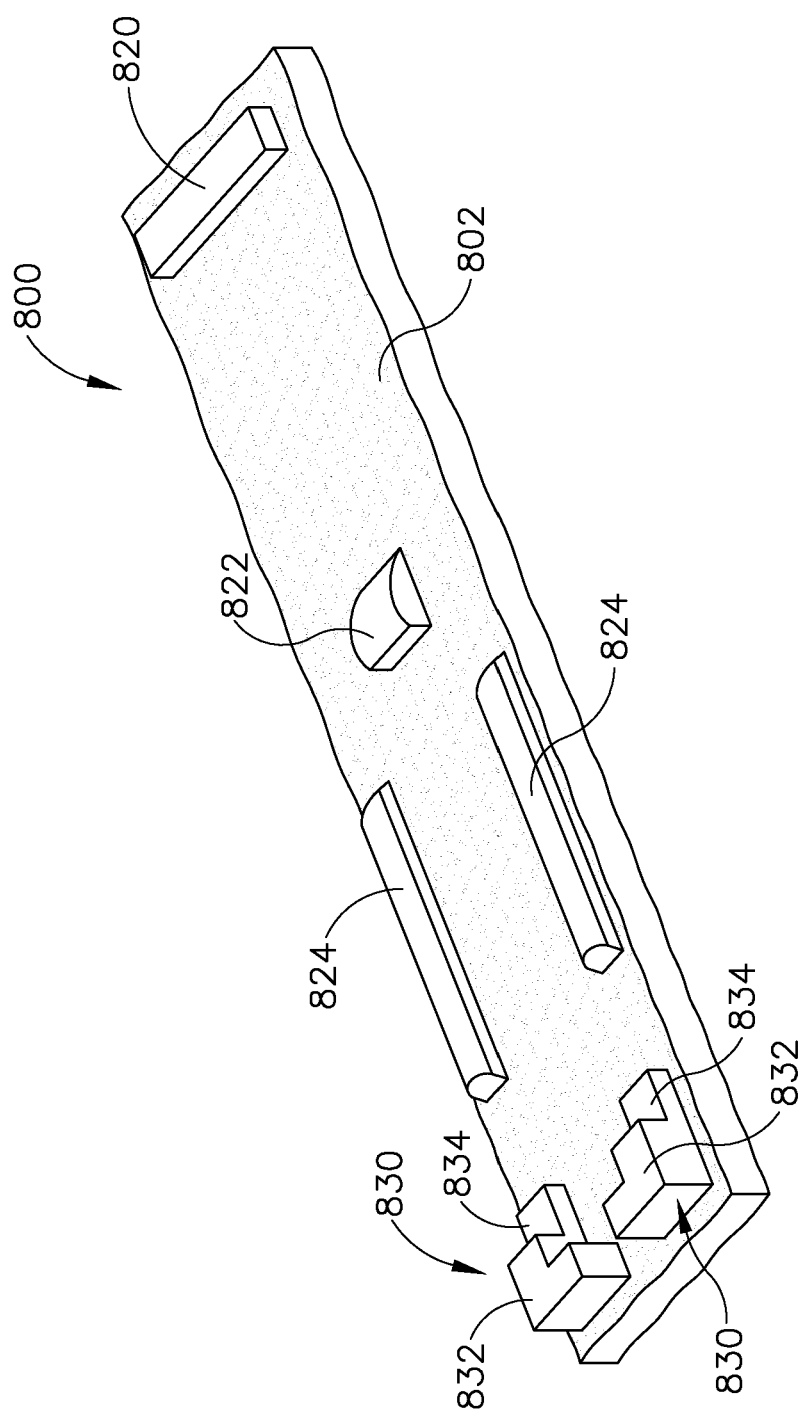
FIG. 25 depicts a perspective view of an exemplary alternative buttress assembly.

It should be understood that the foregoing actions may take place at every post (764) and adhesive region (720), such that the adhesive regions (720) together adhere buttress assembly (700) to underside (65) of anvil (60). At this stage, latches (768) of retainer (750) may secure upper member (760) into apposition with base member (752), facilitating removal of retainer (750) from end effector (40). Buttress assembly (700) is left adhered to underside (65) of anvil (60) as shown in FIG. 24C, such that end effector (40) is then ready for use.

e. Buttress Assembly with Malleable Polymer Adhesive in Asymmetric Geometries and Thicknesses FIG. 25 shows an exemplary buttress assembly (800) comprising a buttress body (802) and a plurality of adhesive regions (820, 822, 824, 830). Buttress body (802) may be configured and operable just like buttress body (102) described above. Adhesive regions (820, 822, 824, 830) may comprise any of the various adhesive materials referred to herein, including but not limited to any of the various absorbable malleable polymer compositions. A first adhesive region (820) extends laterally along a proximal portion of buttress body (802), spanning substantially the full width of buttress body (802). A second adhesive region (822) is located near the longitudinal and lateral center of buttress body (802). Third and fourth adhesive regions (824) extend longitudinally along each lateral side of buttress body (802). Fifth and sixth adhesive regions (830) are located at the distal end of buttress body (802), at the corners. Each adhesive region (830) includes a thick portion (832) and a thin portion (834). It should be understood that any of the other adhesive regions (822, 824, 830) may also have thick and thin portions. In addition or in the alternative, some adhesive regions (820, 822, 824, 830) may be thicker than other adhesive regions (820, 822, 824, 830). In addition or in the alternative, some adhesive regions (820, 822, 824, 830) may have a greater density than other adhesive regions (820, 822, 824, 830). Similarly, any one of the adhesive regions (820, 822, 824, 830) may have varying intra-region density.

It should be understood that providing varying thicknesses and/or densities among and/or within adhesive regions (820, 822, 824, 830) may result in a non-homogenous pressure distribution on adhesive regions (820, 822, 824, 830) when buttress assembly (800) is pressed against deck (73) of staple cartridge (70) or underside (65) of anvil (60). Such non-homogenous pressure distribution may maximize bonding in certain areas while letting other areas have less deformation and adhesion. Other suitable ways in which a buttress assembly may be formed with varying thicknesses and/or densities among and/or within adhesive regions will be apparent to those of ordinary skill in the art in view of the teachings herein.

D. Low Inherent Viscosity Bioabsorbable Polymer Adhesive

In some instances, it may be desirable to provide one or more adhesive layers (104, 106) with a bioabsorbable polymer adhesive having a low inherent viscosity (IV). The below examples include various exemplary configurations through which a bioabsorbable polymer adhesive having a low inherent viscosity (IV) may be combined with a buttress body (102). In the present example, it is contemplated that the adhesive material comprises a synthetic based polymer such as those referred to herein. However, it should also be understood that naturally based polymers may be incorporated with the below teachings.

One example of a suitable adhesive copolymer having a low inherent viscosity (IV) is a 65/35 composition of caprolactone and glycolide (PCL/PGA) having low crystallinity, with an inherent viscosity (IV) in the range of about 0.8 dL/g to about 1.0 dL/g. A 65/35 composition of caprolactone and glycolide (PCL/PGA) with a low inherent viscosity (IV) and having a molecular weight near or equal to that of Monocryl (which has a 75/25 composition of caprolactone and glycolide (PCL/PGA)) may also provide suitable adhesive properties. Another example of a suitable adhesive copolymer having a low inherent viscosity (IV) is a composition of caprolactone and glycolide (PCL/PGA) with an inherent viscosity (IV) in the range of 0.2 dL/g to 1.0 dL/g. Another example of a suitable adhesive copolymer having a low inherent viscosity (IV) is a composition of trimethylene carbonate and caprolactone (TMC/PCL) with an inherent viscosity (IV) in the range of 0.3 dL/g to 1.0 dL/g, or more particularly in the range of 0.5 dL/g to 1.0 dL/g. Another suitable adhesive having a low inherent viscosity (IV) is caprolactone (PCL) with an inherent viscosity (IV) in the range of 0.2 dL/g to 0.9 dL/g.

Inherent viscosity (IV) reflects a measurement of molecular size. It is based on the flow time of a polymer solution through small capillary channels over time. The inherent viscosity (IV) and molecular weight of a polymer are related, but that relational agreement is different for each copolymer composition. For instance, the correlation of inherent viscosity (IV) to molecular weight may be logarithmic with only a small midsection of the curve being linear. This logarithmic correlation may differ as the copolymer composition differs. It is not necessarily required to have a low molecular weight copolymer in order to manifest adhesive and malleable properties. Low molecular weight copolymers may also have shortened degradation cycles and reduced structural strength. The ideal adhesion film or adhesive substrate to use in adhesive layer (104, 106) would have higher molecular weight and low inherent viscosity (IV) to be both strong and adhesive. By way of example only, a suitable adhesive material having a low inherent viscosity (IV) may have a molecular weight in the range of 11,000 g/mol to 30,000 g/mol. The molecular weight may be higher in cases where the inherent viscosity (IV) is particularly low. For instance, a suitable adhesive material may comprise a 50/50 composition of caprolactone and glycolide (PCL/PGA) with an inherent viscosity of about 0.2 dL/g and a molecular weight of about 83,000 g/mol.

E. Low Glass Transition Temperature Bioabsorbable Polymer Adhesive

In some instances, it may be desirable to provide one or more adhesive layers (104, 106) with a bioabsorbable polymer adhesive having a low glass transition temperature (Tg). The below examples include various exemplary configurations through which a bioabsorbable polymer adhesive having a low glass transition temperature (Tg) may be combined with a buttress body (102). In the present example, it is contemplated that the adhesive material comprises a synthetic based polymer such as those referred to herein. However, it should also be understood that naturally based polymers may be incorporated with the below teachings.

Glass transition temperature (Tg) is the temperature at which the mechanical properties of a copolymer change dramatically from a flowable adhesive to a brittle plastic. The glass transition temperature (Tg) is lower than the melting point of the crystalline form of the same copolymer. The glass transition temperature (Tg) may be indicative of how the polymer behaves under ambient conditions. The melting temperature (Tm) may be referred to as the "first-order transition," which is where the polymer changes state from solid to liquid. Crystalline polymers have a true melting point, which is the temperature at which the crystallites melt and the total mass of plastic becomes amorphous. Amorphous polymers do not have a true melting point, but they do have a first-order transition where their mechanical behavior transitions from a rubbery nature to viscous rubbery flow. Suitable polymers for use in forming adhesive layer (102, 104) may have a percent of crystallinity making them behave both amorphically and crystally. The glass transition temperature (Tg) can be effected by composition, polymer chain configuration and stiffness, molecular weight, viscosity, shear modulus, heat capacity, thermal expansion, cross-linking and other factors. It is therefore possible to have a relatively low glass transition temperature (Tg) material composition that does not always correspond to low molecular weight or low inherent viscosity (IV).

In versions where the adhesive material comprises a composition of caprolactone and glycolide (PCL/PGA), the glass transition temperature (Tg) may be below about 0° C., and more particularly below about −20° C. One specific example of a suitable adhesive copolymer having a low glass transition temperature (Tg) is a 65/35 composition of caprolactone and glycolide (PCL/PGA), with a low inherent viscosity (IV) and low crystallinity, having a glass transition temperature (Tg) of less than about −35° C. Another specific example of a suitable adhesive copolymer having a low glass transition temperature (Tg) is a 50/50 composition of caprolactone and glycolide (PCL/PGA), with a low inherent viscosity (IV) and low crystallinity, having a glass transition temperature (Tg) of less than about −19° C.

Another example of a suitable adhesive copolymer having a low glass transition temperature (Tg) is a 50/50 composition of trimethylene carbonate and caprolactone (TMC/PCL), with a low inherent viscosity (IV) and low crystallinity, having a glass transition temperature (Tg) below about 0° C. and more particularly below about −20° C. In versions where the adhesive material comprises a composition of lactide and caprolactone (PLA/PCL), the glass transition temperature (Tg) may be below about 4° C., and more particularly below about −10° C. In versions where the adhesive material comprises caprolactone (PCL), the glass transition temperature (Tg) may be below about −60° C. In versions where the adhesive material comprises polyethylene glycol (PEG), the glass transition temperature (Tg) may be below about −35° C. Yet another example of a suitable adhesive copolymer having a low glass transition temperature (Tg) is a 50/50 composition of caprolactone and glycolide (PCL/PGA), with a low inherent viscosity (IV) and low crystallinity.

F. Biologically Derived Extracellular Matrix with Infused Viscous Absorbable Copolymer In some instances, it may be desirable to provide a biologically derived extracellular matrix (ECM) as buttress body (102) with an infused viscous absorbable copolymer as an adhesive layer (104, 106) on upper or lower surfaces of buttress body (102). The below examples include various exemplary configurations through which a buttress assembly (100) may be formed by a combination of a biologically derived extracellular matrix (ECM) with one or more infused viscous absorbable copolymer adhesive materials. In the present example, it is contemplated that the adhesive material comprises a natural based polymer such as those referred to herein. However, it should also be understood that synthetic based polymers may be incorporated with the below teachings.

Figure 26:
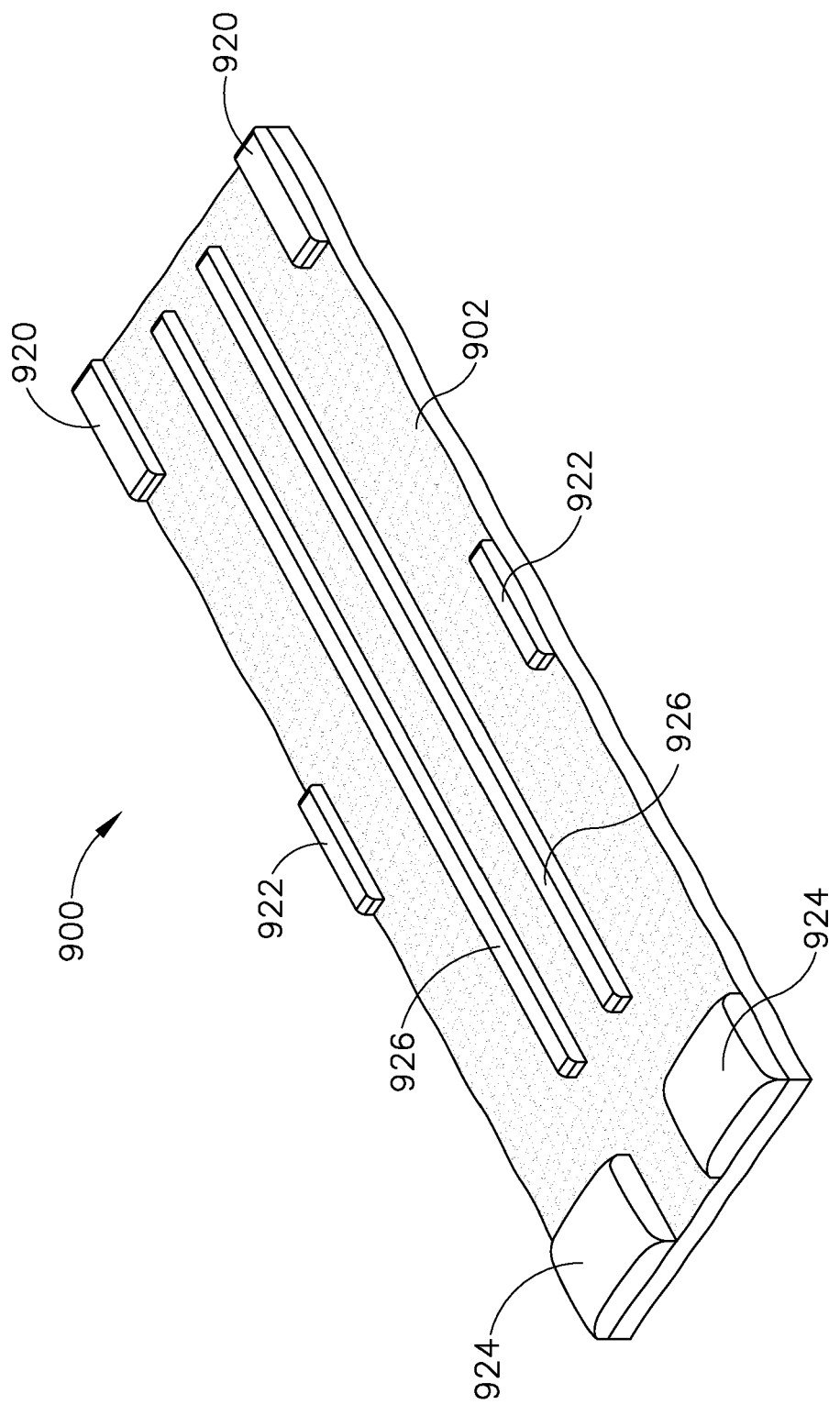
FIG. 26 depicts a perspective view of another exemplary alternative buttress assembly.
Figure 27:
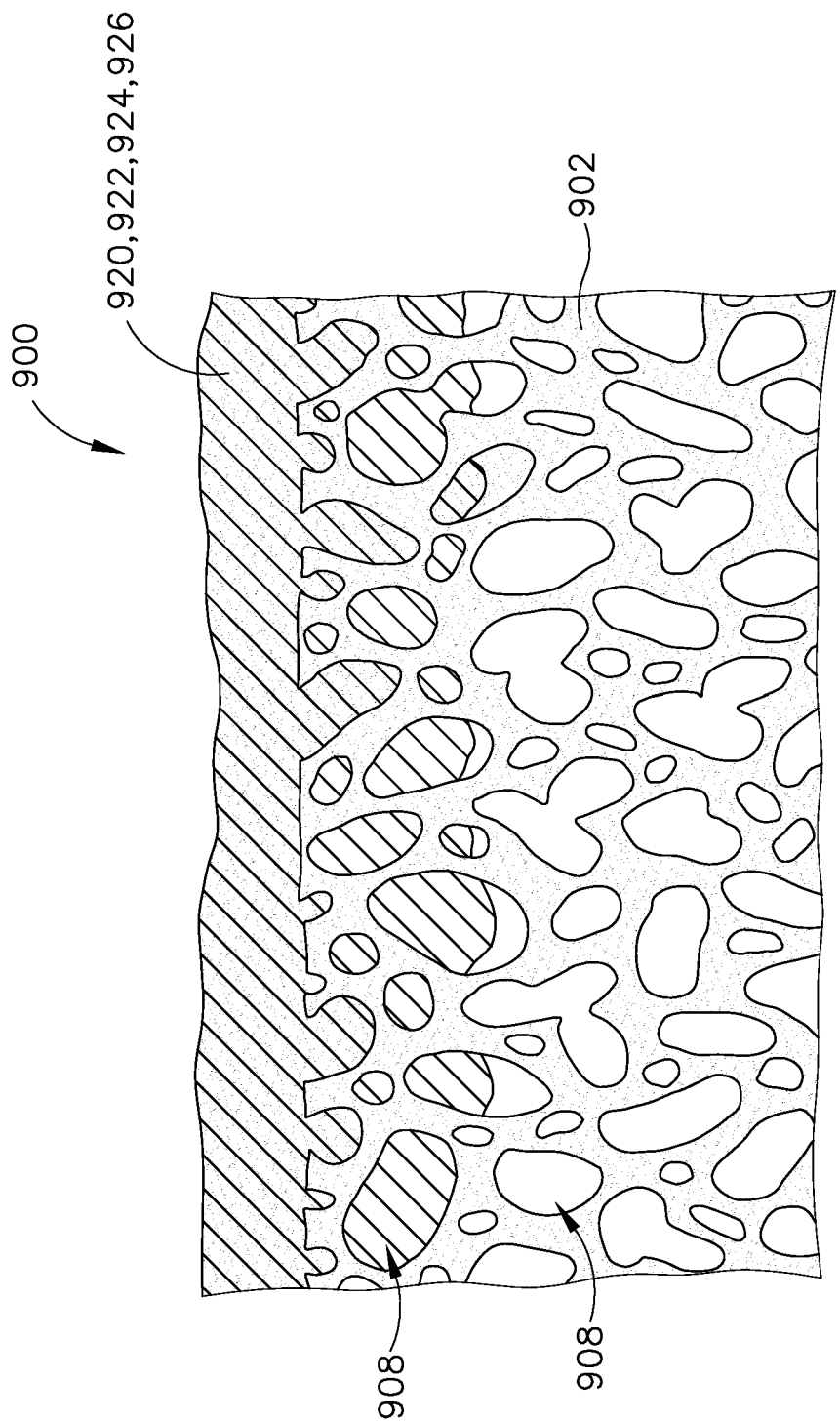
FIG. 27 depicts a cross-sectional view of a region of the buttress assembly of FIG. 26.
Figure 28:
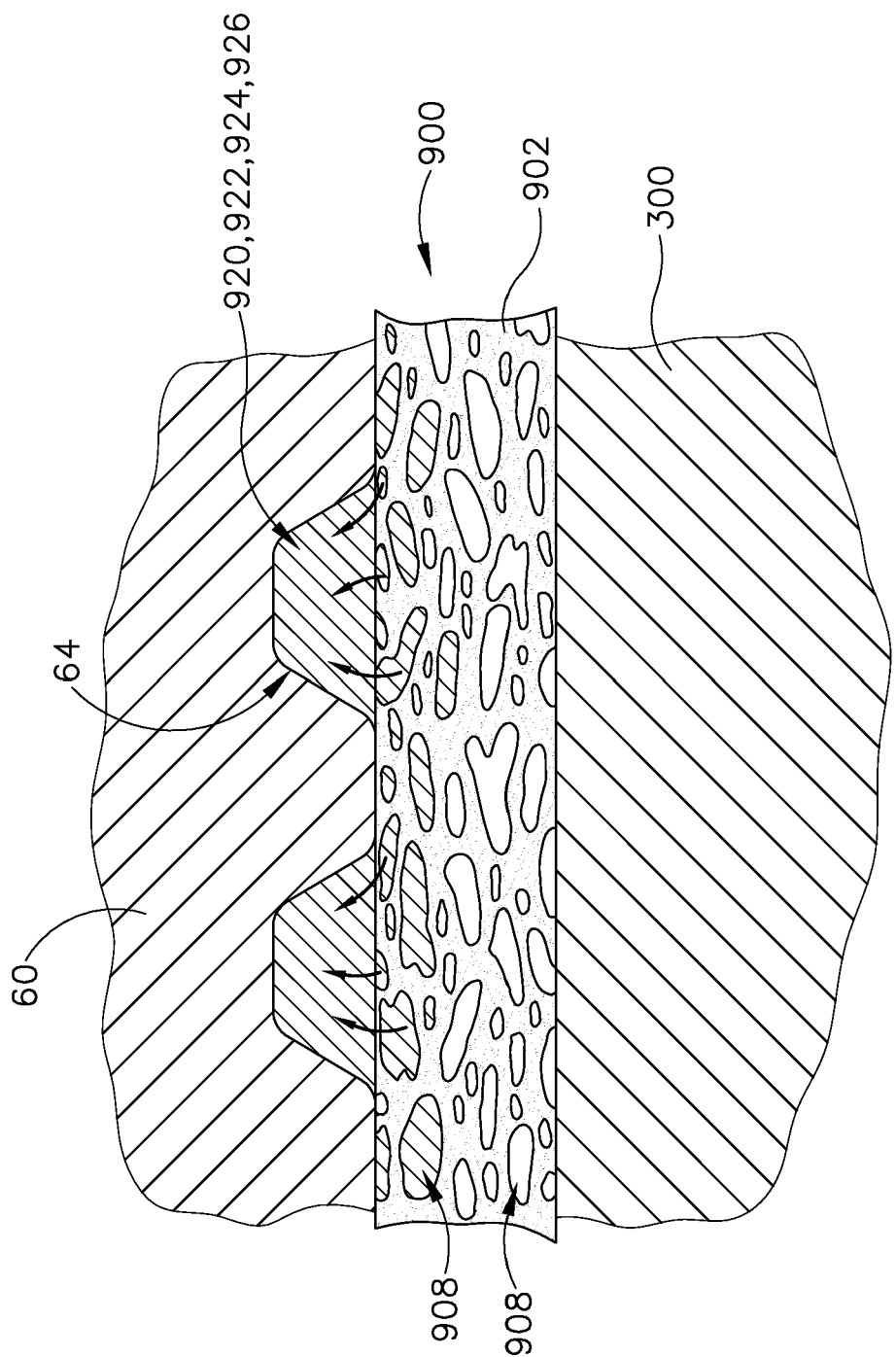
FIG. 28 depicts a cross-sectional view of a region of the buttress assembly of FIG. 26 being compressed against the anvil of the end effector of FIG. 3.

FIGS. 26-28 show an exemplary buttress assembly (900) that comprises a buttress body (902) and a plurality of discretely formed adhesive regions (920, 922, 924, 926). Buttress body (902) may be configured and operable just like buttress body (102) described above. Buttress body (902) of this particular example comprises a biologically derived extracellular matrix (ECM) such as collagen. Adhesive regions (920, 922, 924, 926) may comprise any of the various adhesive materials referred to herein. A first pair of proximal adhesive regions (920) are positioned at respective proximal corners of buttress body (902). A second pair of lateral adhesive region (922) are located near the longitudinal and lateral center of buttress body (902). A third pair of adhesive regions (924) are positioned at respective proximal corners of buttress body (902). A fourth pair of adhesive regions (926) extend longitudinally along the lateral mid-region of buttress body (902), such that adhesive regions (926) are positioned to run alongside channel (62) of anvil (60) or channel (72) of staple cartridge (70). While adhesive regions (920, 922, 924, 926) are provided in a particular pattern in this example, it should be understood that buttress assembly (900) may instead have adhesive regions in any other suitable pattern. It should also be understood that buttress assembly (900) may have a single layer of adhesive material spanning along the full surface of buttress body (902), without having discretely formed adhesive regions. Other suitable configurations will be apparent to those of ordinary skill in the art in view of the teachings herein.

FIG. 27 shows how buttress body (902) provides a lattice defining a plurality of cells (908). Due to the presence of cells (908) and the porous nature of buttress body (902), some of the adhesive material forming adhesive regions (920, 922, 924, 926) has entered some of those cells (908), thereby partially infusing buttress body (902) with the adhesive material. In other words, buttress body (902) acts like a sponge absorbing the adhesive material, allowing the adhesive material to deform, surround, and essentially grab hold of the lattice connections within buttress body (902).

In some instances, the adhesive material is initially applied to buttress body (902) when the adhesive material is in a relatively high viscous form. Buttress assembly (900) is then heated to increase the viscosity of the adhesive material, causing the adhesive material to enter some of the cells (908) of buttress body (902). Buttress assembly (900) is then cooled or allowed to cool, causing the viscosity of the adhesive material to increase back to its previous state. Buttress assembly (900) may then be heated again as buttress assembly (900) is being applied to end effector (40) as described in greater detail below. In some other versions, the adhesive material already has a low enough viscosity to enter cells (908) when the adhesive material is applied, without requiring the adhesive material to be heated. In other words, the adhesive material may wick into cells (908) of buttress body (902). In some such versions, a protective film (e.g., polytetrafluoroethylene (PTFE)) may be applied over the adhesive material to protect and/or contain the adhesive material before buttress assembly (900) is applied to end effector (900). Other suitable ways in which buttress assembly (900) may be formed and provided will be apparent to those of ordinary skill in the art in view of the teachings herein.

FIG. 28 shows buttress assembly (900) being compressed between retainer (300) and anvil (60). As shown, this compression crushes the lattice structure of buttress body (902), collapsing cells (908) and thereby driving adhesive material out of buttress body (902) and into staple forming pockets (64) (and/or into other surface features of underside (65)). This compression may be provided by closing anvil (60) against buttress assembly (900) and retainer (300) as described above. When anvil (60) is returned to the open position, the adhesive material in staple forming pockets (64) (and/or in other surface features of underside (65)) adheres buttress assembly (900) to underside (65), such that end effector (40) is loaded with buttress assembly (900) and is ready for use. In some instances, retainer (300) and/or buttress assembly (900) may be heated just before buttress assembly (900) is compressed between retainer (300) and anvil (60). Such heating may increase the viscosity of the adhesive material, thereby promoting migration of the adhesive material into features of underside (65) and further thereby reducing the compression force required to urge the adhesive material into the features of underside (65).

Figure 29:
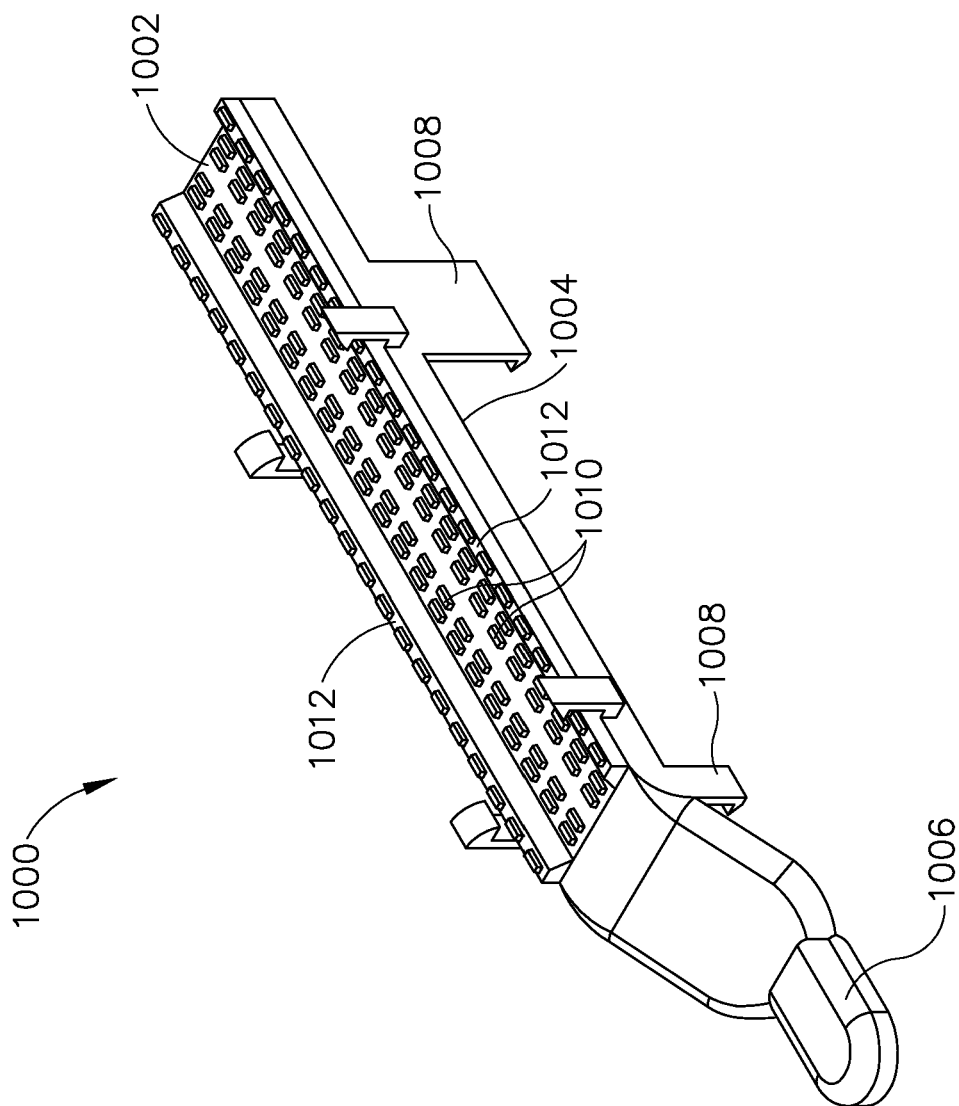
FIG. 29 depicts a perspective view of an exemplary alternative retainer.

FIG. 29 shows an exemplary alternative retainer (1000) that may be used with a buttress assembly such as buttress assembly (900). Retainer (1000) of this example comprises an upper side (1002), an underside (1004), a distally projecting tongue (1006), and a set of resilient latches (1008). It should be understood that underside (1004), tongue (1006), and latches (1008) may be configured and operable just like underside (304), tongue (306), and latches (308) described above. Upper side (1002) of this example differs from upper side (302) in that upper side (1002) includes an array of upwardly protruding projections (1010) and a pair of longitudinally extending side rails (1012). Projections (1010) are configured to provide focused pressure to regions of buttress assembly (900) at regions corresponding to staple forming pockets (64) (and/or into other surface features of underside (65)), thereby further promoting exit of the adhesive material from buttress body (902) into staple forming pockets (64) (and/or into other surface features of underside (65)). Side rails (1012) are configured to contain adhesive material expelled from buttress body (902), preventing the adhesive material from spilling over the sides of retainer (1000). Other suitable structural variations of retainer (1000) will be apparent to those of ordinary skill in the art in view of the teachings herein.

Figure 30:
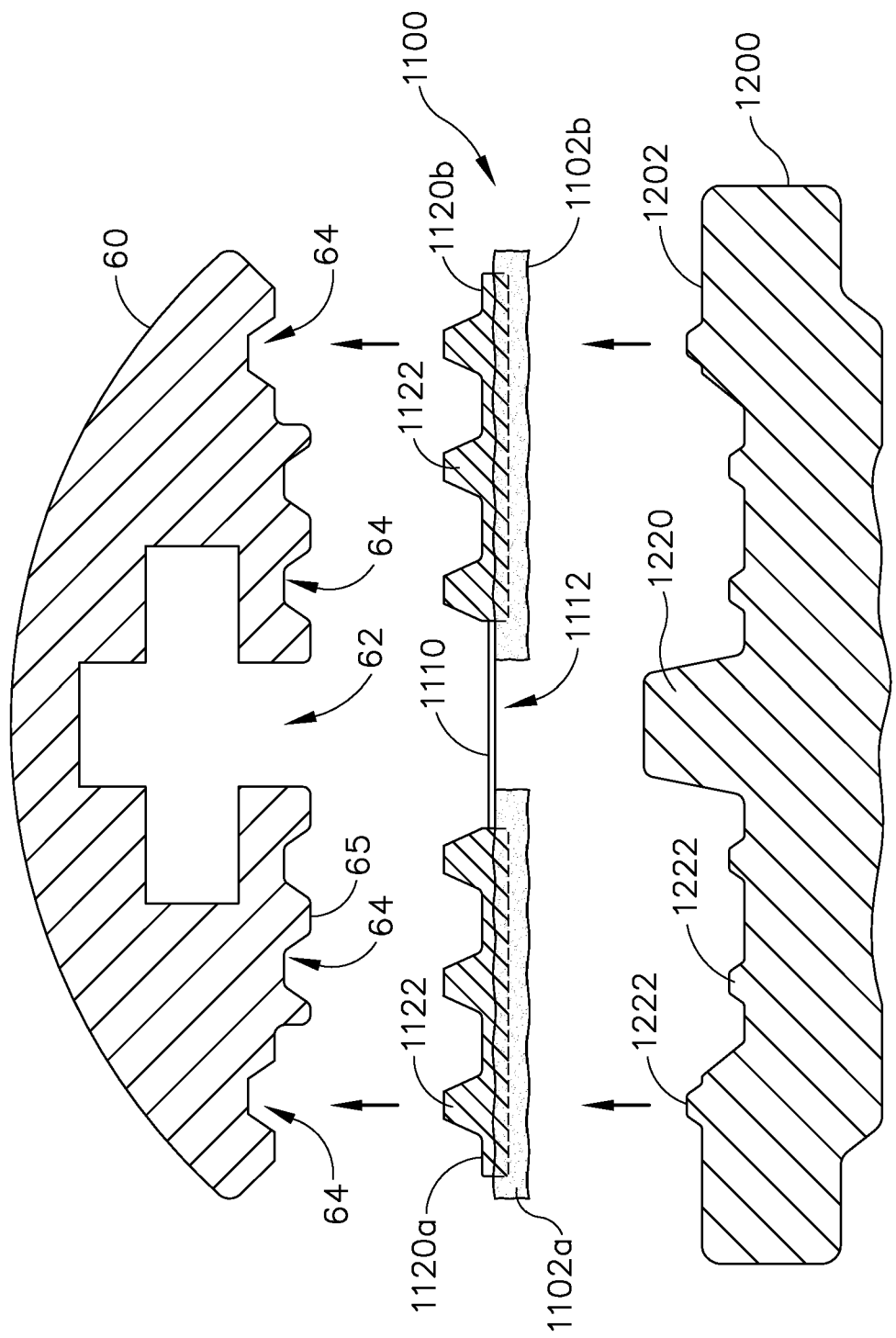
FIG. 30 depicts an exploded cross-sectional view of an exemplary buttress assembly between an exemplary retainer and the anvil of the end effector of FIG. 3.

FIG. 30 shows another exemplary buttress assembly (1100) and retainer (1200). Buttress assembly (1100) of this example comprises a pair of buttress body sections (1102a, 1102b) that are joined by one or more tethers (1110) that span across a gap (1112) defined between buttress body sections (1102a, 1102b). Gap (1112) extends longitudinally and is sized to complement channels (62, 72) of anvil (60) and staple cartridge (70). Each buttress body section (1102a, 1102b) comprises a biologically derived extracellular matrix (ECM) such as collagen, such that each buttress body section (1102a, 1102b) has a lattice structure defining a plurality of cells (not shown). Buttress assembly (1100) further comprises adhesive layer sections (1120a, 1120b) extending along respective body sections (1102a, 1102b). The adhesive material forming adhesive layer sections (1120a, 1120b) may be formulated just like the adhesive material forming adhesive regions (920, 922, 924, 926) described above. Adhesive layer sections (1102a, 1102b) each include a plurality of upwardly extending projections (1122). These projections are configured and positioned to correspond with staple forming pockets (64) on underside (65) of anvil (60).

Retainer (1200) of the present example has an upper surface (1202) that includes an upwardly projecting rib (1220) and a plurality of upwardly extending projections (1222). Rib (1220) extends longitudinally and is sized to complement channel (62) of anvil (60). As anvil (60) is driven to a closed position to compress buttress assembly (1100) against upper surface (1202), rib (1220) may enter channel (62) and break tethers (1100). Rib (1220) may also ensure proper lateral alignment of retainer (1200) and buttress assembly (1100) with anvil (60). Various suitable forms that rib (1220) may take will be apparent to those of ordinary skill in the art in view of the teachings herein. In some versions, rib (1220) is omitted. Projections (1222) are configured and positioned to correspond with projections (1122), staple forming pockets (64) underside (65) of anvil (60). Projections (1122, 1222) are configured to cooperate to provide focused pressure to regions of buttress assembly (1100) at regions corresponding to staple forming pockets (64) of underside (65) when anvil (60) is driven to a closed position against buttress assembly (1100) and retainer (1200), thereby further promoting exit of the adhesive material from buttress bodies (1102a, 1102b) into staple forming pockets (64) of underside (65). Other suitable structural variations of buttress assembly (1100) and retainer (1200) will be apparent to those of ordinary skill in the art in view of the teachings herein.

G. Naturally Derived Bioabsorbable Polymer Gel Adhesive

In some instances, it may be desirable to combine a naturally derived bioabsorbable polymer gel with buttress body (102), in addition to or as an alternative to having one or more adhesive layers (104, 106) on upper or lower surfaces of buttress body (102), to removably secure buttress assembly (100) to deck (73) of staple cartridge (70) or underside (65) of anvil (60). The below examples include various exemplary configurations through which one or more naturally derived bioabsorbable polymer gel adhesive materials may be combined with a buttress body (102) to removably secure buttress assembly (100) to deck (73) of staple cartridge (70) or underside (65) of anvil (60). In the present example, it is contemplated that the adhesive material comprises a natural based polymer such as those referred to herein. However, it should also be understood that synthetic based polymers may be incorporated with the below teachings.

For instance, a naturally derived polymer may be provided in an absorbable polymer solution to create a gel for attachment of buttress assembly (100) to deck (73) of staple cartridge (70) or underside (65) of anvil (60). A bioactive component that is a solid in dry form or a gel in solution form is combined with an absorbable copolymer that does not include suspension of the degradation process until further exposure to water. For instance, dry polymer (powdered) of a water soluble polymer (e.g., carboxymethylcellulose (CMC)) may be mixed with a water soluble liquid such as glycerin. When mixed, it forms a tacky and viscous compound. This compound remains very tacky and will stick to dry surfaces or substances, but it will not stick to wet or hydrated substances. When this compound comes into contact with water or a wet surface it changes from sticky and tacky to very slippery and lubricious. This compound will also go into complete solution when added to water more rapidly than the dry polymer powder alone. Suitable polymers that may be used in such a composition include (but are not limited to) hyaluronic acid, carboxymethylcellulose (CMC), polyvinyl alcohol, poly vinyl acetate, higher molecular weight polyethylene glycol (PEG) (in solid form), or higher molecular weight polypropylene glycol (in solid form). Suitable liquids that may be used in such a composition include (but are not limited to) glycerin, low molecular weight polyethylene glycol (PEG) (in liquid form), or low molecular weight polypropylene glycol (in liquid form).

In some versions, the adhesive material comprises a viscous cellulose bioabsorbable gel with particulate absorbable materials to increase viscosity for attachment of buttress assembly (100) to deck (73) of staple cartridge (70) or underside (65) of anvil (60). In particular, the adhesive material may comprise a bioabsorbable liquid that has particulates mixed into the fluid to induce a gel-like suspension with highly viscous features for application to buttress body (102) for attachment to deck (73) of staple cartridge (70) or underside (65) of anvil (60).

1. Exemplary Retainer with Lower Adhesive Injection Region

Figure 31:
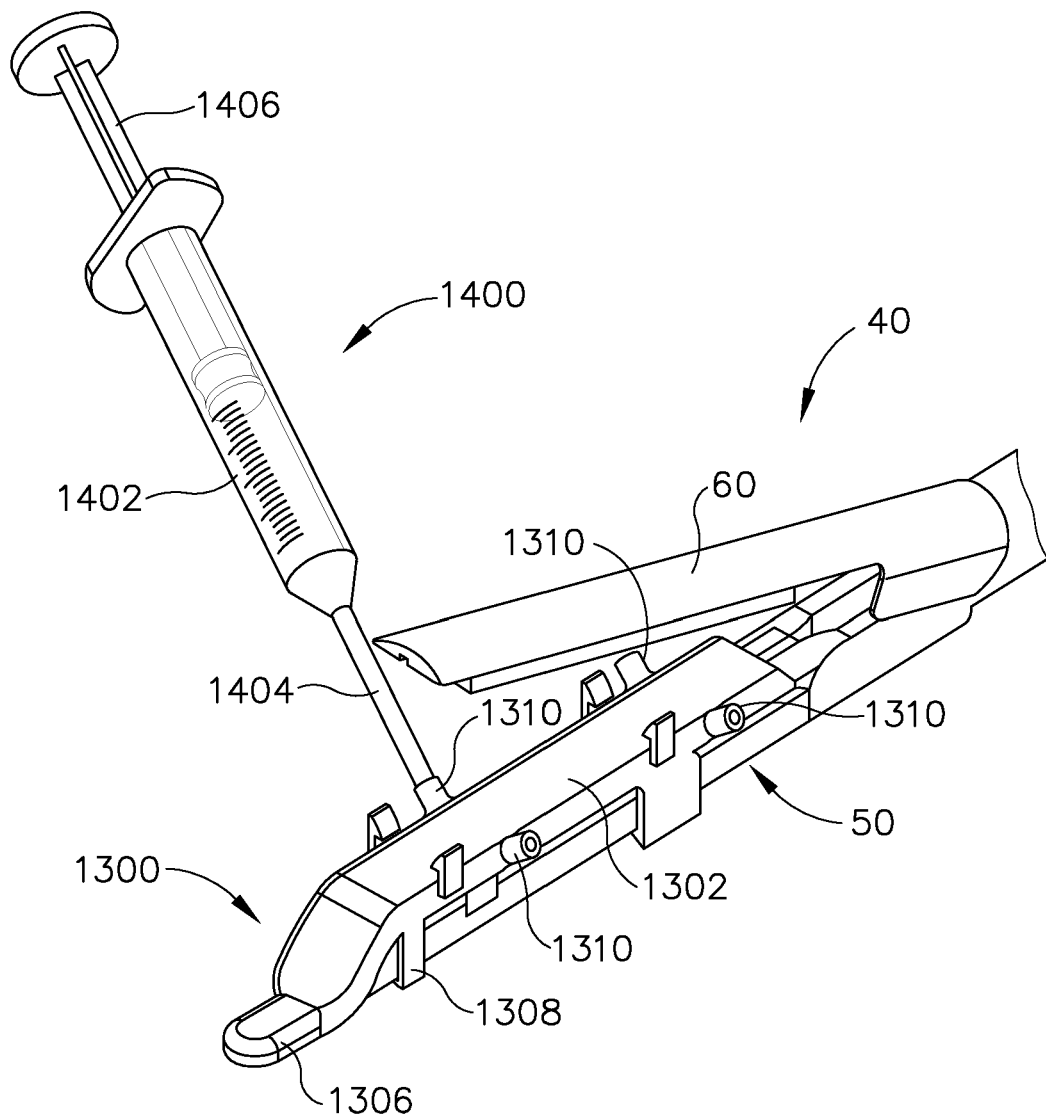
FIG. 31 depicts a perspective view of an exemplary alternative retainer assembly coupled with the end effector of FIG. 3, with a syringe injecting an adhesive material into the retainer assembly, and with the anvil of the end effector in an open position.
Figure 32:
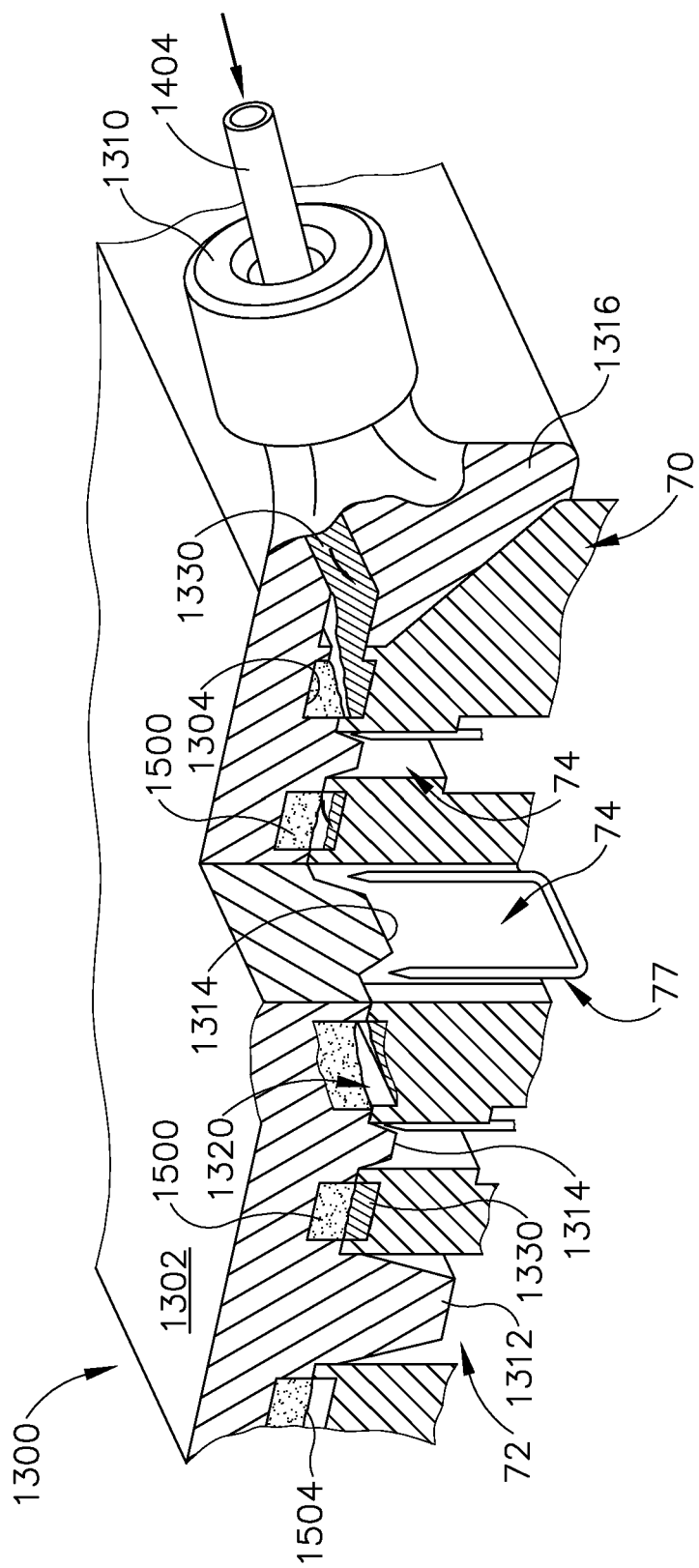
FIG. 32 depicts a cross-sectional view of the retainer assembly and end effector of FIG. 31.

FIGS. 31-32 show an exemplary retainer (1300) that may be used to dispense a polymer adhesive gel (1330) directly at the site of end effector (40) as a buttress body (1500) is being applied to end effector (40). The polymer adhesive gel (1330) is stored and contained in a barrel (1402) of syringe (1400) before dispensation. The gel is communicated by advancing a plunger (1406) of syringe (1400) relative to barrel (1402), which drives the gel through needle (1404). Retainer (1300) of this example comprises an upper side (1302), an underside (1304), a distally projecting tongue (1306), a set of resilient latches (1308), and a set of injection ports (1310). It should be understood that upper side (1302), tongue (1306), and latches (1308) may be configured and operable just like upper side (302), tongue (306), and latches (308) described above. Thus, retainer (1300) may be removably secured to lower jaw (50) to apply buttress body (1500) to deck (73) of staple cartridge. Buttress body (1500) of this example may be configured like any other buttress body described herein.

As best seen in FIG. 32, underside (1304) of retainer (1300) includes a plurality of downwardly extending projections (1312, 1314) and outer rails (1316). Projection (1312) is positioned and configured to extend into channel (72) of staple cartridge (70). Projections (1314) are positioned and configured to extend into staple pockets (74) of staple cartridge (70). Outer rails (1316) engage the perimeter of deck (73) of staple cartridge (70). Projections (1312, 1314) and rails (1316) serve as standoff features to provide a gap (1320) between the underside (1504) of buttress body (1500) and deck (73) of cartridge (70). Ports (1310) are in fluid communication with gap (1320). Thus, with needle (1404) inserted into port (1310), adhesive gel (1330) may be injected into gap (1320) by advancing plunger (1406) relative to barrel (1402). Projections (1312, 1314) may prevent adhesive gel (1330) from entering channel (72) and staple pockets (74), respectively as adhesive gel (1330) is injected into gap (1320). Similarly, outer rails (1316) may prevent adhesive gel (1330) from escaping at the perimeter of deck (73) as adhesive gel (1330) is injected into gap (1320). In some versions, each port (1310) includes a self-sealing septum (not shown) that prevents adhesive gel (1330) from escaping through port (1310) during and after injection of adhesive gel (1330).

In some versions, underside (1304) of retainer (1300) is divided into four quadrants. In some such versions, these quadrants are fluidly isolated from each other, resulting in four separate gaps (1320). In such versions, needle (1404) may be inserted into each port (1310) to separately fill each gap (1320) with adhesive gel (1330). In some other versions, at least two of the quadrants are in fluid communication with each other (e.g., the two quadrants on each side of projection (1312)), such that the operator may use either two or more than two ports (1310) to fill gap (1320) with adhesive gel (1330). Of course, any other suitable number of ports (1310) and separate sections of gap (1320) may be provided. Once a sufficient amount of adhesive gel (1330) has been injected, retainer (1300) may be held in place for any desired about of time to allow adhesive gel (1330) to cure, set up, or otherwise change state to a point where adhesive gel (1330) will sufficiently secure buttress body (1500) to deck (73) after retainer (1300) is removed. Alternatively, adhesive gel (1330) may already be in a state where adhesive gel (1330) will sufficiently secure buttress body (1500) to deck (73) after retainer (1300) is removed, without requiring retainer (1300) to be kept in place for a significant period of time. In either case, once retainer (1300) is removed from end effector (40), the buttress assembly formed by adhesive gel (1330) and buttress body (1500) will be secured to deck (73), such that loaded end effector (40) will be ready for use.

2. Exemplary Retainer with Upper Adhesive Injection Region

Figure 33:
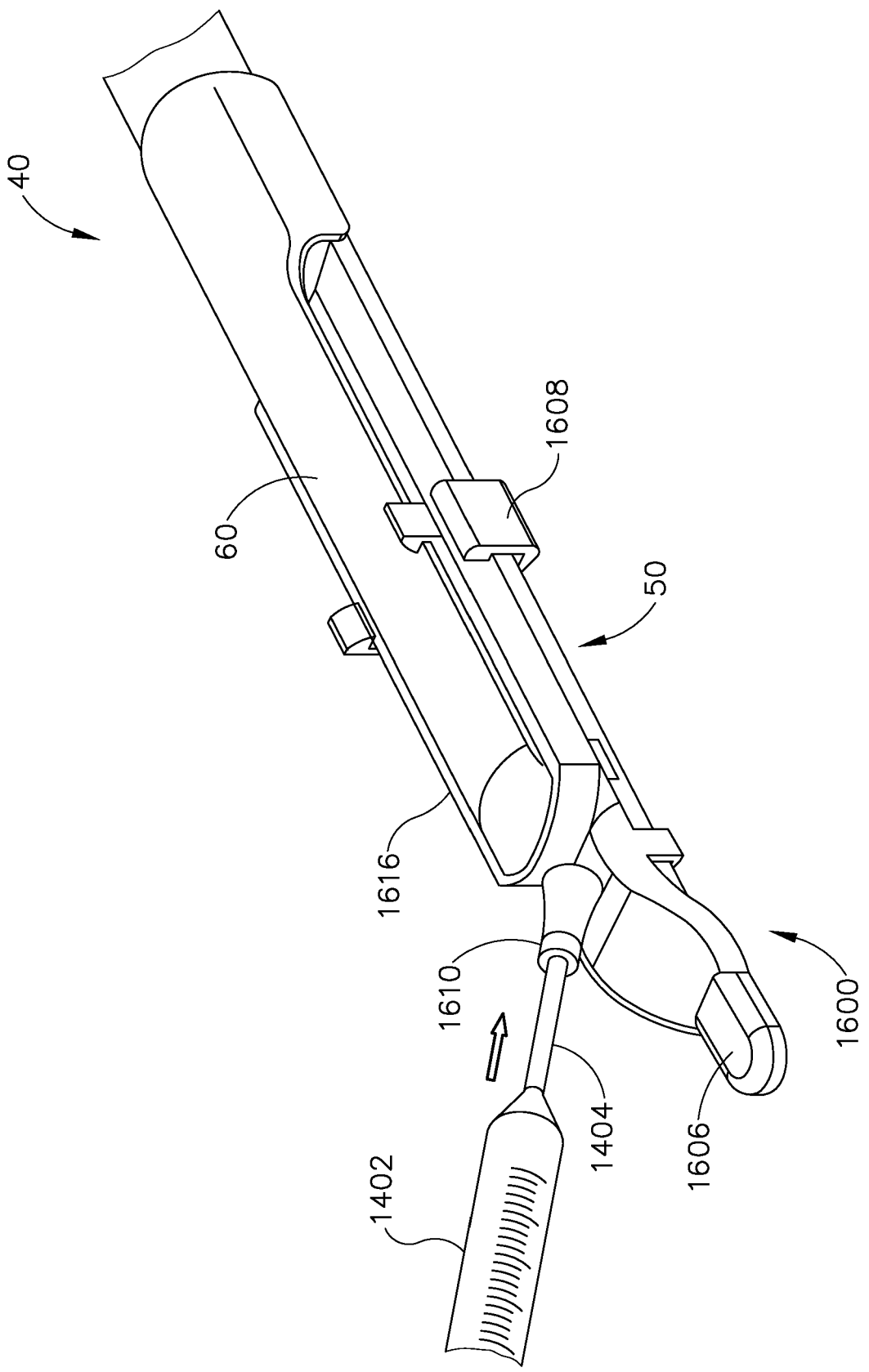
FIG. 33 depicts a perspective view of another exemplary alternative retainer assembly coupled with the end effector of FIG. 3, with a syringe injecting an adhesive material into the retainer assembly, and with the anvil of the end effector in a closed position.

FIG. 33 shows another exemplary alternative retainer (1600) that may be used to dispense a polymer adhesive gel directly at the site of end effector (40) as a buttress body (not shown) is being applied to end effector (40). Retainer (1600) of this example comprises a distally projecting tongue (1606), a set of resilient latches (1608), and an injection port (1610). It should be understood that tongue (1606) and latches (1608) may be configured and operable just like tongue (306) and latches (308) described above. Thus, retainer (1600) may be removably secured to lower jaw (50) to apply a buttress body to underside (65) of anvil (60). The buttress body of this example may be configured like any other buttress body described herein.

The upper side (not shown) of retainer (1600) may include a plurality of upwardly extending projections. These upwardly extending projections may be similar to projections (1312, 1314) of retainer (1300). In particular, the upwardly extending projections of retainer (1600) may be configured to extend into channel (62) and staple forming pockets (64) of anvil (60); and may be configured to serve as standoff features to provide a gap (not shown) between the upper side of a buttress body (which would be overlaid on the upper side of retainer (1600)) and underside (65) of anvil (60). Port (1610) would be in fluid communication with this gap, such that an adhesive gel may be injected into this port through a needle (1404) inserted into port (1610). Retainer (1600) also includes a lip portion (1616) that encompasses the outer perimeter of anvil (60). This lip portion (1616) may prevent the injected adhesive gel from escaping the perimeter of anvil (60). Similarly, the upwardly extending projections of retainer (1600) may prevent the adhesive gel from entering channel (62) and staple forming pockets (64) of anvil (60). In some versions, retainer (1600) only includes an upwardly extending projection associated with channel (62), such that the injected adhesive gel is free to enter staple forming pockets (64). In some other versions, retainer (1600) lacks an upwardly extending projection associated with channel (62). Other suitable variations will be apparent to those of ordinary skill in the art in view of the teachings herein.

While retainer (1300) may be used to dispense an adhesive gel (1330) while anvil (60) is in an open position, it should be understood that retainer (1600) is shown as being used to dispense an adhesive gel while anvil (60) is in the closed position. In some other instances, retainer (1600) may be used to dispense an adhesive gel to secure a buttress body to underside (65) of anvil (60) while anvil (60) is in the open position. It should also be understood that, in instances where a first buttress body is to be secured to deck (73) of staple cartridge (70) and a second buttress body (65) is to be secured to underside (65) of anvil (60), some versions of retainer (1600) may provide injection of adhesive gel via one or more ports into two different gaps. In particular, a retainer may be configured to provide injection of adhesive gel into a first gap defined between a buttress body and underside (65) of anvil (60); and into a second gap defined between a buttress body and deck (73) of staple cartridge (70). Some such retainers may provide filling of both gaps via a single port that is in fluid communication with both gaps. Alternatively, each gap may have its own associated injection port. Other suitable variations will be apparent to those of ordinary skill in the art in view of the teachings herein.

3. Exemplary Adhesive Injector with Mixing Feature

Figure 34:
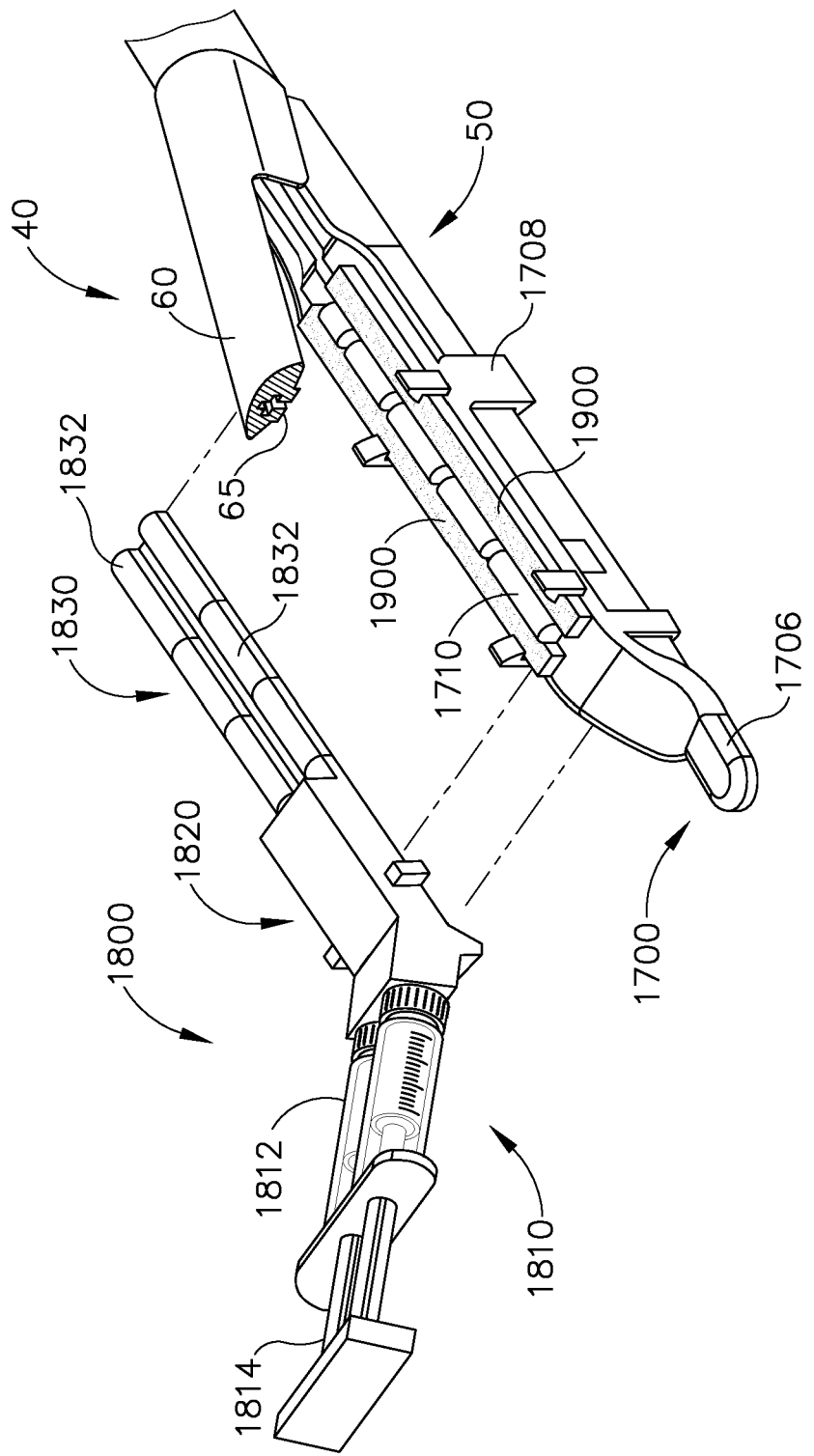
FIG. 34 depicts a perspective view of another exemplary alternative retainer assembly coupled with the end effector of FIG. 3, with an exemplary alternative syringe assembly positioned over the retainer assembly, and with the anvil of the end effector in an open position.
Figure 35:
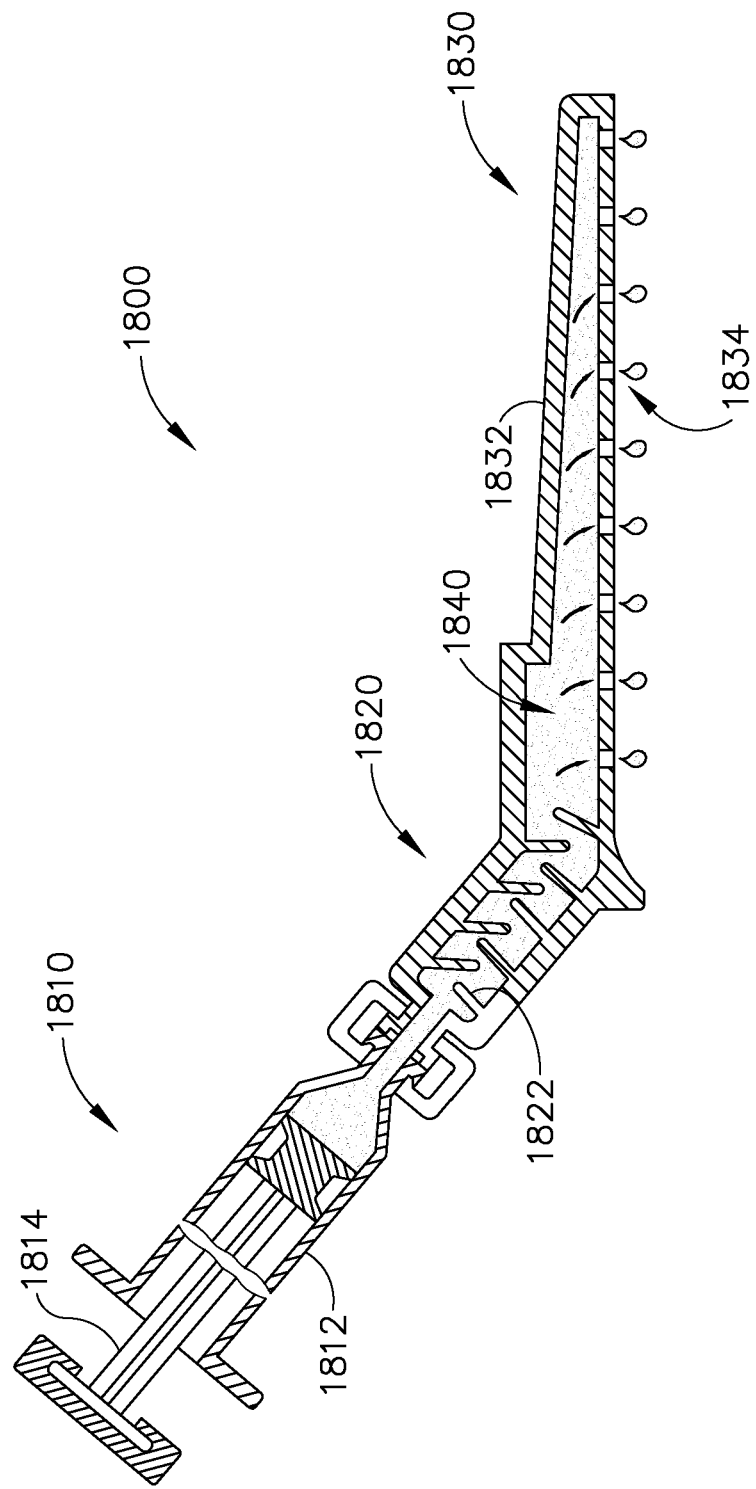
FIG. 35 depicts a cross-sectional side view of the syringe assembly of FIG. 34.

FIGS. 34-35 show another exemplary retainer (1700) and injector assembly (1800) that may be used to apply a polymer adhesive gel (1840) to secure buttress bodies (1900) to underside (65) of anvil (60). Retainer (1700) comprises a distally projecting tongue (1706), a set of resilient latches (1508), and a longitudinally extending, upwardly protruding ridge (1710). It should be understood that tongue (1706) and latches (1708) may be configured and operable just like tongue (306) and latches (308) described above. Thus, retainer (1700) may be removably secured to lower jaw (50). Ridge (1710) is configured and positioned to fit in a portion of channel (62), thereby preventing injected adhesive gel (1840) from entering channel (62). Each buttress body (1900) is positioned on either side of ridge (1710). Each buttress body (1900) may be configured like any other buttress body described herein.

Injector assembly (1800) of this example comprises a dual syringe assembly (1810), a mixing assembly (1820), and a dispenser assembly (1830). Dual syringe assembly (1810) includes a pair of syringe barrels (1812) and a plunger (1814) that is operable to drive fluid from both barrels (1820) simultaneously. Each syringe barrel (1812) may include a component or set of components of adhesive gel (1840). For instance, in some versions one syringe barrel (1812) contains fibrin and the other syringe barrel (1812) contains thrombin. In addition or in the alternative, one syringe barrel (1812) may contain a cellulose (e.g., oxidized regenerated cellulose (ORC)), starch, chitin, glycogen in a glycerin, or a polyethylene glycol (PEG); while the other syringe barrel (1812) contains a water solution. Other suitable materials and combinations will be apparent to those of ordinary skill in the art in view of the teachings herein.

Mixing assembly (1820) is in fluid communication with both syringe barrels (1812), such that fluid/gel injected from both barrels (1812) will enter mixing assembly (1820) simultaneously. As best seen in FIG. 35, mixing assembly (1820) includes a set of baffles (1822) that are configured to mix the two components from syringe barrels (1812) as the components flow through mixing assembly (1820). Various suitable configurations and arrangements that may be used for baffles (1822) will be apparent to those of ordinary skill in the art in view of the teachings herein.

In some versions, barrels (1812) and mixing assembly (1820) provide a mixture of the contents of barrels (1812) at a 1:1 ratio. Alternatively, any other suitable mixture ratio may be provided. By way of example only, some versions may provide a ratio of 7:1 fibrin to thrombin.

Dispenser assembly (1830) is in fluid communication with mixing assembly (1820), such that the liquid/gel (1840) that is mixed through mixing assembly (1820) will ultimately reach dispenser assembly (1830). As best seen in FIG. 34, dispenser assembly (1830) includes a set of distally projecting arms (1832). Each arm (1832) is configured to fit over a corresponding buttress body (1900). As best seen in FIG. 35, the underside of each arm (1832) includes a plurality of openings (1834). Openings (1834) are configured to convey the adhesive gel (1840) from arm (1830) to the upper side of the corresponding buttress body (1900). In some versions, each arm (1832) further includes a downwardly projecting lip about the outer perimeter of arm (1832). Such a lip may prevent the adhesive gel (1840) from escaping at the perimeter of arm (1832) during dispensation of the adhesive gel (1840). In addition or in the alternative, retainer (1700) may include an upwardly extending lip that is configured to prevent the adhesive gel (1840) from escaping at the perimeter of arm (1832) during dispensation of the adhesive gel (1840). Other suitable variations will be apparent to those of ordinary skill in the art in view of the teachings herein.

Once injector assembly (1800) has dispensed a sufficient amount of adhesive gel (1840) onto buttress bodies (1900), injector assembly (1800) may be removed. Anvil (60) may then be driven to the closed position to compress underside (65) against the dispensed adhesive gel (1840) and buttress bodies (1900). The adhesive gel (1840) may adhere buttress bodies (1900) to underside (65). Accordingly, as anvil (60) is returned to the open position, adhesive gel (1840) and buttress bodies (1900) may remain secured to underside (65). Retainer (1700) may then be removed from end effector (40) and end effector (40) will then be ready for use.

H. Flowable Bioabsorbable Polymer Adhesive

In some instances, it may be desirable to combine a flowable (i.e., low viscosity) adhesive material with buttress body (102), in addition to or as an alternative to having one or more adhesive layers (104, 106) on upper or lower surfaces of buttress body (102), to removably secure buttress assembly (100) to deck (73) of staple cartridge (70) or underside (65) of anvil (60). One merely illustrative example of a composition that may be used to provide a flowable adhesive material is a 50/50 copolymer of caprolactone and glycolide (PCL/PGA).

As another merely illustrative example, a flowable adhesive may be formulated in accordance with at least some of the teachings of U.S. Pub. No. 2005/0070929, entitled "Apparatus and Method for Attaching a Surgical Buttress to a Stapling Apparatus," published Mar. 31, 2005, now abandoned, the disclosure of which is incorporated by reference herein. For instance, a suitable flowable adhesive material may include one or more elastomeric polymers or copolymers that have an inherent viscosity (IV) of from about 1.2 dL/g to about 4 dL/g, or more particularly an inherent viscosity (IV) of from about 1.2 dL/g to about 2 dL/g, or more particularly an inherent viscosity (IV) of from about 1.4 dL/g to about 2 dL/g as determined at 25° C. in a 0.1 gram per deciliter (g/L) solution of polymer in hexafluoroisopropanol (HFIP). The elastomeric polymer may exhibit a high percent elongation and a low modulus, while possessing good tensile strength and good recovery characteristics. The elastomeric polymer may exhibit a percent elongation greater than about 200, preferably greater than about 500. It may also exhibit a modulus (Young's Modulus) of less than about 4000 psi, or more particularly less than about 20,000 psi. The properties, which measure the degree of elasticity of the biodegradable elastomeric polymer, may be achieved while maintaining a tensile strength greater than about 500 psi, more particularly greater than about 1,000 psi; and a tear strength of greater than about 50 lbs/inch, more particularly greater than about 80 lbs/inch.

Foam materials comprising elastomeric polymers (as a flowable adhesive material) may be formed by lyophilization, supercritical solvent foaming (e.g., as described in International Patent Pub. No. WO 91/09079, entitled "Use of Supercritical Fluids to Obtain Porous Sponges of Biodegradable Polymers" published Jun. 27, 1991, the disclosure of which is incorporated by reference herein), gas injection extrusion, gas injection molding, or casting with an extractable material (e.g., salts, sugar or any other means known to those skilled in the art). In some instances, biodegradable, biocompatible elastomeric foams are prepared by lyophilization. One suitable method for lyophilizing elastomeric polymers to form an exemplary buttress assembly (100) is described in U.S. Pat. No. 6,355,699, entitled "Process for Manufacturing Biomedical Foams," issued Mar. 12, 2002, the disclosure of which is incorporated by reference herein. As noted above, pharmaceutically active compounds may be incorporated into the buttress assembly (100) to further treat the patient, including but not limited to antibiotics, antifungal agents, hemostatic agents, anti-inflammatory agents, growth factors and the like.

As another merely illustrative example, an aliphatic polyester may be generally prepared by a ring-opening polymerization of the desired proportions of one or more lactone monomers in the presence of an organometallic catalyst and an initiator at elevated temperatures. The organometallic catalyst preferably is a tin-based catalyst, e.g. stannous octoate, and is present in the monomer mixture at a molar ratio of monomer to catalyst ranging from about 15,000/1 to about 80,000/1. The initiator typically is an alkanol (such as 1-dodecanol), a polyol (such as 1,2-propanediol, 1,3-propanediol, diethylene glycol, or glycerol, poly(ethylene glycol)s, polypropylene glycol)s and poly(ethylene-co-propylene glycol)s), a hydroxyacid, or an amine, and is present in the monomer mixture at a molar ratio of monomer to initiator ranging from about 100/1 to about 5000/1. The polymerization typically is carried out at a temperature range from about 80° C. to about 220° C., more particularly from about 160° C. to 190° C., until the desired molecular weight and viscosity (IV) are achieved. The resulting material may be used to provide a flowable adhesive material for buttress assembly (100).

As yet another merely illustrative example, the flowable adhesive material may comprise cellulosic and aliphatic ester homopolymers and copolymers made from polymers of the formula: [—O—$R^{11}$—C(O)—]$_y$, where $R^{11}$ is selected from the group consisting of —C$R^{12}$H—, —(CH$_2$)$_3$—O—, —CH$_2$—CH$_2$—O—CH$_2$—, CR 12H—CH$_2$, —(CH$_2$)$_4$—, —(CH$_2$)$_z$—O— and —(CH$_2$)$_z$—C(O)—CH$_2$—; $R^{12}$ is hydrogen or methyl; z is an integer in the range of from 1 to 7; and y is an integer in the range of from about 10 to about 20,000; blends of a viscous polyethylene glycol (PEG) liquid and a low melting solid polyethylene glycol (PEG) (solid at room temperature that melts at less than about 60° C.); biocompatible monosaccharides, disaccharides and polysaccharides (such as pectin) that may be mixed with a plasticizer (such as glycerine) to form a tacky adhesive and biocompatible proteins (such as gelatin) that may mixed with a plasticizer (such as glycerine) to form a tacky adhesive.

Many nontoxic bioabsorbable aliphatic ester polymers that are semi-crystalline solids or tacky liquids at room temperature may be used as a releasable adhesive. The releasable adhesive may be flowable at body temperature (37° C.) and in some instances will flow at room temperatures (25° C.). These liquids will may further have a low yield point to avoid migration of the polymer. Examples of suitable tacky liquid copolymers are taught in U.S. Pat. No. 5,824,333, entitled "Injectable Liquid Copolymers for Soft Tissue Repair and Augmentation," issued Oct. 20, 1998, the disclosure of which is incorporated by reference herein. Additionally, tacky microdispersions may also be used such as those described in U.S. Pat. No. 5,599,852, entitled "Plylactone Homo- and Copolymers," issued Feb. 4, 1997, the disclosure of which is incorporated by reference herein.

A suitable flowable adhesive material may comprise a liquid copolymer composed of in the range of from about 65 mole percent to about 35 mole percent of epsilon-caprolactone, trimethylene carbonate, ether lactone (which for the purpose of this invention is defined to be 1,4-dioxepan-2-one and 1,5-dioxepan-2-one) repeating units or combinations thereof with the remainder of the polymer being a plurality of second lactone repeating units are preferred. The second lactone repeating units may be selected from the group consisting of glycolic acid repeating units, lactic acid repeating units, 1,4-dioxanone repeating units, 6,6-dialkyl-1,4-dioxepan-2-one, combinations thereof and blends thereof. Additionally, epsilon-caprolactone, trimethylene carbonate, or an ether lactone may be copolymerized to provide a liquid copolymer. Exemplary polymers that may be used as particulate solids are bioabsorbable polymers including homopolymers of poly(epsilon-caprolactone), poly(p-dioxanone), or poly(trimethylene carbonate), copolymers of epsilon-caprolactone and trimethylene carbonate, copolymers of epsilon-caprolactone and a plurality of second lactone repeating units. The second lactone repeating units may be selected from the group consisting of glycolic acid repeating units, lactic acid repeating units, 1,4-dioxanone repeating units, 1,4-dioxepan-2-one repeating units, 1,5-dioxepan-2-one repeating units and combinations thereof. The copolymers of epsilon-caprolactone may be composed of from 99 mole percent to 70 mole percent epsilon-caprolactone with the remainder of the polymer being a plurality of second lactone repeating units.

The polymers may be linear, branched, or star branched; block copolymers or terpolymers; segmented block copolymers or terpolymers. These polymers will also be purified to substantially remove unreacted monomers that may cause an inflammatory reaction in tissue.

Further examples of liquid copolymers that may be used as a flowable, releasable adhesive are composed of in the range of from about 65 mole percent to about 35 mole percent epsilon-caprolactone or an ether lactone repeating unit with the remainder of the copolymer being trimethylene carbonate repeating units. Examples of suitable terpolymers are terpolymers selected from the group consisting of poly (glycolide-co-epsilon-caprolactone-co-p-dioxanone) and poly(lactide-co-epsilon-caprolactone-co-p-dioxanone)

wherein the mole percent of epsilon-caprolactone repeating units is from about 35 to about 65 mole percent.

Further examples include terpolymers having in the range of from 40 to 60 mole percent of epsilon-caprolactone repeating units. Examples of liquid copolymer for use as the flowable, releasable adhesive may be selected from the group consisting of poly(epsilon-caprolactone-co-trimethylene carbonate), poly(lactide-co-trimethylene carbonate), poly(epsilon-caprolactone-co-p-d-ioxanone), poly(trimethylene carbonate-co-p-dioxanone), poly(epsilon-caprolactone-co-lactide), poly(lactide-co-1,5-dioxepan-2-one-), and poly(1,5-dioxepan-2-one-co-p-dioxanone), poly(lactide-co-1,4-dioxep-an-2-one), and poly(1,4-dioxepan-2-one-co-p-dioxanone). The mole percent of epsilon-caprolactone, trimethylene carbonate or ether lactone repeating units in these polymers should be in the range of from about 35 to about 65 mole percent and more particularly in the range of from 40 to 60 mole percent. In some cases these liquid polymers will be statistically random copolymers. These polymers will also be purified to substantially remove unreacted monomers that may cause an inflammatory reaction in tissue.

As noted above, exemplary polymers used as the flowable, releasable adhesive have an inherent viscosity (IV) as determined in a 0.1 g/dL solution of hexafluoroisopropanol (HFIP) at 25° C. ranging from about 0.1 dL/g to about 0.8 dL/g, more particularly from about 0.1 dL/g to about 0.6 dL/g, and more particularly from 0.15 dL/g to 0.25 dL/g for liquid polymers. Additionally, blends of liquid and solid polyethylene glycols (PEG) may be used as releasable adhesives. The liquid polyethylene glycols (PEG) may have a molecular weight from about 200 to about 600. The solid polyethylene glycols (PEG) may have a molecular weight from about 3400 to about 10,000. Generally it is theorized, but in no way limits the scope of this invention, that the low molecular weight liquid polyethylene glycols (PEG) plasticizes the solid polyethylene glycols (PEG) to render the solid polyethylene glycols (PEG) tacky. Consequently, in some versions, the majority of the composition is be the solid polyethylene glycols (PEG) and more particularly between about 50 and about 80 percent by weight of the composition will be solid polyethylene glycols (PEG). For example, a liquid polyethylene glycol (PEG) with molecular weight of 400 (PEG 400) may be blended with a solid polyethylene glycol (PEG) with a molecular weight of about 2,000 (PEG 2000). The ratio of PEG 400 to PEG 2000 may vary from about 40:60 to about 30:70. These blends may be formed by mixing the liquid polyethylene glycol (PEG) and the solid polyethylene glycol (PEG) with constant stirring in a heated water bath until the solid melts and a clear liquid solution is formed. After these solutions are allowed to cool and the resulting mixture may be tested for tackiness and used if the desired tackiness is obtained.

Other suitable compositions that may provide a flowable adhesive material will be apparent to those of ordinary skill in the art in view of the teachings herein. The below examples include various exemplary configurations through which one or more flowable adhesive materials may be combined with a buttress body (102) to removably secure buttress assembly (100) to deck (73) of staple cartridge (70) or underside (65) of anvil (60). In the present example, it is contemplated that the adhesive material comprises a synthetic based polymer such as those referred to herein. However, it should also be understood that naturally based polymers may be incorporated with the below teachings.

In some instances, the adhesive material may be flowable at room temperature. Flowable adhesive materials may rely on their surface tension, cohesion, viscosity (IV), and mechanical features of the two attaching surfaces to create a bonding effect. The two attaching surfaces could be completely smooth mating surfaces with the flowable adhesive material interposed between the two surfaces. Alternatively, the two attaching surfaces could have interlocking features where the flowable adhesive material takes a tortuous path when clamped between the two surfaces, thereby maximizing the contact surfaces and surface tension to hold them together. Flowable adhesive materials may also interface with small surface properties of a buttress body (102). For instance, in versions where buttress body (102) is formed as a fiber weave, the flowable adhesive material may flow into spaces between the fibers. Similarly, in versions where buttress body (102) is structured like a sponge, the flowable adhesive material may flow into various cells of the structure. Other various ways in which a flowable adhesive material may interact with a buttress body (102) and either deck (73) of staple cartridge (70) or underside (65) of anvil (60) will be apparent to those of ordinary skill in the art in view of the teachings herein.

By way of example only, a flowable adhesive material may be injected into place between a buttress body (102) and either deck (73) of staple cartridge (70) or underside (65) of anvil (60) using any of the structures and techniques described above with reference to FIGS. 31-35. In other words, a flowable adhesive material may be introduced and administered just like an adhesive gel. Alternatively, any other suitable structures or techniques may be used to provide a flowable adhesive material between a buttress body (102) and either deck (73) of staple cartridge (70) or underside (65) of anvil (60). Several additional examples will be described in greater detail below while other examples will be apparent to those of ordinary skill in the art in view of the teachings herein.

1 Exemplary Buttress Assembly with Discrete Adhesive Droplets

Figure 36:
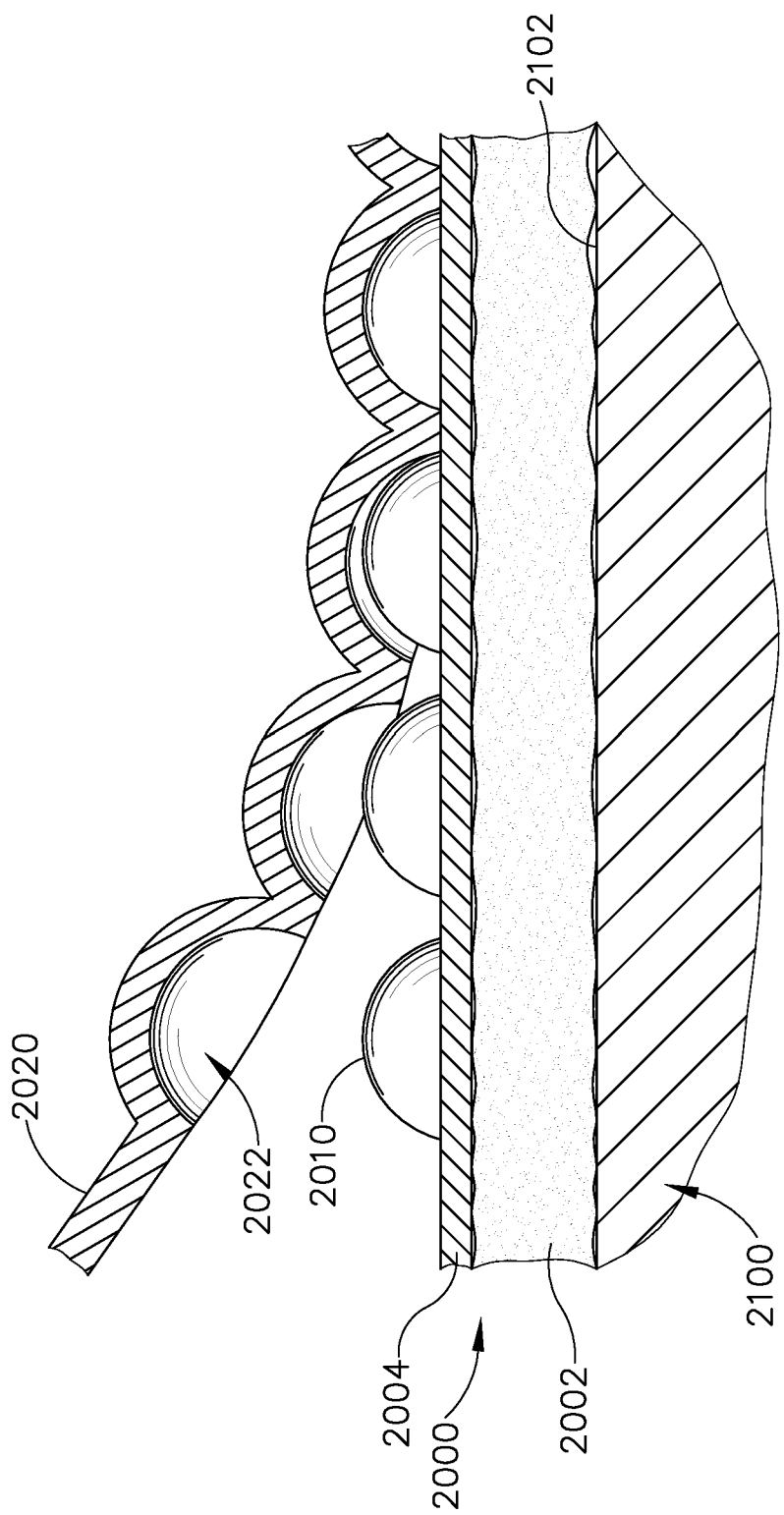
FIG. 36 depicts a cross-sectional side view of an exemplary alternative buttress assembly, with a protective layer being peeled away.
Figure 37:
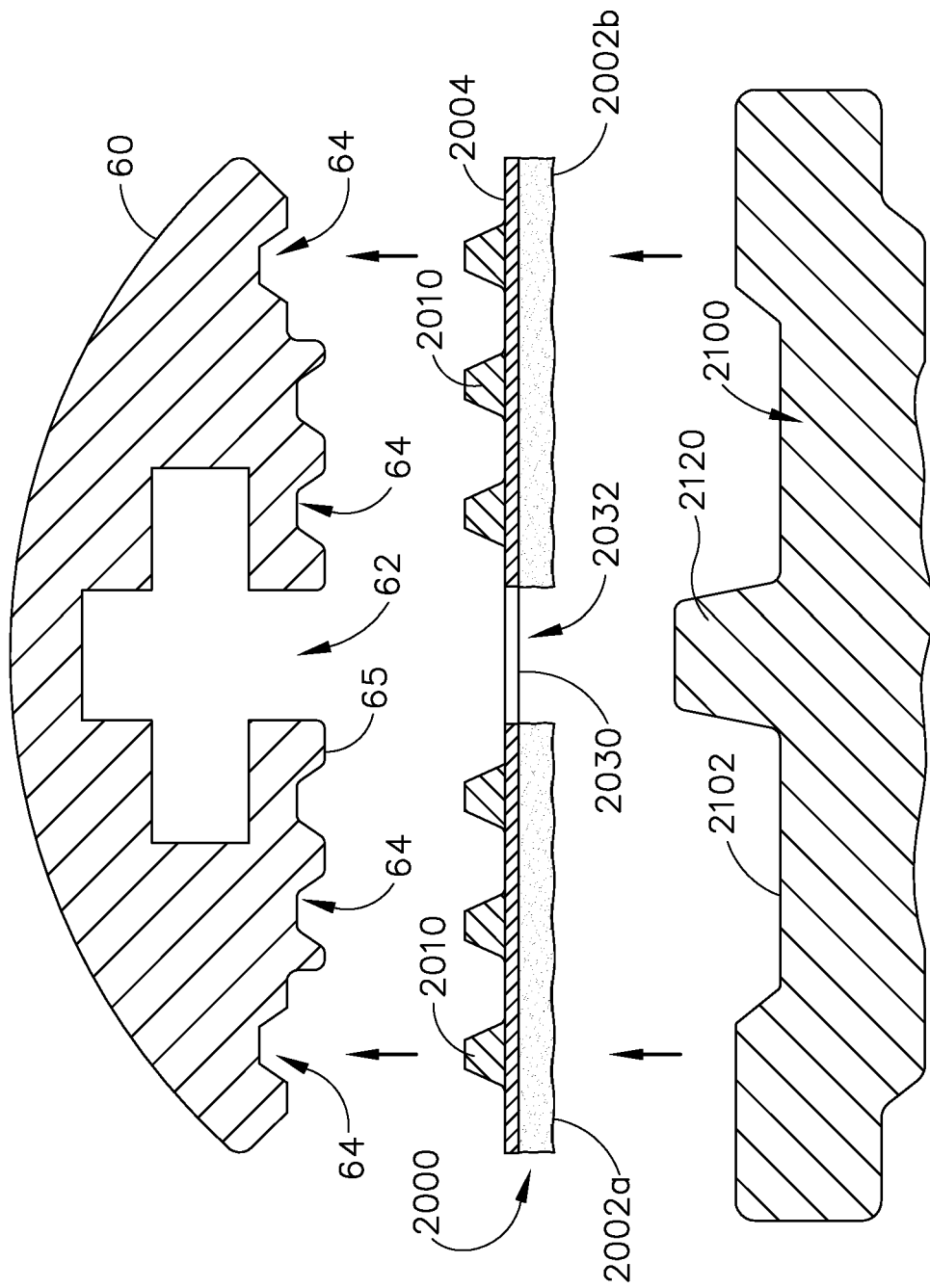
FIG. 37 depicts an exploded cross-sectional end view of the buttress assembly of FIG. 36 positioned between an exemplary retainer and the anvil of the end effector of FIG. 3.

FIGS. 36-37 show an exemplary buttress assembly (2000) that comprises a buttress body (2002), an impermeable layer (2004), and a layer of flowable adhesive material (2010). Buttress assembly (2000) is positioned on an upper surface (2102) of a retainer (2100). Retainer (2100) may be configured and operable in accordance with any of the various retainers described herein. Buttress body (2002) may be configured in accordance with any buttress body described herein. In some versions, buttress body (2002) comprises a porous media (e.g., ETHISORB™ by Codman of Raynham, Mass.). Other suitable forms that buttress body (2002) may take will be apparent to those of ordinary skill in the art in view of the teachings herein. As shown in FIG. 37, buttress body (2002) is provided in two sections (2002a, 2002b) that are joined by one or more tethers (2030) that span across a gap (2032) defined between buttress body sections (2002a, 2002b). Gap (2032) extends longitudinally and is sized to complement channels (62, 72) of anvil (60) and staple cartridge (70).

Impermeable layer (2004) is configured to prevent flowable adhesive material (2010) from flowing into buttress body (2002). Various suitable materials that may be used to form impermeable layer (2004) will be apparent to those of ordinary skill in the art in view of the teachings herein. In some variations, a semi impermeable layer may be used in place of impermeable layer (2004). Such a semi impermeable layer may allow a limited amount of the flowable adhesive material (2010) to flow into buttress body (2002). By way of example only, such a semi impermeable layer may comprise polydioxanone (PDS). It should be understood from the foregoing that buttress body (2002) and impermeable layer (2004) (or a semi impermeable layer) may provide a laminate of a fibrous and/or porous material and a homogenous film.

In the present example, flowable adhesive material (2010) is provided in the form of several discrete droplets on top of impermeable layer (2004). An impermeable peel-away film (2020) is laid over flowable adhesive material (2010) and buttress body (2002). Film (2020) defines a plurality of pockets (2022) that are configured to contain flowable adhesive material (2010) in the form of discrete droplets. Film (2020) is configured to adhere to impermeable layer (2004) during storage and transport of buttress assembly (2000), but may be peeled away to expose flowable adhesive material (2010) right before buttress assembly (2000) is installed on end effector (40). The discrete droplets of adhesive material (2010) are sized and positioned to correspond with the positioning of staple forming pockets (64) of anvil (60). Thus, the discrete droplets of adhesive material (2010) are arranged in three longitudinally extending linear arrays. Alternatively, any other suitable arrangement may be used.

Retainer (2100) of the present example includes an upwardly projecting rib (2120). Rib (2120) extends longitudinally and is sized to complement channel (62) of anvil (60). As anvil (60) is driven to a closed position to compress buttress assembly (2000) against upper surface (2102), rib (2020) may enter channel (62) and break tethers (2020). Rib (2020) may also ensure proper lateral alignment of retainer (2000) and buttress assembly (2000) with anvil (60). Various suitable forms that rib (2120) may take will be apparent to those of ordinary skill in the art in view of the teachings herein. In some versions, rib (2120) is omitted. In some versions, upper surface (2102) further comprises a plurality of upwardly extending projections that are positioned to correspond with the positions of droplets of flowable adhesive material (2010) and staple forming pockets (64). Such projections may thus be configured to provide focused pressure to regions of buttress assembly (2000) at regions corresponding to staple forming pockets (64) of underside (65) when anvil (60) is driven to a closed position against buttress assembly (2000) and retainer (2100), thereby further promoting adhesion of flowable adhesive material (2010) in staple forming pockets (64) of underside (65).

2. Exemplary Cartridge with Adhesive Troughs

Figure 39:
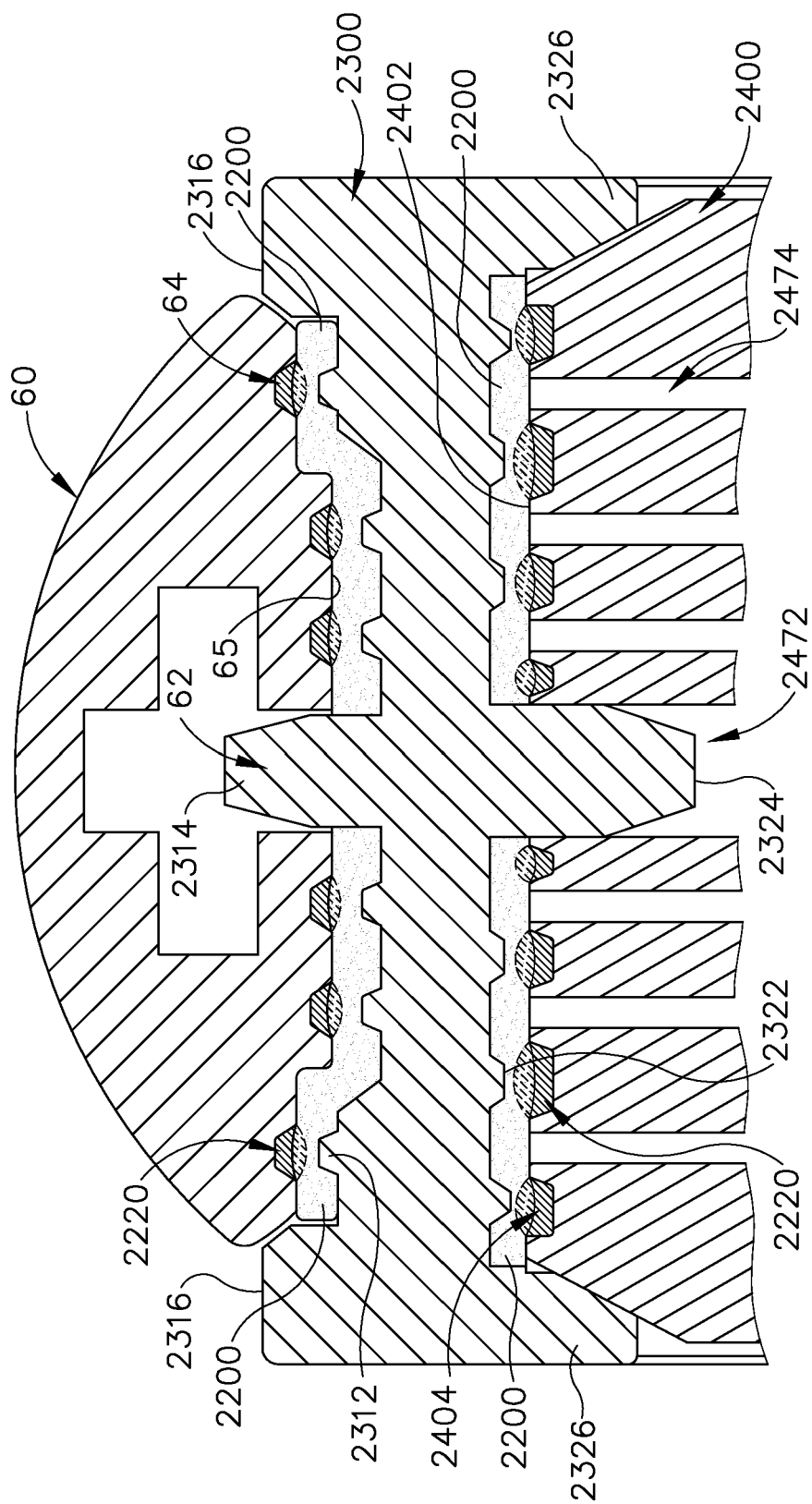
FIG. 39 depicts a cross-sectional end view of the staple cartridge, buttress, and retainer of FIG. 38, with an additional buttress and an anvil in a closed position.
Figure 40:
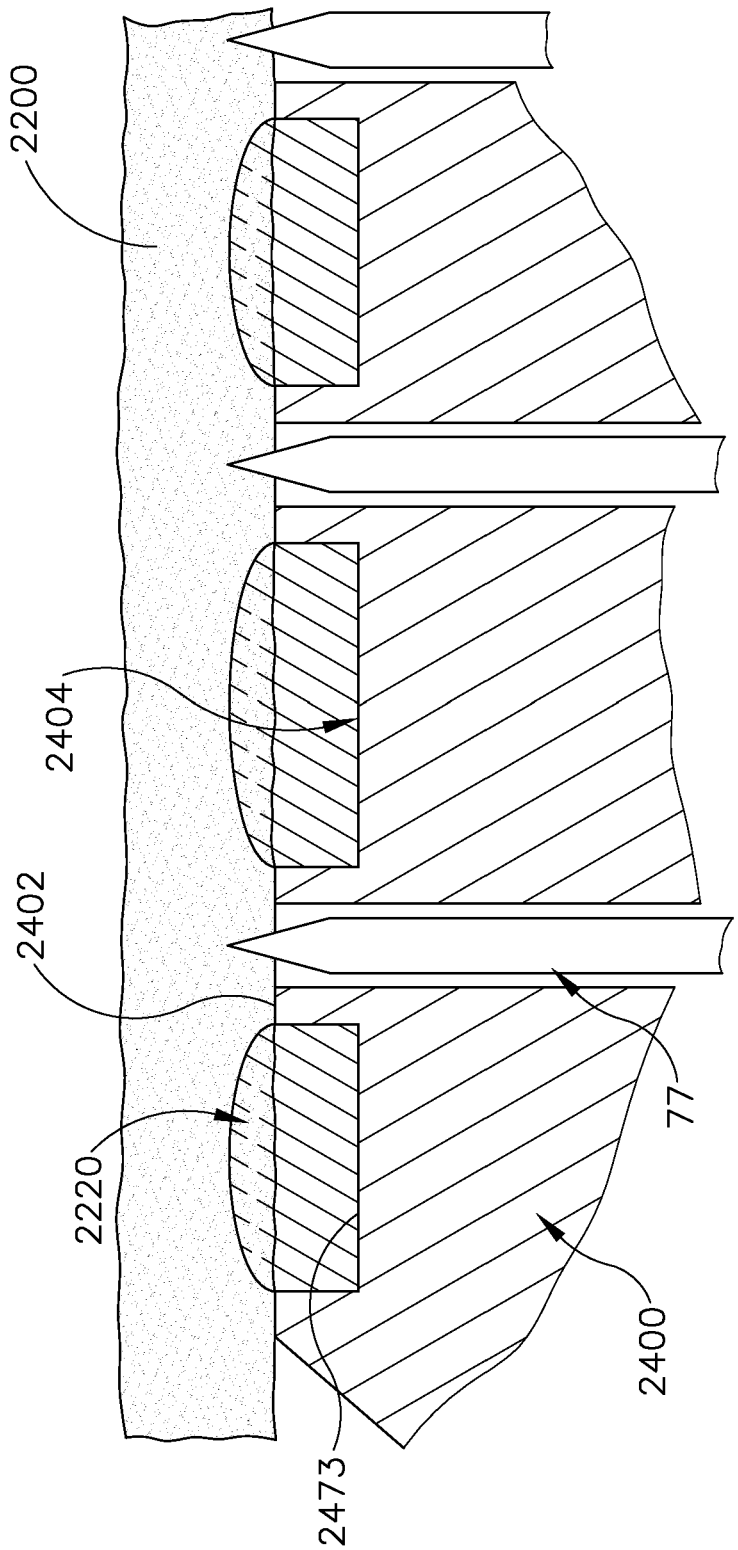
FIG. 40 depicts a cross-sectional view of the buttress of FIG. 38 secured to the deck of the staple cartridge of FIG. 38.

FIGS. 38-40 show an exemplary set of buttress bodies (2200), retainer (2300), and staple cartridge (2400). Buttress bodies (2200) are provided in two pairs in this example. As best seen in FIG. 39, a lower pair of buttress bodies (2200) is configured such that each buttress body (2200) fits on a respective side of channel (2472) of staple cartridge (2400); while an upper pair of buttress bodies (2200) is configured such that each buttress body (2200) fits on a respective side of channel (62) of anvil (60). Each buttress body (2200) may be configured and operable in accordance with any buttress body (2200) described herein.

Retainer (2300) of the present example has an upper surface (2310) and a lower surface (2320). Upper surface (2310) includes a plurality of upwardly extending projections (2312); an upwardly projecting, longitudinally extending rib (2314); and a pair of upwardly projecting, longitudinally extending side rails (2316). Projections (2312) are configured and positioned to correspond with staple forming pockets (64) on underside (65) of anvil (60). Rib (2314) is sized to complement channel (62) of anvil (60). Lower surface (2320) includes a plurality of downwardly extending projections (2322); a downwardly projecting, longitudinally extending rib (2324); and a pair of downwardly projecting, longitudinally extending side rails (2326). Projections (2322) are configured and positioned to correspond with troughs (2404) that are formed in staple cartridge (2400) as will be described in greater detail below. Rib (2324) is sized to complement channel (2472) of staple cartridge (2400).

Staple cartridge (2400) of the present example is substantially identical to staple cartridge (70) described above. However, unlike staple cartridge (70), staple cartridge (2400) of this example has a deck (2473) that includes upwardly extending ridges (2402) that surround each staple pocket (2474). These ridges (2402) thus define a trough (2404) on each side of channel (2472). A flowable adhesive material (2220) is provided in each trough (2404). As best seen in FIG. 40, ridges (2402) are configured to prevent flowable adhesive material (2220) from flowing into staple pockets (2474). When retainer (2300) loaded with buttress bodies (2200) is placed against staple cartridge (2400) as shown in FIG. 39, buttress bodies (2200) are laid over flowable adhesive material (2220) and contact the top surfaces of each ridge (2402). Buttress bodies (2200) and ridges (2402) thus cooperate to contain adhesive material (2220) in troughs (2404). It should be understood that there are numerous ways in which flowable adhesive material (2220) may be introduced into troughs (2404), before or after buttress bodies (2200) are placed against staple cartridge (2400). By way of example only, flowable adhesive material (2220) may be injected into troughs (2404) as described above, before or after buttress bodies (2200) are placed against staple cartridge (2400). As another merely illustrative example, staple cartridge (2400) may be pre-loaded with flowable adhesive material (2220) in troughs (2404), with an impermeable peel away film being secured to ridges (2402). In such versions, the peel away film may contain the flowable adhesive material (2220) in troughs (2404) during storage and transport; and may then be peeled away right before buttress bodies (2200) are placed against staple cartridge (2400). Other suitable ways in which flowable adhesive material (2220) may be provided and contained in troughs (2404) will be apparent to those of ordinary skill in the art in view of the teachings herein.

Similarly, flowable adhesive material (2220) is positioned in staple forming pockets (64) of anvil (60). Such flowable adhesive material (2220) may be provided and contained in staple forming pockets (64) using any of the techniques described above with respect to providing and containing flowable adhesive material (2220) in troughs (2404). As another merely illustrative example, buttress bodies (2200) may be configured with discrete droplets of adhesive material (2220), with a peel-away film layer used to contain the adhesive material (2220) in the form of discrete droplets, similar to buttress assembly (2000) described above. Other suitable ways in which flowable adhesive material (2220) may be provided and contained in staple forming pockets (64) will be apparent to those of ordinary skill in the art in view of the teachings herein.

When retainer (2300) loaded with buttress bodies (2200) is positioned between anvil (60) and staple cartridge (2400), with flowable adhesive material (2220) in troughs (2404) and either in staple forming pockets (64) or in positions to enter staple forming pockets (64), anvil (60) may be brought to a closed position as shown in FIG. 39. At this stage, projections (2312) are configured to provide focused pressure to regions of buttress bodies (2200) at regions corresponding to staple forming pockets (64); while projections (2322) are configured to provide focused pressure to regions of buttress bodies (2200) at regions corresponding to troughs (2404). In addition, ribs (2314, 2324) enter corresponding channels (62, 2472) and prevent flowable adhesive material (2220) from entering channels (62, 2472). Ribs (2314, 2324) may also ensure proper lateral alignment of retainer (2300) and buttress bodies (2200) with anvil (60) and staple cartridge (2400). Side rails (2316, 2326) are configured to further contain flowable adhesive material (2220). Side rails (2316, 2326) may also assist in ensuring proper lateral alignment of retainer (2300) and buttress bodies (2200) with anvil (60) and staple cartridge (2400). After anvil (60) has been brought to the closed position, anvil (60) may be brought back to the open position and retainer (2300) may be removed, leaving buttress bodies (2200) adhered to underside (65) of anvil (60) and deck (2473) of staple cartridge (2470).

As another merely illustrative variation, buttress bodies (2200) may each define a plurality of pockets that are configured to contain flowable adhesive material (2220) in the form of discrete droplets. In some such versions, a flat impermeable peel-away film is laid over flowable adhesive material (2220) and each buttress body (2200), containing flowable adhesive material (2220) in the pockets of buttress body (2200). In some other versions, such peel-away film also defines a plurality of pockets that are configured to cooperate with the pockets of buttress body (2220) to contain flowable adhesive material (2220) in the form of discrete droplets. It should be understood that such variations may be used in combination with staple cartridge (2400) or staple cartridge (70).

As yet another merely illustrative variation, each buttress body (2200) may include a plurality of discrete regions of increased thickness. In the pair of upper buttress bodies (2200), these discrete regions of increased thickness may be located at positions corresponding to staple forming pockets (64). In the pair of lower buttress bodies (2200), these discrete regions of increased thickness may be located at positions corresponding to troughs (2404). The discrete regions of increased thickness may serve functions similar to those of projections (2312, 2322), such that projections (2312, 2322) may be omitted. In particular, discrete regions of increased thickness in buttress bodies (2200) may provide focused pressure to regions of buttress bodies (2200) at regions corresponding to staple forming pockets (64) and troughs (2404). Each buttress body (2200) may also have regions of increased thickness at locations corresponding to channels (62, 2472), such that regions of increased thickness in buttress bodies (2200) may serve as structural substitutes for (and functional equivalents of) ribs (2314, 2324).

3. Exemplary Retainer with Foam Biasing Features

Figure 41:
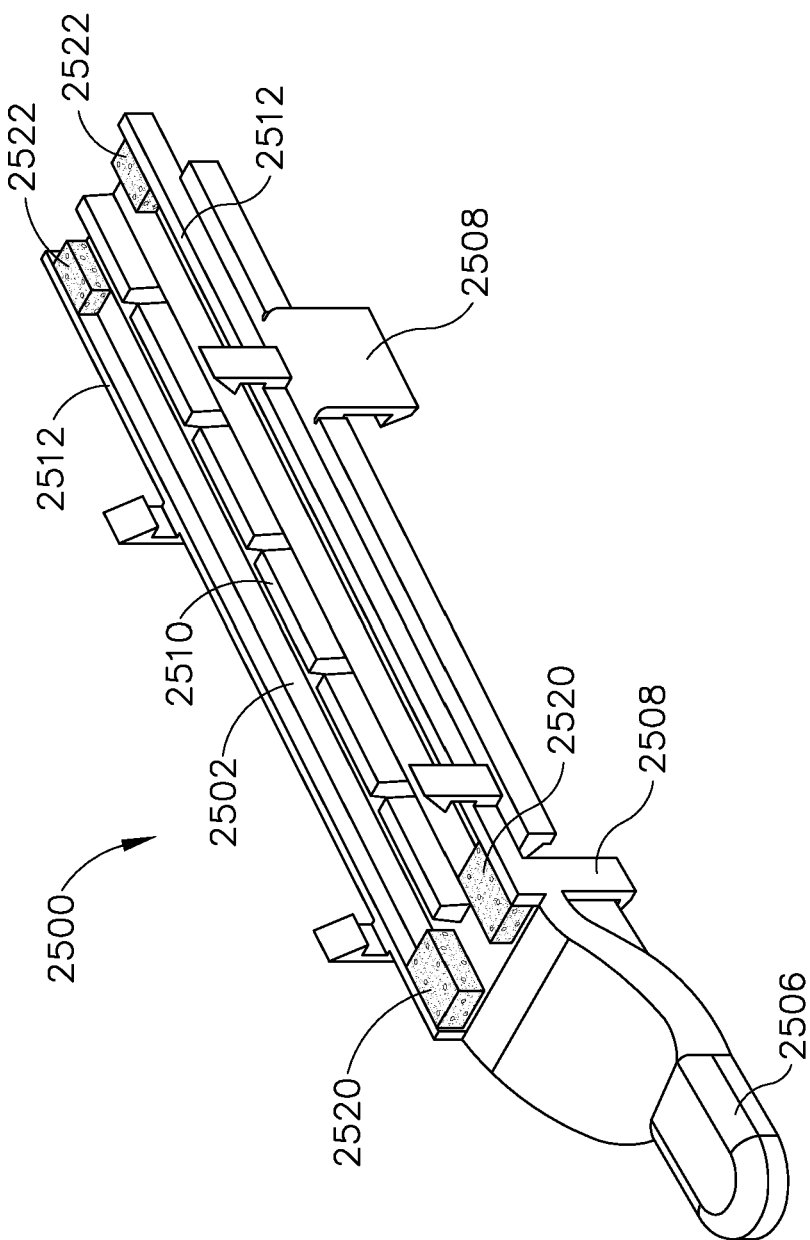
FIG. 41 depicts a perspective view of an exemplary alternative retainer assembly.
Figure 42:
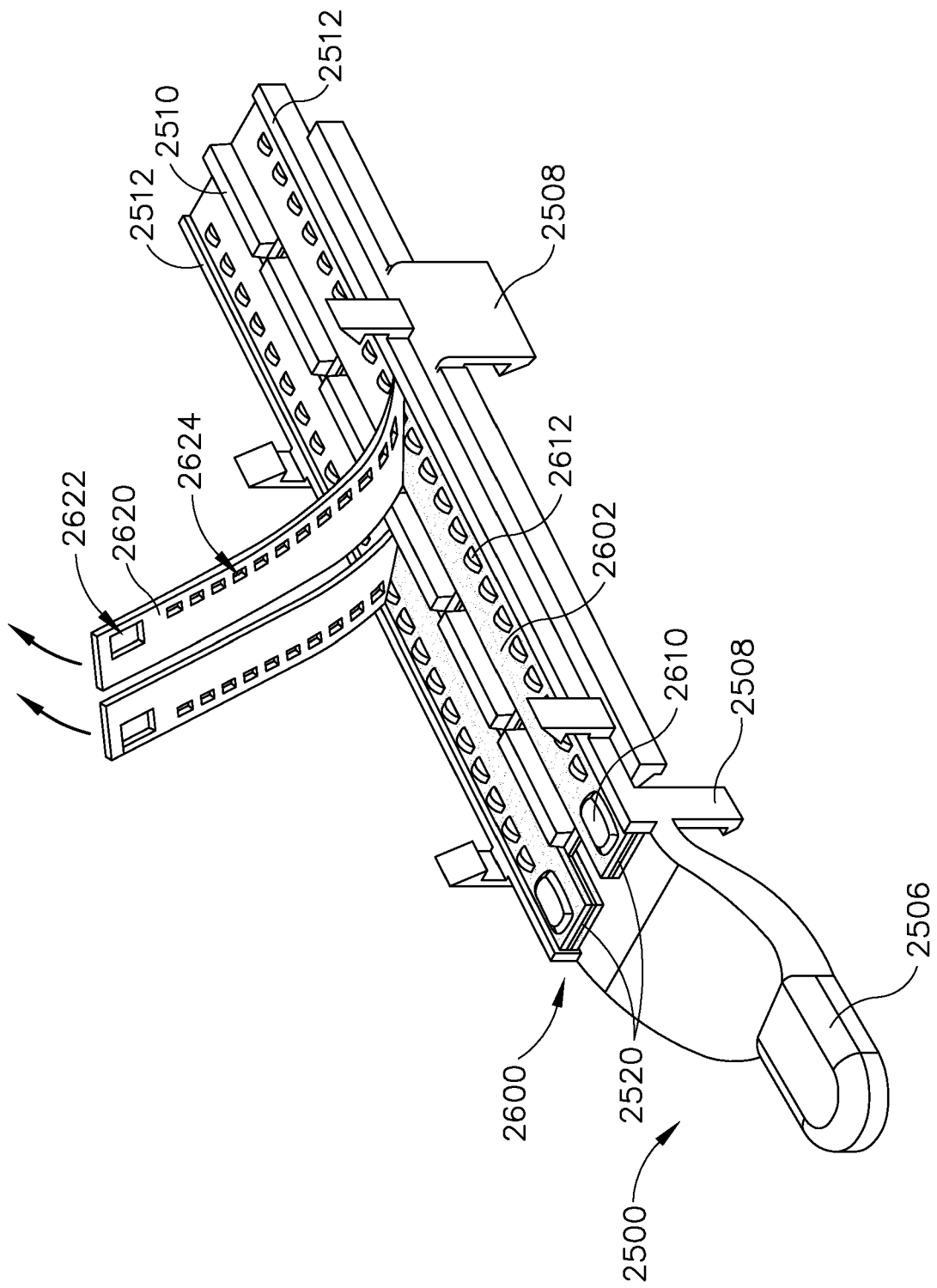
FIG. 42 depicts a perspective view of a buttress assembly positioned on the retainer assembly of FIG. 41, with a protective layer being peeled away from the buttress assembly.

FIGS. 41-42 show another exemplary alternative retainer (2500) that is configured for use with a buttress assembly (2600). Retainer (2500) of this example comprises a distally projecting tongue (2506); a set of resilient latches (2508); an upwardly projecting, longitudinally extending rib (2510); a pair of upwardly projecting, longitudinally extending side rails (2512); and a set of foam members (2520, 2522). It should be understood that tongue (2506) and latches (2508) may be configured and operable just like tongue (306) and latches (308) described above. Thus, retainer (2500) may be removably secured to lower jaw (50) to apply a buttress body to underside (65) of anvil (60). It should also be understood that rib (2510) and rails (2512) may be configured and operable just like rib (2314) and side rails (2316) described above. Thus, rib (2510) and rails (2512) may assist in ensuring proper positioning of retainer (2500) and may further assist in containing flowable adhesive material at appropriate locations.

Buttress assembly (2600) is configured substantially similar to buttress assembly (2000) described above. In particular, buttress assembly (2600) comprises a pair of buttress bodies (2602), each having a layer of flowable adhesive material (2610, 2612) in discrete regions. In particular, each buttress body (2602) has a large distal region of flowable adhesive material (2610) and several smaller regions of flowable adhesive material (2612) proximal to the distal region of flowable adhesive material (2610). Buttress bodies (2602) may be configured in accordance with any buttress body described herein. In some versions, an impermeable or semi-impermeable layer is positioned over each buttress body (2602), interposed between buttress body (2602) and flowable adhesive material (2610, 2612), to thereby prevent or restrict the flow of flowable adhesive material (2610, 2612) into buttress body (2602).

An impermeable peel-away film (2620) is laid over flowable adhesive material (2610, 2612) and buttress body (2602). Film (2620) defines a plurality of pockets (2622, 2624) that are configured to contain flowable adhesive material (2610, 2612) in the form of discrete droplets. Film (2620) is configured to adhere to buttress body (2602) (or an impermeable layer or semi-impermeable layer that is laid over buttress body (2602)) during storage and transport of buttress assembly (2600), but may be peeled away to expose flowable adhesive material (2610, 2612) right before buttress assembly (2600) is installed on end effector (40). Pocket (2622) is larger than pockets (2624), such that pockets (2622) are sized to correspond with the larger size of distal region of flowable adhesive material (2610); while pockets are sized to correspond with the smaller size of smaller regions of flowable adhesive material (2612).

Foam members (2520, 2522) comprise a pair of distal foam members (2520) and a pair of proximal foam members (2522). Foam members (2520, 2522) may comprise any suitable foam material. Each foam member (2520, 2522) is configured to provide an upward bias to buttress assembly (2600), though foam members (2520, 2522) are compressible. It should be understood that foam members (2520, 2522) may provide a homogenous pressure urging buttress assembly (2600) into engagement with underside (65) of anvil (60) when anvil (60) compresses buttress assembly (2600) against retainer (2500). While foam members (2520, 2522) are formed as discrete blocks at distal and proximal regions of retainer (2500) in this example, foam members (2520, 2522) may alternatively have any other suitable configuration. By way of example only, foam members (2520, 2522) may extend longitudinally along the full length of upper surface (2502) of retainer (2500). Other suitable configurations and compositions that may be used for foam members (2520, 2522) will be apparent to those of ordinary skill in the art in view of the teachings herein.

4. Exemplary Buttress Assembly with Adhesive Retaining Pockets

Figure 43:
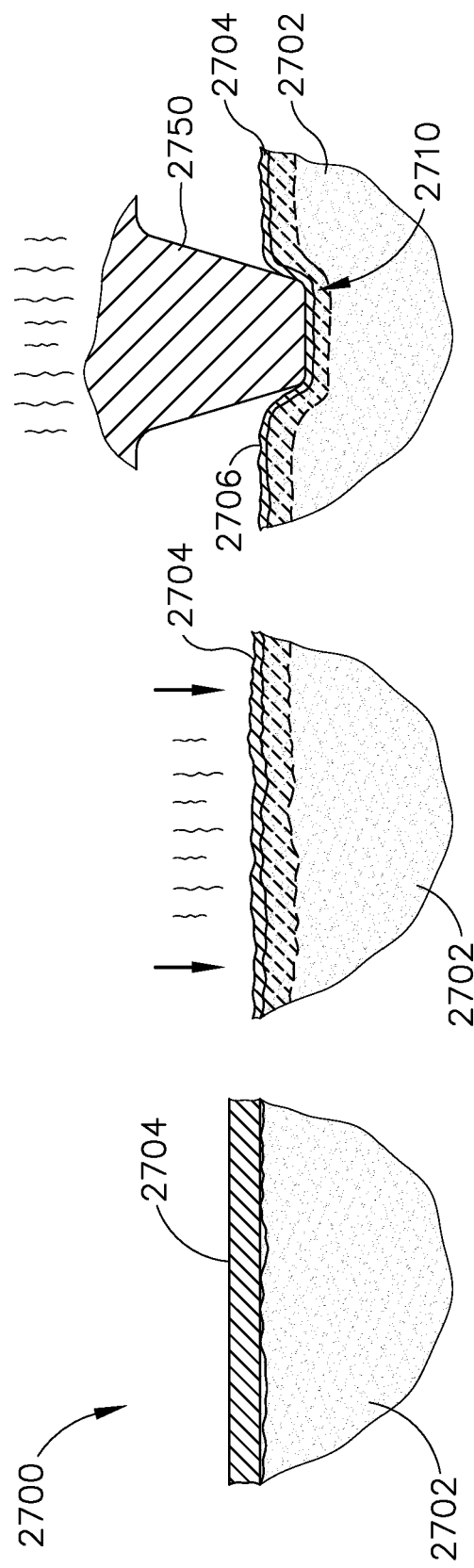
FIG. 43A depicts a cross-sectional view of an exemplary buttress assembly in a first state of preparation.
FIG. 43B depicts a cross-sectional view of an exemplary buttress assembly in a second state of preparation.
FIG. 43C depicts a cross-sectional view of an exemplary buttress assembly in a third state of preparation.
Figure 44:
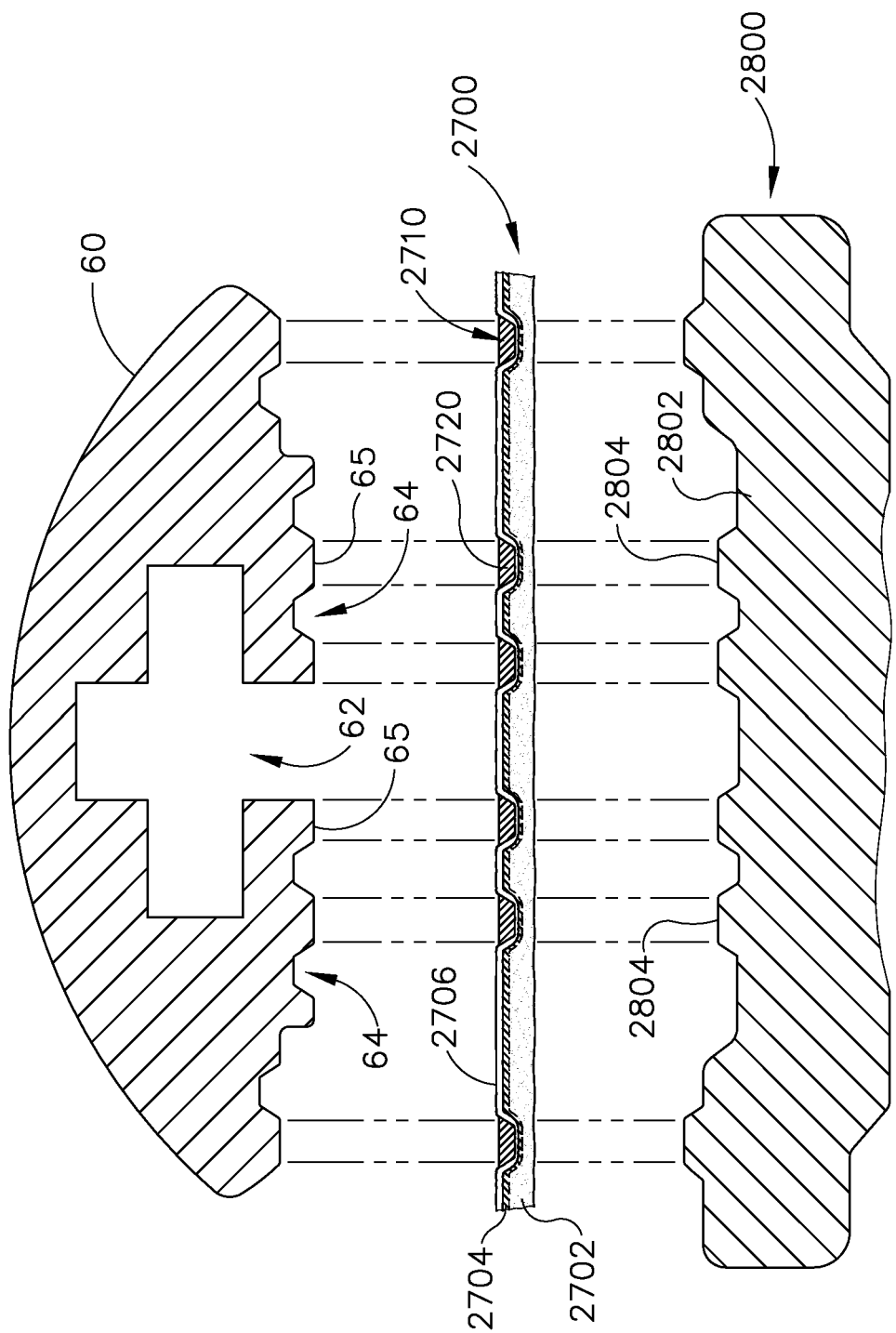
FIG. 44 depicts an exploded cross-sectional view of the buttress assembly of FIG. 43C between an exemplary retainer and the anvil of the end effector of FIG. 3.

As another merely illustrative variation, a buttress body may define a plurality of pockets that are configured to contain a flowable adhesive material in the form of discrete droplets. FIGS. 43A-44 show an exemplary buttress assembly (2700) that provides such structure and functionality. In particular, FIG. 43A shows buttress assembly (2700) in a first state of manufacture, where an impermeable layer (2704) is laid over a buttress body (2702). Various suitable materials that may be used to form impermeable layer (2704) and buttress body (2702) will be apparent to those of ordinary skill in the art in view of the teachings herein. As shown in FIG. 43B, impermeable layer (2704) of this example is absorbed into the upper region of buttress body (2702) to provide a surface coating. By way of example only, impermeable layer (2704) may be provided initially in a liquid form, such that buttress body (2702) soaks in the liquid; then the liquid soon cures to form an absorbed impermeable layer and surface coating. Again, various suitable materials and techniques that may be used to provide this structure and operability will be apparent to those of ordinary skill in the art in view of the teachings herein. After impermeable layer (2704) has been sufficiently absorbed, a heated stamping member (2750) is driven into buttress assembly (2700) as shown in FIG. 43C, forming a recess (2710) that stays formed after stamping member (2750) is removed. In the present example, one or more heated stamping members (2750) are used to form several recesses (2710) in buttress assembly (2700), as shown in FIG. 44.

Recesses (2710) are sized and positioned to correspond with regions of underside (65) of anvil (60) that are located between staple forming pockets (64). In some versions, each recess (2710) is formed as a longitudinally extending trough or channel that extends along nearly the full length of buttress assembly (2700). In some other versions, recesses (2700) are provided in linearly extending arrays, similar to the arrangement of droplets of adhesive material (2010) described above with reference to FIGS. 36-37. Other suitable configurations and arrangements will be apparent to those of ordinary skill in the art in view of the teachings herein. After recesses (2710) are formed, a flowable adhesive material (2720) is deposited into each recess (2710). By way of example only, flowable adhesive material (2720) may be injected into recesses (2710) as described above. In some versions, a flat impermeable peel-away film is laid over flowable adhesive material (2720) and buttress body (2702), containing flowable adhesive material (2720) in the pockets recesses (2710)). In some other versions, such peel-away film also defines a plurality of pockets that are configured to cooperate with recesses (2710) to contain flowable adhesive material (2720) in the form of discrete droplets that extend above the plane of the upper surface (2706) of buttress assembly (2700).

FIG. 44 shows adhesive assembly (2700) with adhesive material (2720) interposed between anvil (60) and retainer (2800). Retainer (2800) of this example has an upper surface (2802) comprising a plurality of upwardly extending projections (2804) that are positioned to correspond with the positions of recesses (2710) and the regions of underside (65) of anvil (60) that are located between staple forming pockets (64). Such projections (2804) may thus be configured to provide focused pressure to regions of buttress assembly (2700) the regions of underside (65) of anvil (60) that are located between staple forming pockets (64) when anvil (60) is driven to a closed position against buttress assembly (2700) and retainer (2800), thereby further promoting adhesion of flowable adhesive material (2720) to underside (65).

As described above, buttress assembly (2700) provides positioning of flowable adhesive material (2720) at the regions of underside (65) of anvil (60) that are located between staple forming pockets (64). In some other variations, buttress assembly (2700) provides positioning of flowable adhesive material (2720) at the regions of underside (65) of anvil (60) that correspond with staple forming pockets (64). It should be understood that other examples described herein as positioning an adhesive at regions corresponding with staple forming pockets (64) may be conversely varied. In other words, instead of positioning the adhesive at regions corresponding with staple forming pockets (64), such versions may position the adhesive at the regions of underside (65) that are located between staple forming pockets (64). Other suitable locations on underside (65) where adhesive may be positioned will be apparent to those of ordinary skill in the art in view of the teachings herein.

Those of ordinary skill in the art will recognize that some surgical procedures may require end effector (40) to be actuated several times during a single surgical procedure. In settings where staple cartridge (70) may only be used for a single actuation, this may require end effector (40) to be withdrawn from the patient to replace a spent staple cartridge (70) with a new staple cartridge (70). At this stage, before end effector (40) is inserted back into the patient for the next actuation, the operator may also reload end effector with one or more new buttress assemblies. After this process is repeated a certain number of times, some adhesive material may begin to build up on anvil (60). It may therefore be desirable to clean anvil (60) at some point during the surgical procedure. To facilitate such cleaning, the adhesive material may be water soluble. In such instances, the operator may simply swish end effector (40) in water or hold end effector (40) under flowing water to clean built-up adhesive material from anvil (60). In addition or in the alternative, a brush and/or other kind of cleaning implement may be used to provide mechanical agitation to thereby clean built-up adhesive material from anvil (60). Other suitable ways in which anvil (60) may be cleaned will be apparent to those of ordinary skill in the art in view of the teachings herein.

I. Exemplary Surgical Staple Buttress with Integral Attachment and Reinforcement Features In some instances, it may be desirable to integrate attachment and reinforcement features into buttress body (102), in addition to or as an alternative to having one or more adhesive layers (104, 106) on upper or lower surfaces of buttress body (102). Such integral attachment and reinforcement features may enhance the attachment and reinforcement of buttress body (102) relative to tissue (90), relative to deck (73) of staple cartridge (70) and/or relative to underside (65) of anvil (60). The below examples include various exemplary configurations through which one or more attachment and reinforcement features may be combined with a buttress body (102) to enhance the attachment and reinforcement of buttress body (102) relative to tissue (90), relative to deck (73) of staple cartridge (70) and/or relative to underside (65) of anvil (60). In the present example, it is contemplated that the adhesive materials comprise a synthetic based polymer such as those referred to herein. By way of example only, an adhesive material composition that may be used in the below example may include a 65/35 a copolymer of caprolactone and glycolide (PCL/PGA) having a low inherent viscosity (IV) and low crystallinity. Other suitable compositions will be apparent to those of ordinary skill in the art in view of the teachings herein. It should also be understood that naturally based polymers may be incorporated with the below teachings.

1. Exemplary Buttress Assembly with Post-Stapling Adhesive Flow

Figure 45:
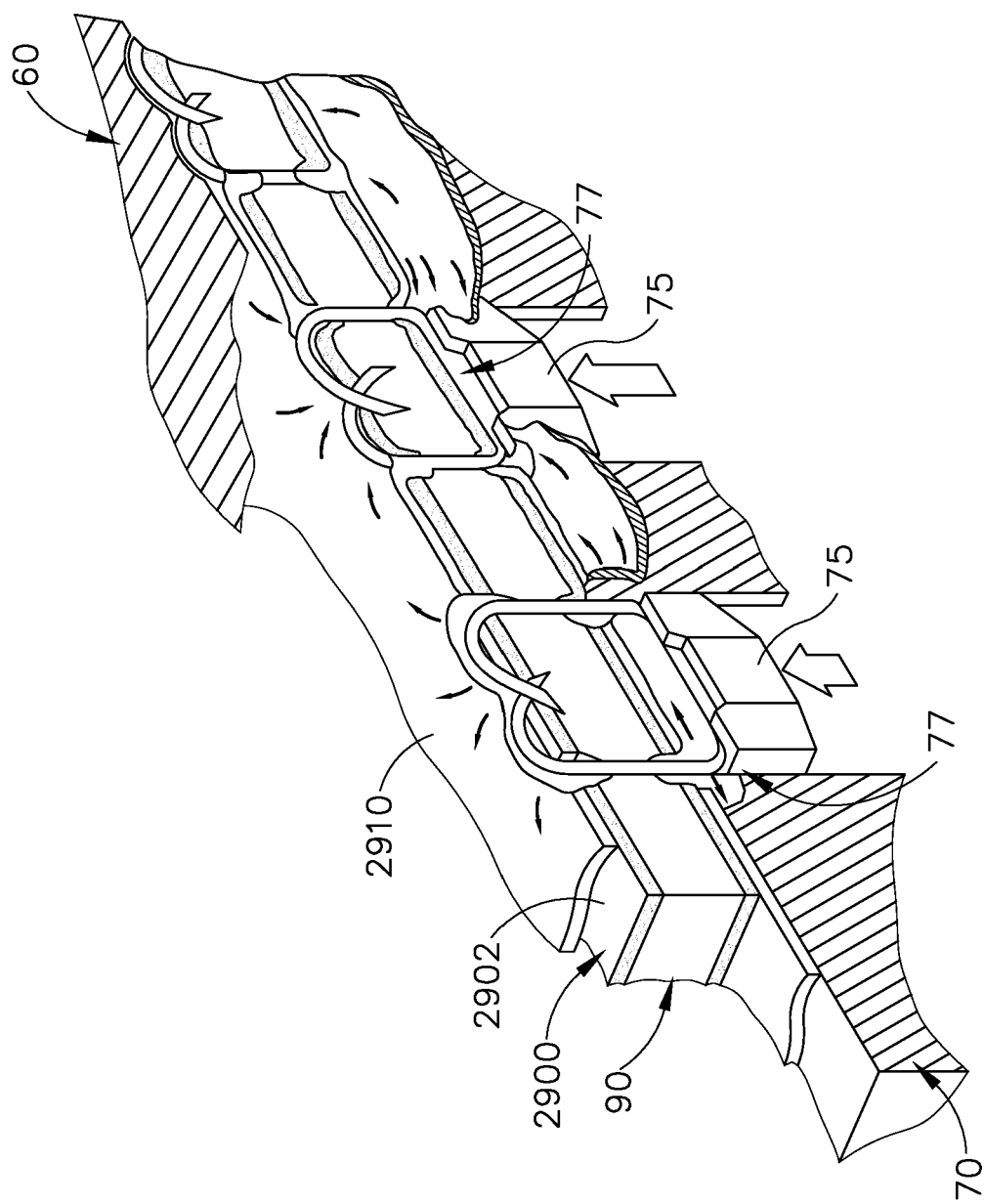
FIG. 45 depicts a perspective cross-sectional view of staples being driven through tissue and a buttress assembly.
Figure 46A:
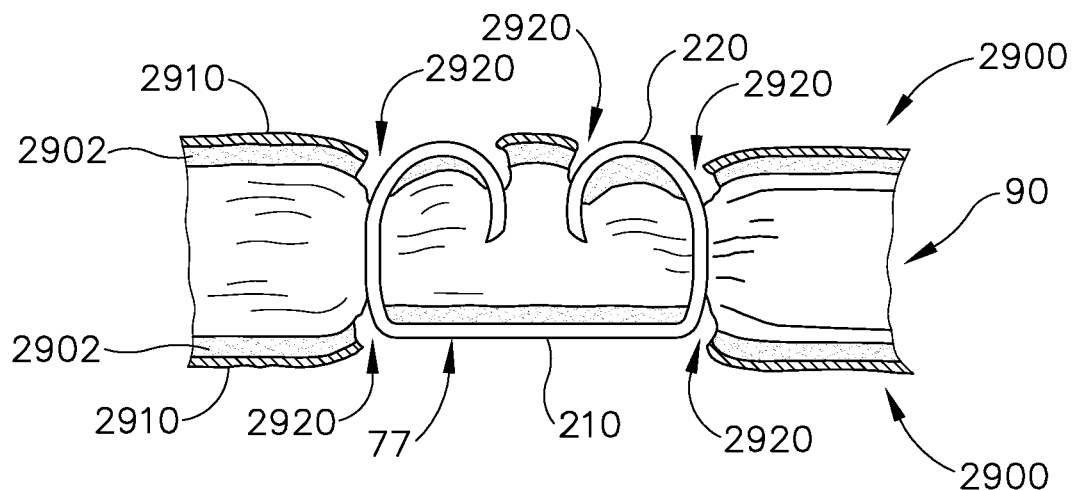
FIG. 46A depicts a perspective cross-sectional view of a staple driven through tissue and a buttress assembly, at a stage immediately after the staple has been driven through the tissue and buttress assembly.
Figure 46B:
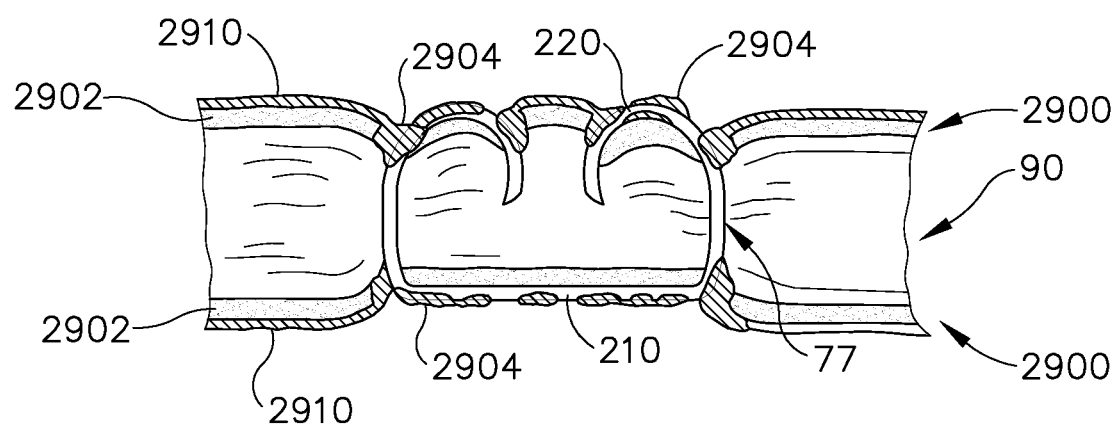
FIG. 46B depicts a perspective cross-sectional view of a staple driven through tissue and a buttress assembly, at a stage where an adjunct material has migrated into gaps around the staple legs.

FIGS. 45-46B show an exemplary buttress assembly (2900) that comprises a buttress body (2902) that contains an adhesive adjunct material (2904). Adhesive adjunct material (2904) may have a low viscosity enabling adhesive adjunct material (2904) to flow out of buttress body (2902) when buttress body (2902) is compressed. Various suitable compositions that may be used to provide adhesive adjunct material (2904) will be apparent to those of ordinary skill in the art in view of the teachings herein. Buttress body (2902) may have a fibrous structure, porous structure, and/or any other suitable kind of structure that is configured to absorb or otherwise contain adhesive adjunct material (2904). Various suitable materials and structures that may be used to provide buttress body (2902) will be apparent to those of ordinary skill in the art in view of the teachings herein.

A pressure sensitive, impermeable adhesive film (2910) is secured to one surface of buttress body (2902). Being impermeable, adhesive film (2910) is configured to prevent adhesive adjunct material (2904) from flowing out of that surface of buttress body (2902). Adhesive film (2910) is also configured to removably secure buttress assembly (2900) to underside (65) of anvil (60) or deck (73) of staple cartridge (70). In particular, adhesive film (2910) includes a pressure sensitive adhesive that provides enough adhesive strength to temporarily secure buttress assembly (2900) to underside (65) of anvil (60) or deck (73) of staple cartridge (70); yet the pressure sensitive adhesive also permits adhesive film (2910) to be pulled off of underside (65) of anvil (60) or deck (73) of staple cartridge (70) after end effector (40) has been actuated and staples (77) have been driven through buttress assembly (2900). Various suitable materials that may be used to form adhesive film (2910) will be apparent to those of ordinary skill in the art in view of the teachings herein. Similarly, various suitable materials that may be used to provide a pressure sensitive adhesive on or in adhesive film (2910) will be apparent to those of ordinary skill in the art in view of the teachings herein.

It should be understood that, when buttress assembly (2900) is loaded on retainer (300), the surface of upper side (302) or lower side (304) (depending on which side buttress assembly (2900) is loaded onto) may prevent adhesive adjunct material (2904) from flowing out of the surface of buttress body (2902) that is opposite to adhesive film (2910). FIGS. 45-46B show two buttress assemblies (2900), such that one buttress assembly (2900) would have been loaded onto upper side (302) of retainer (300) while the other buttress assembly (2900) would have been loaded onto lower side (304) of retainer (300). FIG. 45 in particular shows stapler drivers (75) driving staples (77) through tissue (90) and through both buttress assemblies (2900) as end effector (40) is being actuated. As shown in FIG. 46A, when staple (77) is initially driven through tissue (90) and buttress assemblies (2900), legs (220) of staple (77) tear through film (2910), creating gaps (2920) around crown (210) and staple legs (220). These gaps (2920) provide a path for adhesive adjunct material (2904) to flow out of buttress body (2902). Moreover, the series of applied staples (77) compress buttress assemblies (2900) against tissue (90), thereby urging adhesive adjunct material (2904) out of buttress body (2902) and into gaps (2920) as shown in FIG. 46B. This expelled adhesive adjunct material (2904) flows onto crown (210) and regions of legs (220) that would otherwise be exposed. The expelled adhesive adjunct material (2904) may eventually cure and thereby further reinforce the structural integrity of the applied buttress assembly (2900); and/or further reinforce the attachment of staples (77) to buttress assemblies (2900). The expelled adhesive adjunct material (2904) may also provide a hemostatic effect by blocking the flow of blood that might otherwise occur through gaps (2920).

In some variations of buttress assembly (2900), the adhesive adjunct material (2904) is provided in a layer that is laid over buttress body (2902) (in addition to or in lieu of being absorbed in or otherwise contained in buttress body (2902)). For instance, the adhesive adjunct material (2904) may be provided in a layer that is either used to replace impermeable adhesive film (2910) or in a layer that is interposed between buttress body (2902) and impermeable adhesive film (2910). Other suitable configurations will be apparent to those of ordinary skill in the art in view of the teachings herein.

2. Exemplary Buttress Assembly with Integral Fastening Strands

Figure 47:
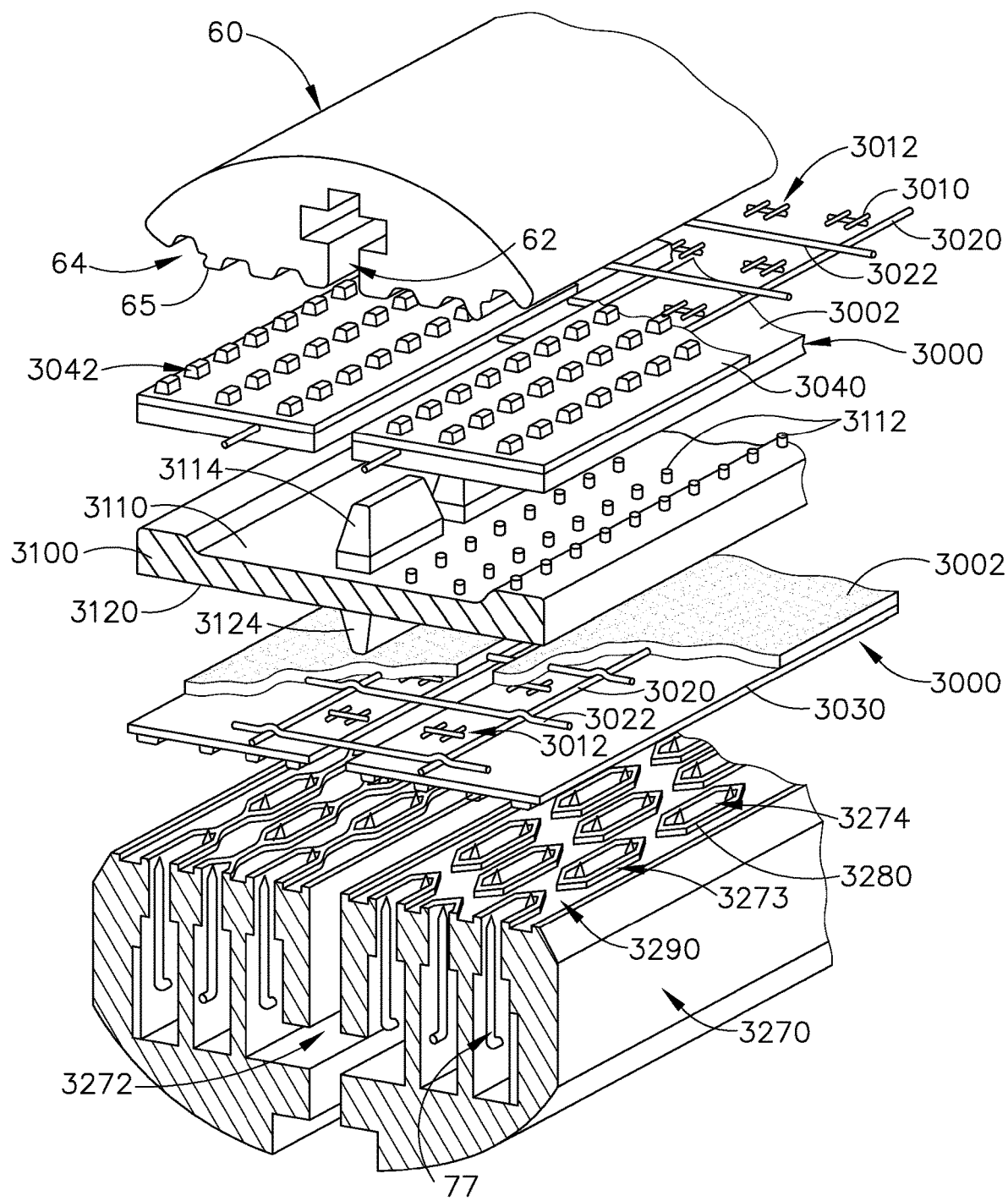
FIG. 47 depicts an exploded, perspective cross-sectional view of an exemplary end effector assembly, retainer, and pair of buttress assemblies.
Figure 48:
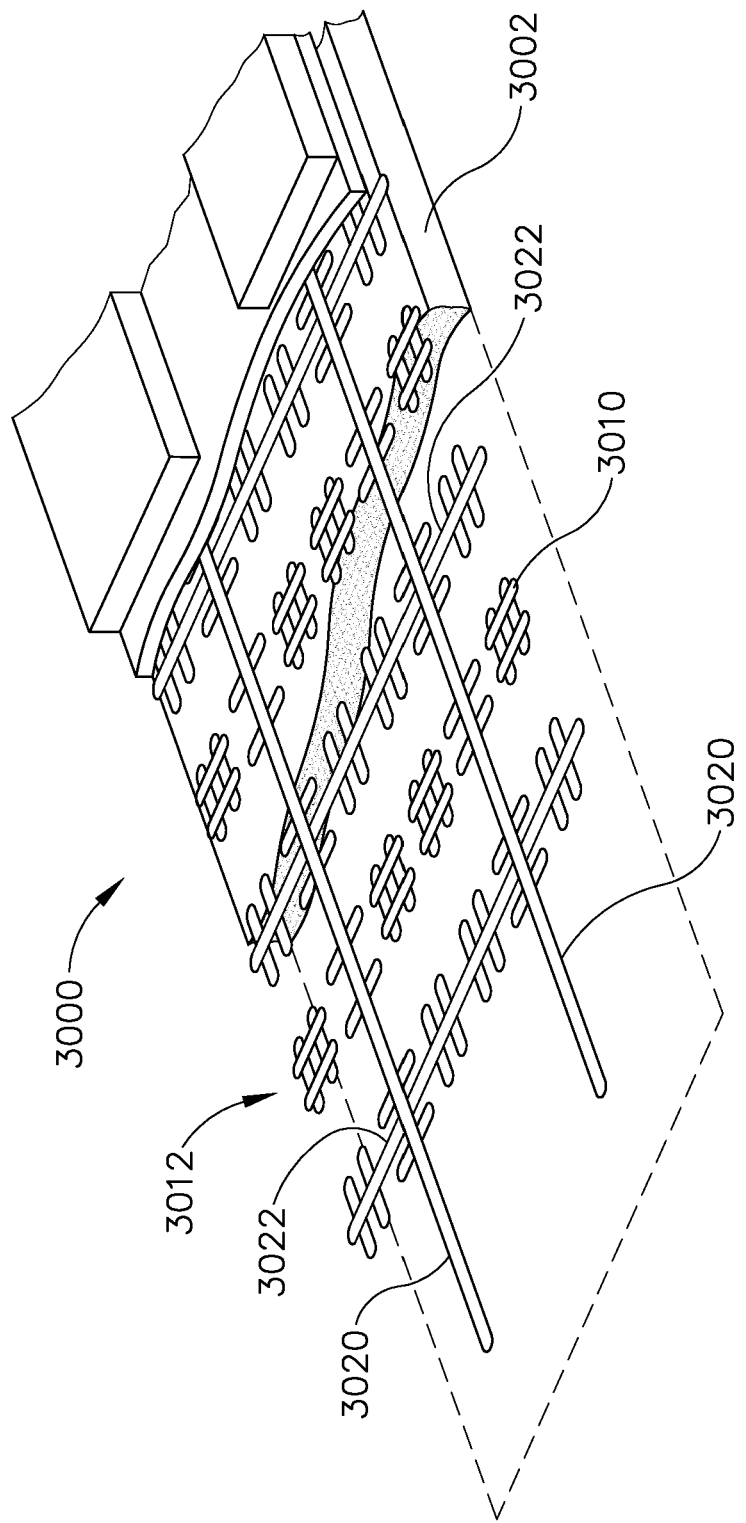
FIG. 48 depicts a partial perspective view of one of the buttress assemblies of FIG. 47.

FIGS. 47-51 show another exemplary buttress assembly (3000) with an exemplary alternative retainer (3100). Two buttress assemblies (3000) are shown, including one buttress assembly (3000) that is positioned to attach to underside (65) of anvil (60) and another buttress assembly (300) that is positioned to attach to a deck (3273) of a staple cartridge (3270). As best seen in FIG. 48, each buttress assembly (3000) of this example comprises a buttress body (3002) with a set of fastening strands (3010) woven therethrough. Buttress body (3002) may be configured and operable in accordance with any of the various buttress bodies referred to herein. By way of example only, fastening strands (3010) may comprise VICRYL® (polyglactin 910) suture material by Ethicon US, LLC. Alternatively, any other suitable material(s) may be used. In the present example, strands (3010) are provided only in a series of small, discrete woven regions (3012). In other words, strands (3010) are not woven throughout the entire buttress body (3002) in this example. The discrete woven regions (3012) of strands (3010) are positioned at locations where staples (77) will be driven through buttress assembly (3000), as will be described in greater detail below. In some other versions, strands (3010) are woven throughout the entire buttress body (3002) or in some other arrangement.

As also shown in FIG. 48, buttress assembly (3000) further includes a set of reinforcement members (3020, 3022). Reinforcement members (3020, 3022) may also comprise VICRYL® (polyglactin 910) suture material and/or any other suitable material(s). Each reinforcement member (3020) extends longitudinally along the full length of buttress body (3002). Reinforcement members (3022) extend transversely across the full width of buttress body (3002). Reinforcement members (3022) also span a gap (3004) defined between a pair of buttress bodies (3002), providing a connection of buttress bodies (3002) across gap (3004). In some versions, reinforcement members (3020, 3022) pass through discrete woven regions (3012) of strands (3010), such that reinforcement members (3020, 3022) are included in the weave at some of the discrete woven region (3012). In addition or in the alternative, reinforcement members (3020, 3022) may themselves be at least partially woven through buttress bodies (3002).

Figure 49:
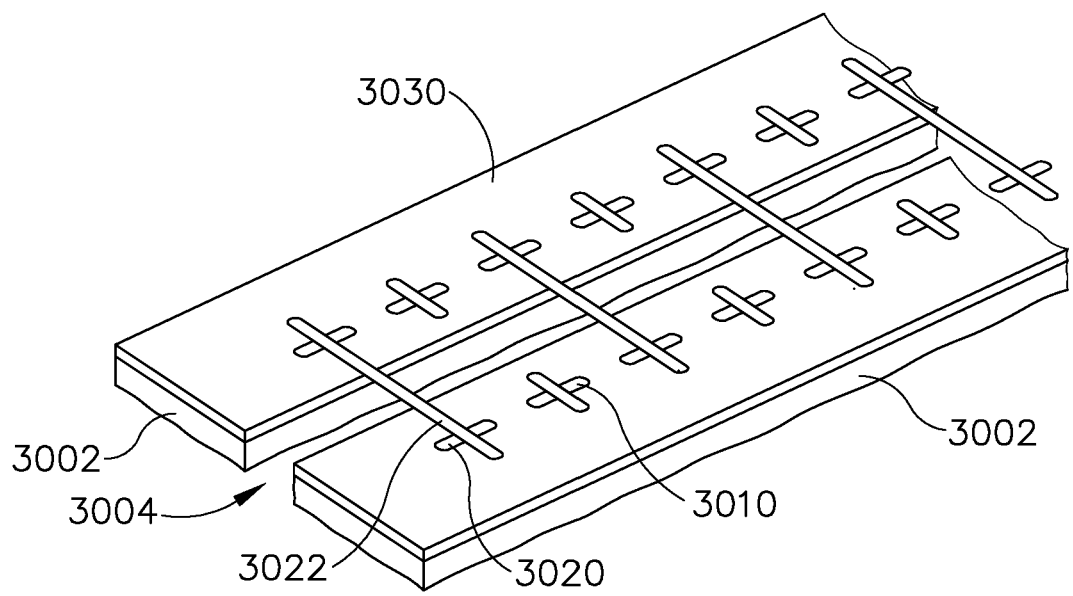
FIG. 49 depicts a perspective view of some elements of one of the buttress assemblies of FIG. 47.

As best seen in FIG. 49, buttress assembly (3000) further includes an impermeable layer (3030) laid over buttress body (3002). In the present example, strands (3010) and reinforcement members (3022) are partially woven through impermeable layer (3030); while reinforcement member members (3022) are positioned over impermeable layer (3030). In some other versions, impermeable layer (3030) is substituted with a semi impermeable layer, such as a layer of polydioxanone (PDS) and/or some other material(s). Various suitable materials that may be used to form impermeable layer (3030) (or a semi impermeable substitute therefor) will be apparent to those of ordinary skill in the art in view of the teachings herein.

Figure 50:
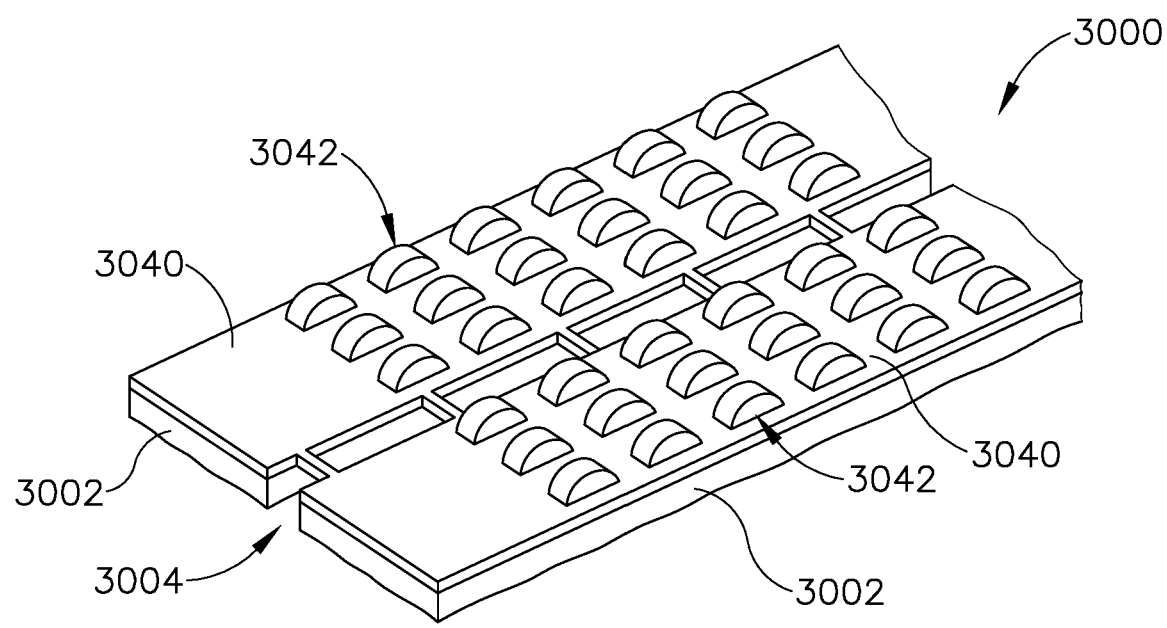
FIG. 50 depicts a perspective view of an assembled form of one of the buttress assemblies of FIG. 47.

As best seen in FIG. 50, buttress assembly (3000) further includes an impermeable peel-away film (3040) laid over impermeable layer (3030). Peel-away film (3040) defines a plurality of pockets (3042) that are configured to retain a flowable adhesive material (3050) (shown in FIG. 51) in an array of discretely formed droplets on impermeable layer (3030). Peel-away film (3040) is configured to adhere to impermeable layer (3030) during storage and transport of buttress assembly (3000), but may be peeled away to expose the flowable adhesive material (3050) under pockets (3042) right before buttress assembly (3000) is installed on end effector (40). The discrete droplets of adhesive material (3050) are sized and positioned to correspond with the positioning of staple forming pockets (64) of anvil (60). Thus, the discrete droplets of adhesive material (3050) and pockets (3042) are arranged in three longitudinally extending linear arrays. Alternatively, any other suitable arrangement may be used. Various suitable materials that may be used to form peel-away film (3040) will be apparent to those of ordinary skill in the art in view of the teachings herein.

Referring back to FIG. 47, retainer (3100) has an upper surface (3110) and a lower surface (3120). A first pair of buttress assemblies (3000) are positioned on upper surface (3110) for adhesion of those buttress assemblies (3000) to underside (65) of anvil (60). A second pair of buttress assemblies (3000) are positioned on lower surface (3120) for adhesion of those buttress assemblies (3000) to deck (3273) of staple cartridge (3270). Upper surface (3110) includes an upwardly projecting, longitudinally extending rib (3114). Rib (3114) is sized to complement channel (62) of anvil (60). Lower surface (3120) also includes a downwardly projecting, longitudinally extending rib (3124), which is sized to complement channel (3272) of staple cartridge (3270). When anvil (60) is moved to a closed position to compress retainer (3100) and buttress assemblies (3000) between anvil (60) and staple cartridge (3270), ribs (3114, 3124) enter corresponding channels (62, 3472) and prevent flowable adhesive material (3050) from entering channels (62, 3472). Ribs (3114, 3124) may also ensure proper lateral alignment of retainer (3100) and buttress bodies (3000) with anvil (60) and staple cartridge (3270).

Upper surface (3110) of the present example further includes a plurality of upwardly extending projections (3112). While projections (3112) are only shown on one side of rib (3114), it should be understood that projections (3112) may also be located on the other side of rib (3114). Projections (3112) are configured and positioned to correspond with staple forming pockets (64) on underside (65) of anvil (60); and pockets (3042) of peel-away film (3040). When anvil (60) is moved to a closed position to compress retainer (3100) and buttress assemblies (3000) between anvil (60) and staple cartridge (3270), projections (3112) are configured to provide focused pressure to regions of buttress bodies (3002) at regions corresponding to staple forming pockets (64) the droplets of adhesive material (3050) formed by pockets (3042). While not shown, it should be understood that lower surface (3120) may also include downwardly extending projections, similar to projections (3112), to provide focused pressure to selected regions of buttress bodies (3002).

As also shown in FIG. 47, staple cartridge (3270) of the present example is substantially similar to staple cartridge (70) in that staple cartridge (3270) of this example includes channel (3272) and staple pockets (3274). However, staple cartridge (3270) of this example differs from staple cartridge (70) in that staple cartridge (3270) of this example includes upwardly extending walls (3280) that surround each staple pocket (3274), the outer edges of deck (3273), and the edges of deck (3273) adjacent to channel (3272). Walls (3280) thus define troughs (3290) that are configured to prevent adhesive material (3050) from flowing into staple pockets (3274), over the outer edges of deck (3273), and into channel (3272). In some other variations, staple cartridge (3270) is simply substituted with staple cartridge (70) or some other kind of staple cartridge.

Figure 51:
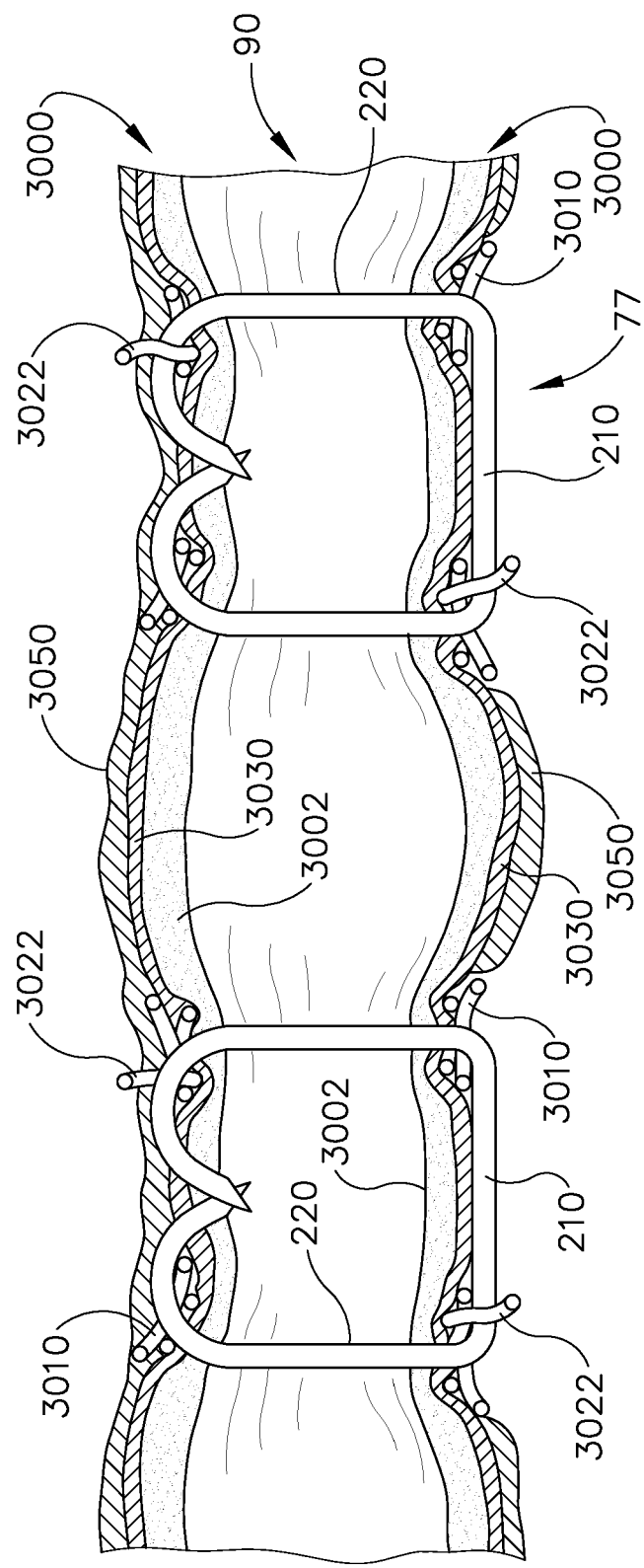
FIG. 51 depicts a cross-sectional view of staples driven through tissue and the buttress assemblies of FIG. 47.

FIG. 51 shows tissue (90) after an end effector formed by anvil (60) and staple cartridge (3270) has been actuated through the tissue (90). As shown, staples (77) secure buttress assemblies (3000) to the tissue (90). Crown (210) and legs (220) of each staple (77) capture strands (3010) and reinforcement members (3022), providing an attachment that may be more secure than what might otherwise be provided if buttress body (3002) lacked strands (3010) and reinforcement members (3022). It should be understood that, when firing beam (82) is advanced distally during actuation of the end effector, knife member (80) severs the portions of reinforcement members (3022) that span across gap (3004).

As is also shown in FIG. 51, some of the adhesive material (3050) remains on impermeable layer (3030). In some instances, this adhesive material (3050) may flow into gaps that might otherwise be present adjacent to crowns (210) and/or legs (220). The adhesive material (3050) may thus further reinforce the structural integrity of the applied buttress assembly (3000); and/or further reinforce the attachment of staples (77) to buttress assemblies (3000). The adhesive material (3050) may also provide a hemostatic effect by blocking the flow of blood that might otherwise occur through gaps that might otherwise be present adjacent to crowns (210) and/or legs (220). In some other variations, buttress assemblies (3000) are configured such that an appreciable amount of adhesive material (3000) is no longer present on impermeable layer (3030) after staples (77) are fired. Other suitable arrangements and compositions will be apparent to those of ordinary skill in the art in view of the teachings herein.

3. Exemplary Buttress Assembly with Heat Sensitive Strands

Figure 52:
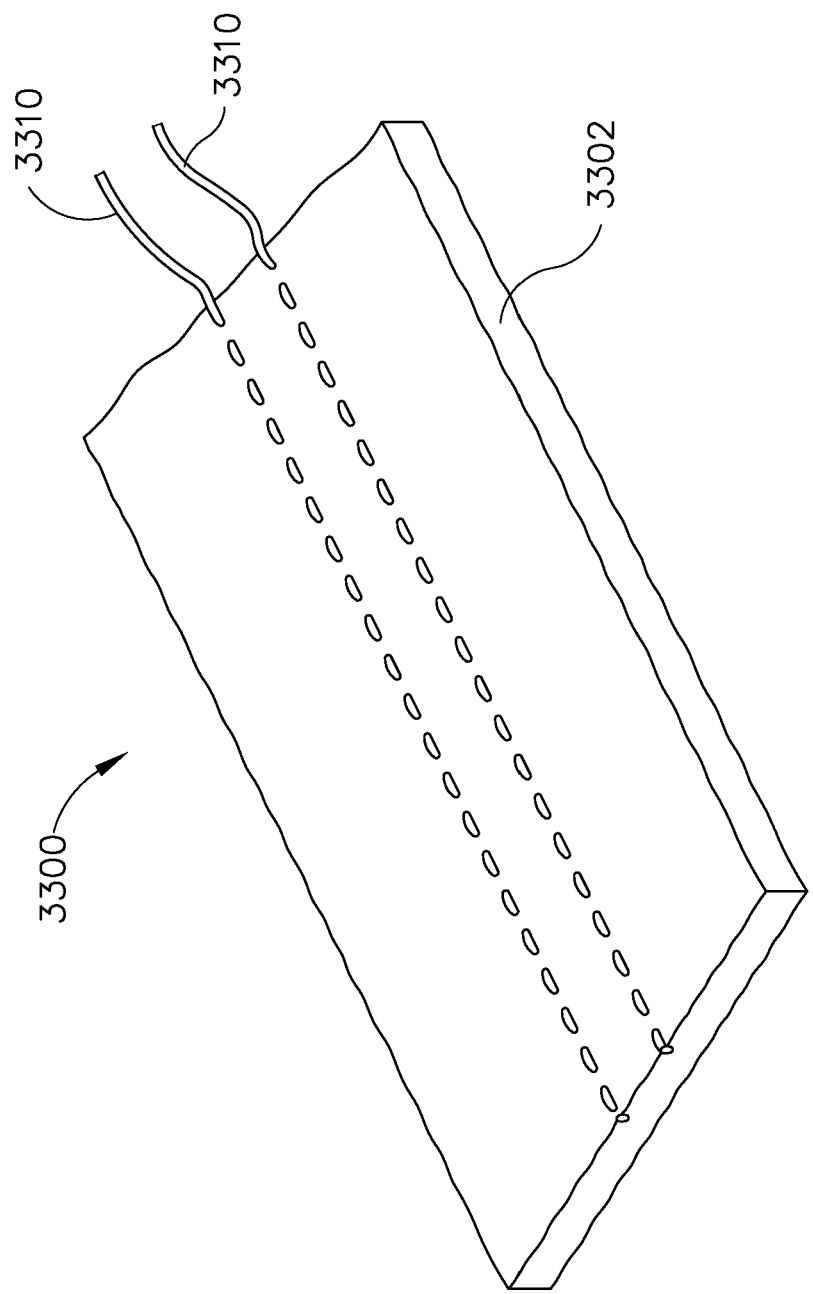
FIG. 52 depicts a perspective view of an exemplary alternative buttress assembly.
Figure 53:
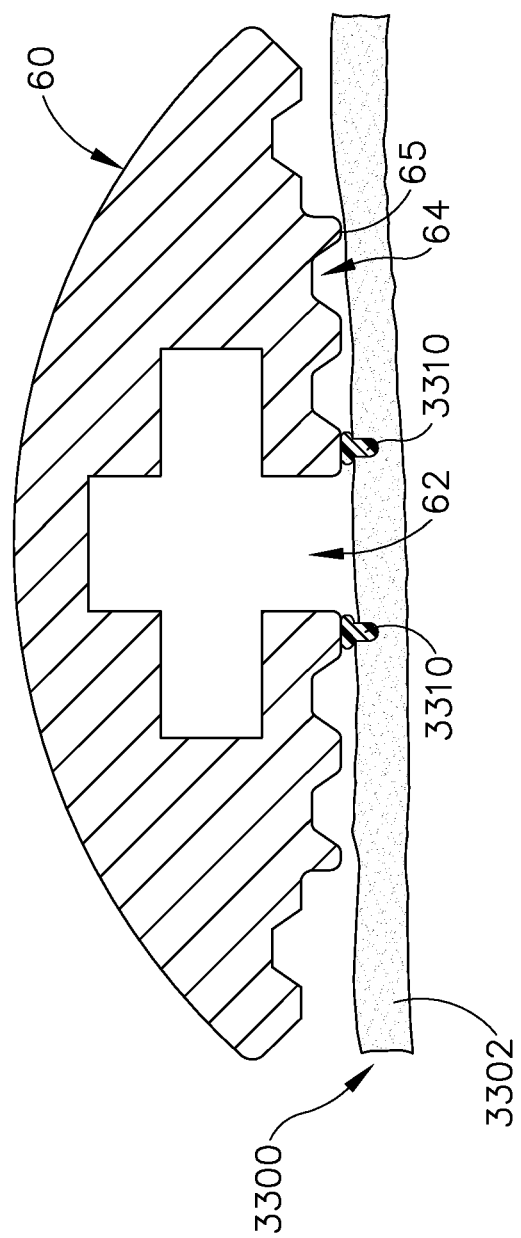
FIG. 53 depicts a cross-sectional end view of the buttress assembly of FIG. 52 applied to the anvil of the end effector of FIG. 3.
Figure 54:
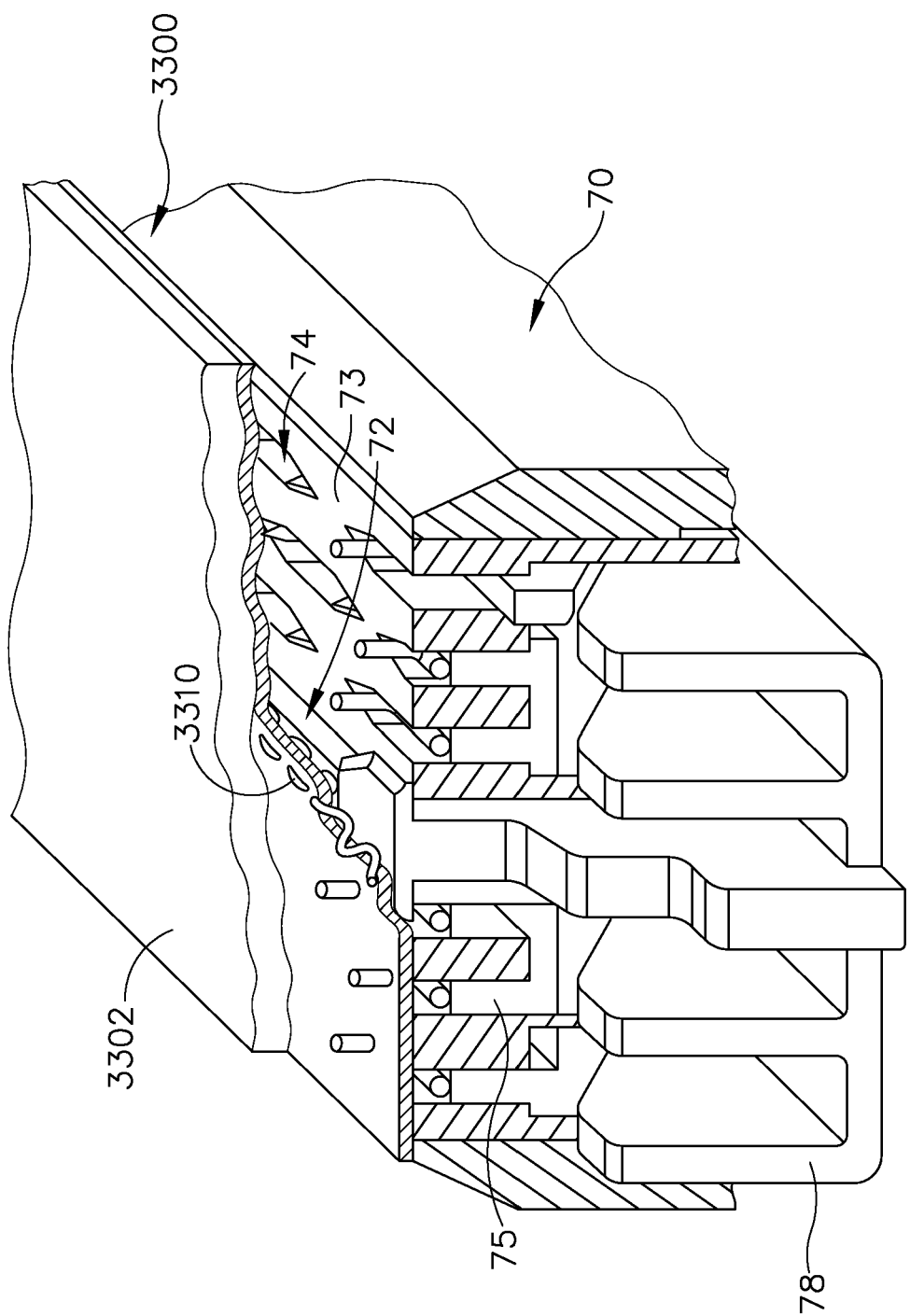
FIG. 54 depicts a partial, cross-sectional perspective view of the buttress assembly of FIG. 52 applied to the deck of the staple cartridge of the end effector of FIG. 3.

FIGS. 52-54 show another exemplary buttress assembly (3300). Buttress assembly (3300) of this example comprises a buttress body (3302) with a pair of heat sensitive strands (3310) woven through buttress body (3302). Buttress body (3302) may be formed in accordance with any buttress body referred to herein. Each heat sensitive strand (3310) is woven through buttress body (3302) such that heat sensitive strand (3310) extends along the full length of buttress body (3302). Heat sensitive strands (3310) are parallel to each other and are spaced apart by a distance complementing the lateral width of channels (62, 72). Heat sensitive strands (3310) are formed of a material that will melt at a relatively low temperature and adhere to a surface that it is in contact with when it melts and cools. The melting temperature (Tm) of heat sensitive strands (3310) is lower than the melting temperature (Tm) of buttress body (3302).

By way of example only, heat sensitive strands (3310) may comprise polydioxanone (PDS). In some such versions, buttress body (3302) comprises VICRYL® (polyglactin 910) material by Ethicon US, LLC, heat sensitive strands (3310) comprise polydioxanone (PDS), and buttress assembly (3300) is formed as a woven fleece material made from a 7:1 blend of VICRYL®:PDS that is heat treated to shrink polydioxanone (PDS) and bond individual fibers in the fleece together. Alternatively, any other suitable blend ratio may be used. In some versions where buttress assembly (3300) comprises a woven fleece material made from a blend of VICRYL® material and polydioxanone (PDS), the fleece may be attached to a polydioxanone (PDS) film that may be heated to secure buttress assembly (3300) to underside (65) of anvil (60) or deck (73) of staple cartridge (70).

As another merely illustrative example, buttress assembly (3300) may be constructed in accordance with at least some of the teachings of U.S. Pat. No. 5,686,090, entitled "Multi-Layered Implant," issued Nov. 11, 1997, the disclosure of which is incorporated by reference herein. Various other suitable materials that may be used to form heat sensitive strands (3310) will be apparent to those of ordinary skill in the art in view of the teachings herein. While buttress assembly (3300) only includes two heat sensitive strands (3310) in the depicted example, it should be understood that any other suitable number of heat sensitive strands (3310) may be incorporated into buttress assembly (3300) if desired.

FIG. 53 shows buttress assembly (3300) applied to underside (65) of anvil (60). As shown, heat sensitive strands (3310) are positioned on respective regions of underside (65) that are adjacent to channel (62). When buttress assembly (3300) is so positioned, heat sensitive strands (3310) may be heated to their melting point; then allowed to cool to thereby adhere buttress assembly (3300) to underside (65). By way of example only, buttress assembly (3300) may be applied to underside (65) using a modified version of retainer (300). For instance, such a modified version of retainer (300) may include a heating element at or under upper side (302). The heating element may be activated while anvil (60) is clamping down on buttress assembly (3300). Such a modified version of retainer (300) may also include a coating such as polytetrafluoroethylene (PTFE) to prevent heat sensitive strands (3310) from adhering to upper side (302). In addition or in the alternative, retainer (300) may include surface features that are configured to prevent heat sensitive strands (3310) from adhering to upper side (302). It should also be understood that heat sensitive strands (3310) may be woven through buttress body (3302) in such a way that heat sensitive strands (3310) will not contact upper side (302) of the modified retainer (300). Other suitable structures and techniques that may be used to provide heat to heat sensitive strands (3310) will be apparent to those of ordinary skill in the art in view of the teachings herein.

FIG. 54 shows buttress assembly (3300) applied to deck (73) of staple cartridge (70). As shown, heat sensitive strands (3310) are positioned on respective regions of deck (73) that are adjacent to channel (72). When buttress assembly (3300) is so positioned, heat sensitive strands (3310) may be heated to their melting point; then allowed to cool to thereby adhere buttress assembly (3300) to deck (73). By way of example only, buttress assembly (3300) may be applied to deck (73) using a modified version of retainer (300) as described above; or using any other suitable structures or techniques as will be apparent to those of ordinary skill in the art in view of the teachings herein.

4. Other Exemplary Buttress Assemblies

It should be understood that the adhesive material that removably secures a buttress body (102) to underside (65) of anvil (60) or to deck (73) of staple cartridge (70) may have various properties including malleability and tackiness that provides self-attachment to underside (65) of anvil (60) or to deck (73) of staple cartridge (70). In other words, the adhesive material may deform to the shape presented by the corresponding contact area of underside (65) or deck (73). It should also be understood that the adhesive material may be provided on buttress body (102) in various shapes and configurations. For instance, the adhesive material may be provided in a pattern that includes selective zones of adhesion to minimize the likelihood of collateral damage to areas such as staple pockets (74) whose performance might be adversely affected by influx of adhesive material. The pattern of the adhesive material may also minimize the number and size of the adhesive contact with underside (65) or deck (73), thereby minimizing the force required to pull buttress assembly (100) off of underside (65) or deck (73) after end effector (40) has been actuated. The geometry of the adhesive material may provide uniform thickness or variable thickness. The adhesive material may also provide variable stiffness. Providing a variable thickness and/or variable stiffness may provide a variable pressure distribution.

Figure 55:
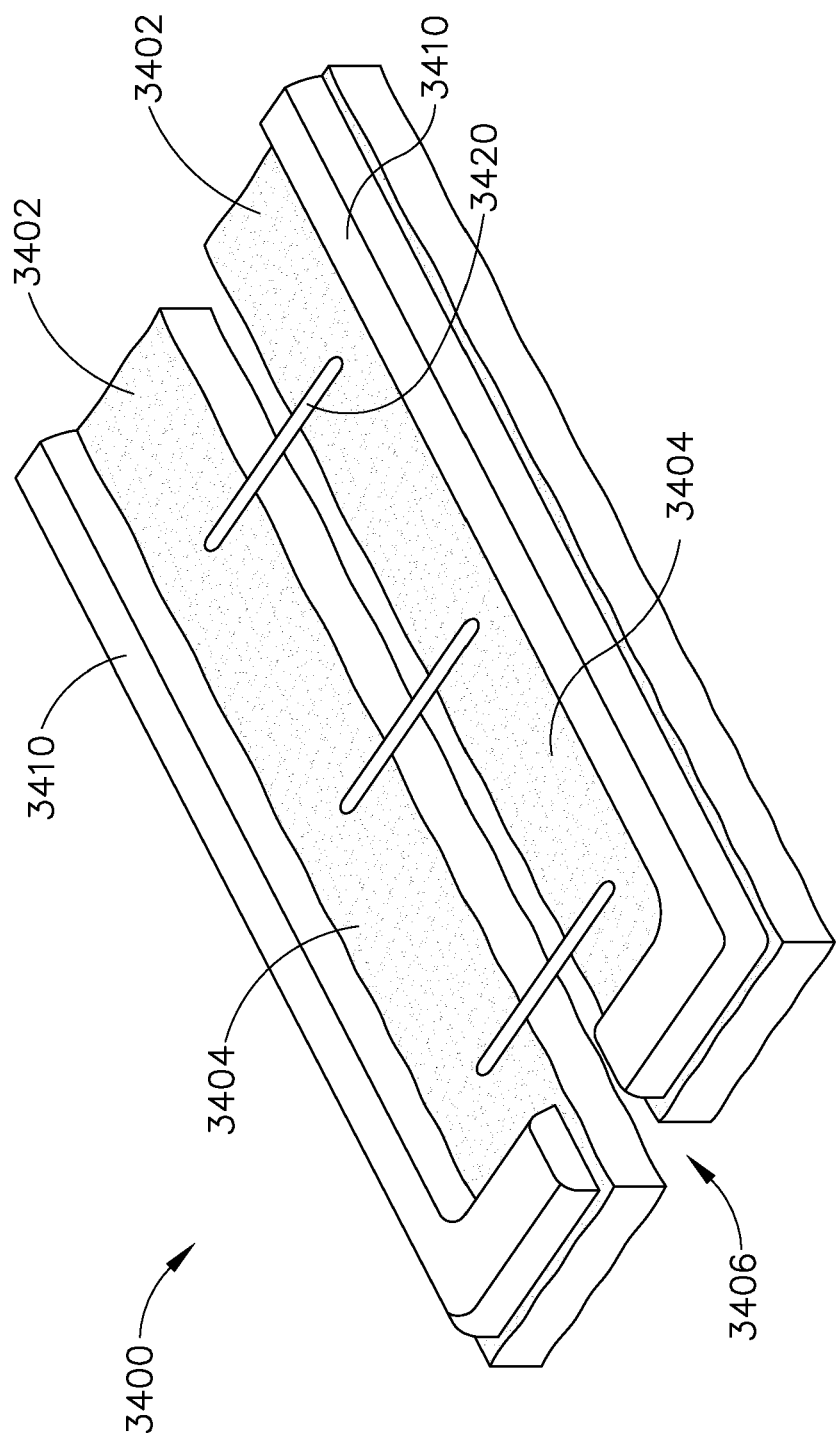
FIG. 55 depicts a perspective view of an exemplary alternative buttress assembly.

FIG. 55 shows an exemplary alternative buttress assembly (3400) that comprises a pair of buttress bodies (3402) and an adhesive material (3410) that is positioned along the outer perimeter of the upper surface (3404) of each buttress body (3402). Buttress bodies (3402) are separated by a gap (3406) that corresponds to channel (62) of anvil (60) and channel (72) of staple cartridge (70). A set of tethers (3420) extend transversely across gap (3406), connecting buttress bodies (3402). As described above with respect to other tethers, tethers (3420) of this example will be severed by knife member (80) when firing beam (82) is advanced distally during actuation of end effector (40). Due to the configuration and arrangement of adhesive material (3410), buttress assembly (3400) is only adhered to underside (65) or deck (73) along the outer perimeter of buttress body (3402), which may minimize the force required to pull buttress assembly (3400) off of underside (65) or deck (73) after end effector (40) has been actuated. Various suitable materials that may be used to form buttress bodies (3402), adhesive material (3410), and tethers (3420) will be apparent to those of ordinary skill in the art in view of the teachings herein.

Figure 56:
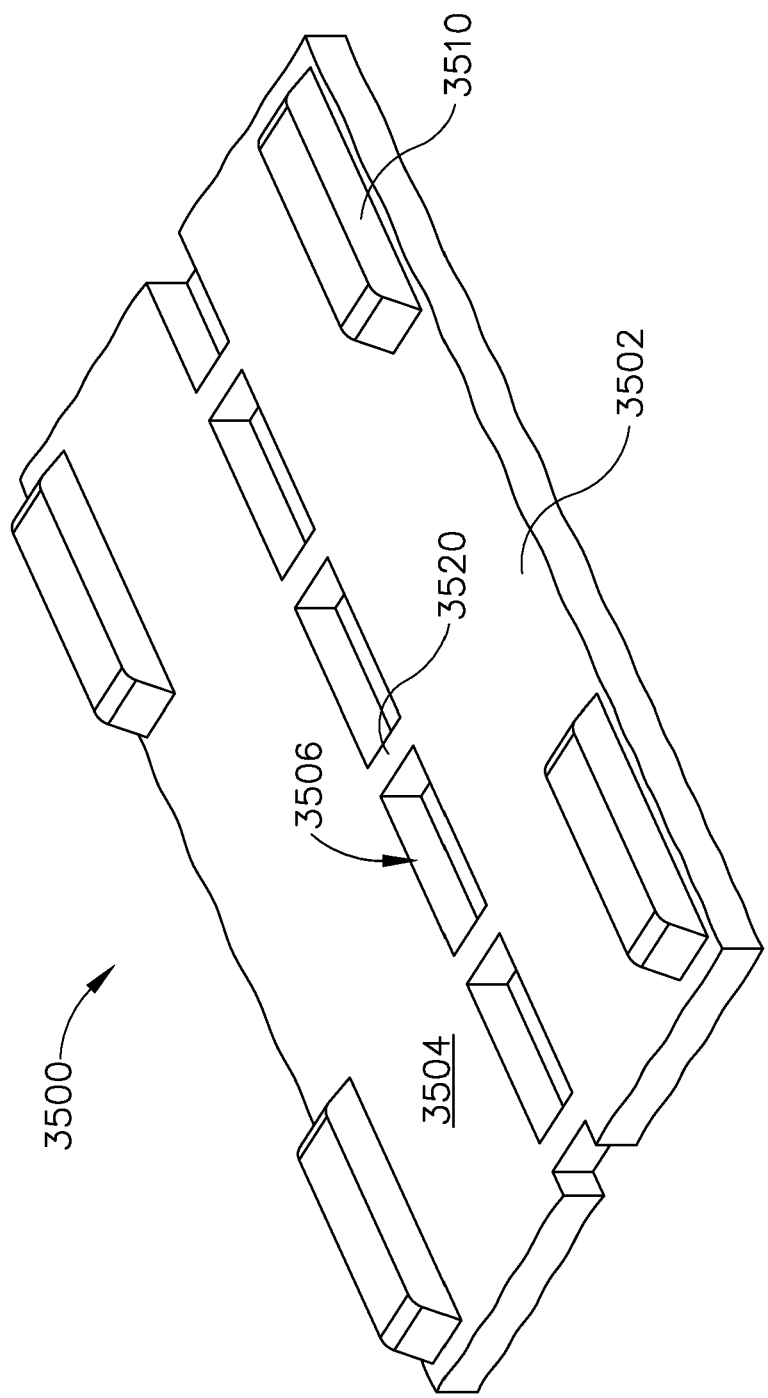
FIG. 56 depicts a perspective view of another exemplary alternative buttress assembly.

FIG. 56 shows another exemplary alternative buttress assembly (3500) that comprises a buttress body (3502) and an adhesive material (3510) that is positioned in discrete regions along the outer perimeter of the upper surface (3504) of buttress body (3502). Buttress body (3502) defines a longitudinally extending array of gaps (3506) that correspond to channel (62) of anvil (60) and channel (72) of staple cartridge (70). Buttress body (3502) further defines a set of transversely extending bridge regions (3520) that separate gaps (3506). As described above with respect to tethers, bridge regions (3520) of this example will be severed by knife member (80) when firing beam (82) is advanced distally during actuation of end effector (40). Due to the configuration and arrangement of adhesive material (3510), buttress assembly (3400) is only adhered to underside (65) or deck (73) at discrete regions along the outer perimeter of buttress body (3502), which may further minimize the force required to pull buttress assembly (3500) off of underside (65) or deck (73) after end effector (40) has been actuated. This pull-away force may be lower for buttress assembly (3500) than it is for buttress assembly (3400) since less adhesive material (3510) is used in buttress assembly (3500). Various suitable materials that may be used to form buttress body (3502) and adhesive material (3510) will be apparent to those of ordinary skill in the art in view of the teachings herein.

Figure 57:
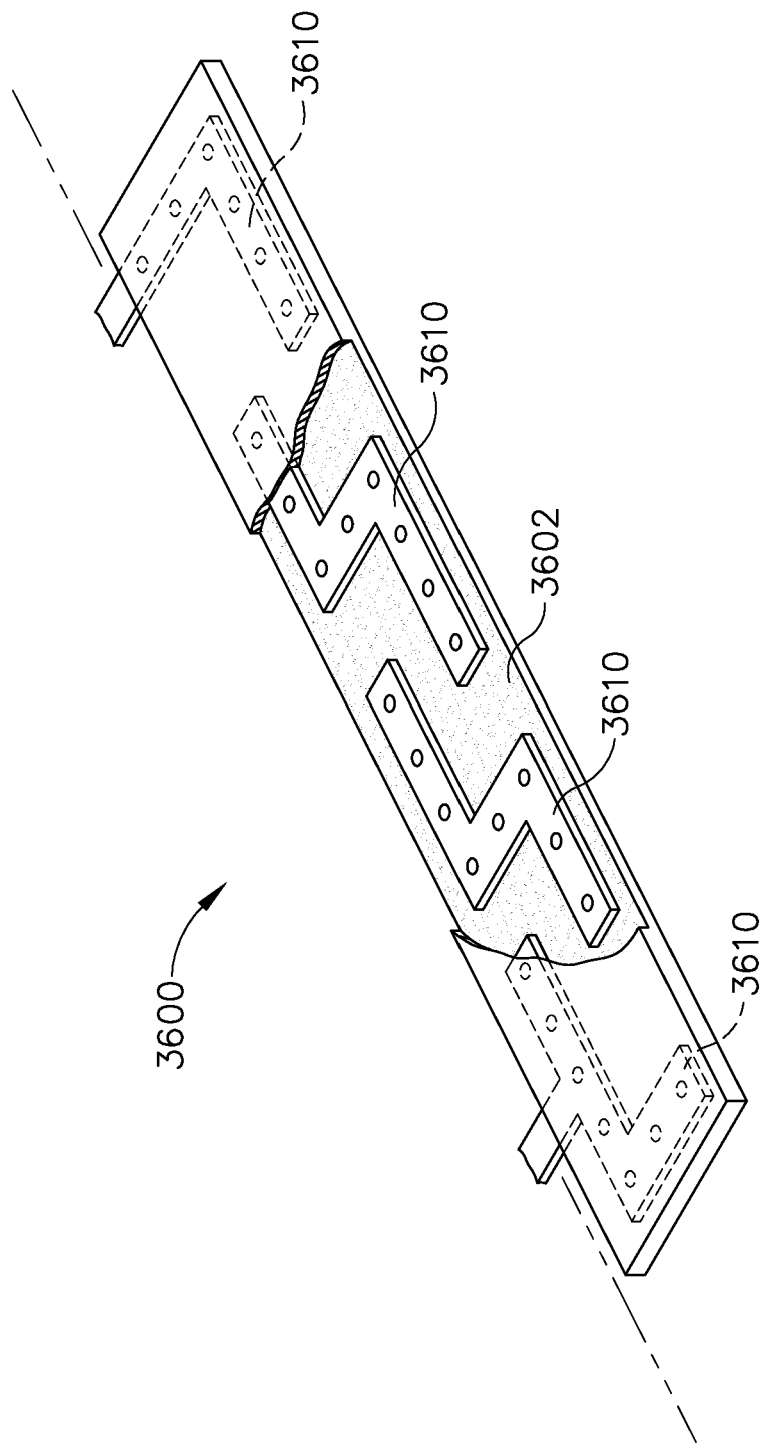
FIG. 57 depicts a perspective view of another exemplary alternative buttress assembly.

FIG. 57 shows yet another exemplary alternative buttress assembly (3600) that comprises a buttress body (3602) with a plurality of integral reinforcement members (3610). Buttress body (3602) may be configured and operable in accordance with any of the various buttress bodies described herein. An adhesive material (not shown) is incorporated into buttress body (3602) in order to provide removable attachment of buttress assembly (3600) to underside (65) of anvil (60) or deck (73) of staple cartridge (70). Various suitable compositions that may be used to provide the adhesive material, and various suitable ways in which such adhesive material may be incorporated into buttress body (3602), will be apparent to those of ordinary skill in the art in view of the teachings herein.

Reinforcement members (3610) are configured to provide structural reinforcement to buttress body (3602) and/or to the attachment of staples (77) that are driven through buttress assembly (3600). By way of example only, in some versions buttress body (3602) is formed of a porous sponge like material while reinforcement members (3610) are formed of a tight fibrous weave that has greater tensile strength than the material forming buttress body (3602). Various suitable materials and structures that may be used to form reinforcement members (3610) will be apparent to those of ordinary skill in the art in view of the teachings herein. In the present example, two of the reinforcement members (3610) have a generally "S" shaped configuration while the other two reinforcement members (3610) have a generally "L" shaped configuration. These shapes are configured to enable each reinforcement member (3610) to receive several staples (77) from different rows and columns of staple cartridge (70). By spanning across discrete sets of staples (77) from different rows and columns of staple cartridge (70), reinforcement members (3610) may provide greater reinforcement than what might otherwise be provided if reinforcement members (3610) spanned the entire array of staples (77) or just individual staples (77). Other suitable shapes and arrangements for reinforcement members (3610) will be apparent to those of ordinary skill in the art in view of the teachings herein. It should also be understood that reinforcement members (3610) may be integrated into buttress body (3602) in any suitable fashion, including but not limited to providing reinforcement members (3610) between apposed layers of buttress body (3602) or forming buttress body (3602) around reinforcement members (3610).

5. Exemplary Alternative Retainer

Figure 58:
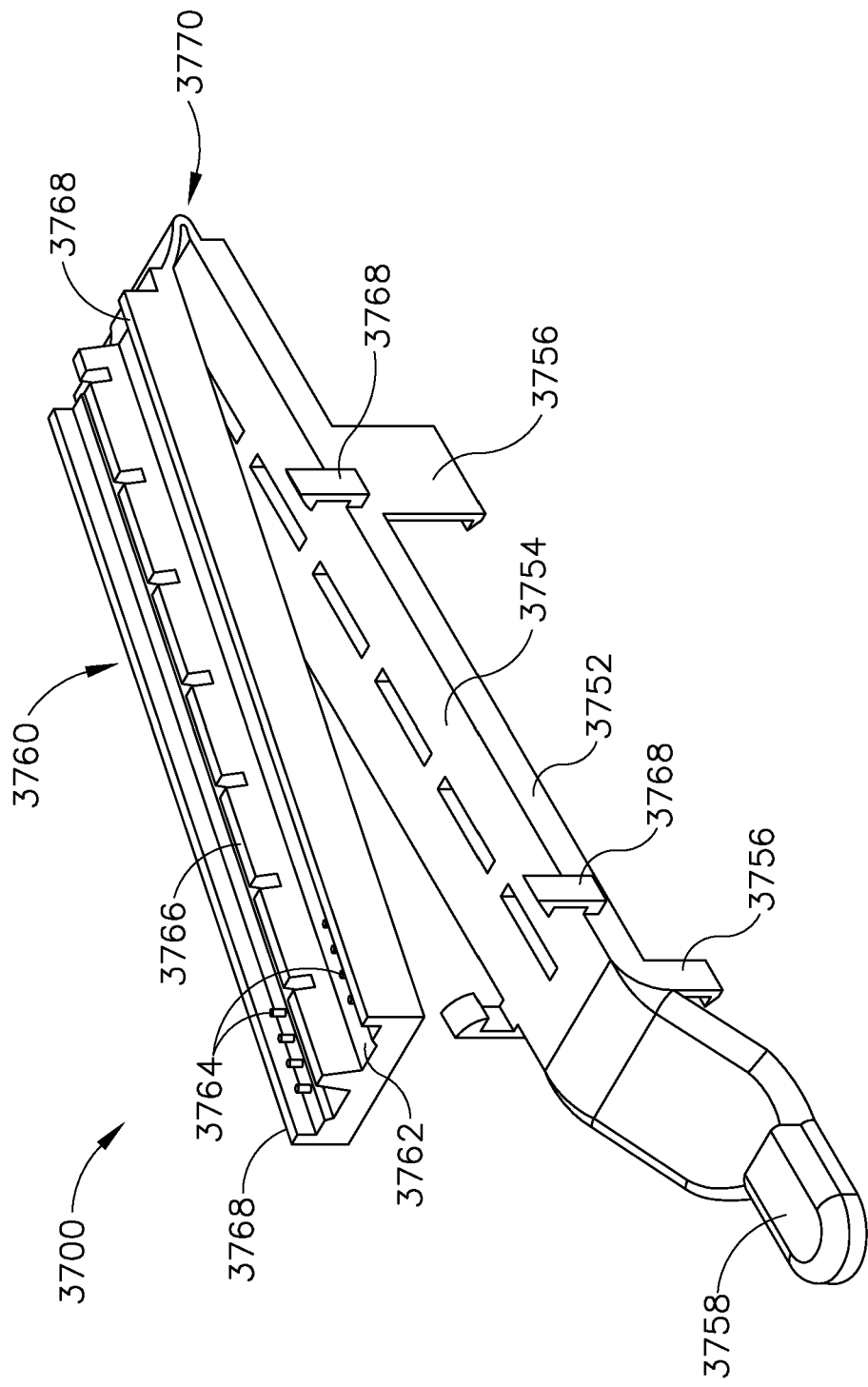
FIG. 58 depicts a perspective view of an exemplary alternative retainer.

FIG. 58 shows an exemplary alternative retainer (3700) that may be used with any of the various buttress assemblies described herein. Retainer (3700) of this example comprises a base member (3752) having an upper surface (3754), a plurality of latches (3756), and a distally projecting tongue (3758) that is configured to facilitate grasping and manipulation of retainer (3750). Retainer (3700) also includes an upper member (3760) that is secured to base member (3752) by a living hinge (3770). Upper member (3760) has an upper surface (3762) that is configured to engage buttress body (3702). Upper member (3760) includes a plurality of projections (3764) extending upwardly from upper surface (3762), and central rib (3766) extending upwardly and longitudinally along the laterally central region of upper surface (3762), and a pair of outer ribs (3768) extending upwardly and longitudinally along the outer edges of upper surface (3762). While projections (3764) are shown as spanning along only a portion of the length of upper surface (3762), it should be understood that projections (3764) may span along the entire length of upper surface. It should also be understood that projections (3764) may span along three rows on each side of central rib (3766), corresponding to three rows of staple forming pockets (64) on underside (65) of anvil (60).

It should be understood that retainer (3700) may be removably secured to end effector (40) in a manner similar to retainer (300) described above, with latches (3756) releasably engaging lower jaw (50). At such a stage, upper member (3760) is spaced away from upper surface (3754) of base member (3752) due to a resilient bias imposed by living hinge (3770). The resilient bias provided by living hinge (3770) may ensure that upper adhesive layer (104) of a buttress assembly (100) that is laid over upper surface (3762) will contact the appropriate region of underside (65) of anvil (60) before anvil (60) reaches a fully closed position. The resilient bias provided by living hinge (3770) may also provide and maintain a minimum consistent pressure during the closure of anvil (60) to enhance the attachment of upper adhesive layer (104) to underside (65) of anvil (60).

As anvil (60) is driven further toward the closed position, anvil (60) bears down on upper adhesive layer (104) and upper member (3760), thereby causing upper member (3760) to pivot toward base member (3752). Adhesive layer (104) is compressed between underside (65) of anvil (60) and projections (3764). Projections (3764) provide focused pressure to regions of buttress assembly (100) at regions corresponding to staple forming pockets (64) (and/or into other surface features of underside (65)), thereby further promoting adhesion between adhesive layer (104) and underside (65). Ribs (3766, 3768) may ensure proper lateral alignment of retainer (3700) and buttress assembly (100) with anvil (60) during the closure of anvil (60). Ribs (3766, 3768) may also prevent adhesive material from entering channel (62) or escaping from sides of anvil (60) during closure of anvil (60). When anvil (60) reaches the closed position, latches (3768) of retainer (3700) may secure upper member (3760) into apposition with base member (3752), facilitating removal of retainer (3750) from end effector (40). Buttress assembly (100) may then be left adhered to underside (65) of anvil (60), such that end effector (40) is then ready for use.

While retainer (3700) is described as being used in combination with buttress assembly (100), it should be understood that retainer (3700) may be used in combination with any other buttress assembly referred to herein.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013 the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of applying a buttress assembly to a surgical stapler end effector having an anvil and a staple cartridge that houses a plurality of staples, wherein the buttress assembly includes a buttress body comprising a mesh of polyglactin 910, an adhesive material disposed non-uniformly over and coupled with the buttress body independently of the surgical stapler end effector, and a barrier layer interposed between the buttress body and the adhesive material, wherein the barrier layer is configured to at least partially inhibit permeation of the adhesive material into the buttress body, wherein the adhesive material comprises a blend of multiple polymers and is flowable and absorbable in the absence of an external heat source, the method comprising:

(a) positioning the buttress assembly between the anvil and the staple cartridge while the anvil is in an open position relative to staple cartridge, wherein the adhesive material faces one of an underside of the anvil or a deck of the staple cartridge;

(b) moving the anvil toward the staple cartridge to a closed position and thereby causing the adhesive material to adhere to the one of the underside of the anvil or the deck of the staple cartridge;

(c) moving the anvil away from the staple cartridge back to the open position while the buttress assembly remains secured to the one of the underside of the anvil or the deck of the staple cartridge via the adhesive material; and (d) driving the staples through the buttress assembly and forming the staples with the anvil such that at least some of the staples engage the mesh of the buttress body.

2. The method of claim 1, wherein the adhesive material is configured to plastically deform in response to an externally applied load.

3. The method of claim 1, wherein the adhesive material comprises a blend of multiple homopolymers or multiple copolymers.

4. The method of claim 1, wherein the adhesive material comprises polyethylene glycol (PEG).

5. The method of claim 1, wherein the adhesive material comprises a blend of polypropylene glycol and polyethylene glycol (PEG).

6. The method of claim 1, wherein the adhesive material comprises a copolymer of caprolactone and glycolide (PCL/PGA).

7. The method of claim 1, wherein the adhesive material comprises a copolymer of lactide and caprolactone (PLA/PCL).

8. The method of claim 1, wherein the adhesive material comprises a copolymer of trimethylene carbonate and lactide (TMC/PLA) or a copolymer of trimethylene carbonate and caprolactone (TMC/PCL).

9. The method of claim 1, wherein the barrier layer comprises polydioxanone.

10. The method of claim 1, wherein the buttress assembly is provided on a retainer, wherein positioning the buttress assembly between the anvil and the staple cartridge comprises positioning the retainer between the anvil and the staple cartridge, wherein moving the anvil to the closed position comprises compressing the buttress assembly against the retainer.

11. The method of claim 1, further comprising removing a film from the buttress assembly to expose the adhesive material before moving the anvil toward the staple cartridge.

12. The method of claim 1, wherein the adhesive comprises a plurality of discretely formed adhesive regions arranged non-uniformly over the buttress body.

13. The method of claim 1, further comprising heating at least a portion of the buttress assembly before causing the adhesive material to adhere to the one of the underside of the anvil or the deck of the staple cartridge.

14. A method of applying a buttress assembly to a surgical stapler end effector having an anvil and a staple cartridge that houses a plurality of staples, wherein the buttress assembly includes a buttress body comprising a mesh of polyglactin 910 and an adhesive material arranged in a plurality of discretely formed adhesive regions disposed non-uniformly over and coupled with the buttress body independently of the surgical stapler end effector, wherein the adhesive material comprises a blend of multiple polymers and is flowable and absorbable in the absence of an external heat source, wherein at least a portion of the buttress assembly comprises polydioxanone, the method comprising:

(a) positioning the buttress assembly between the anvil and the staple cartridge while the anvil is in an open position relative to staple cartridge, wherein the adhesive material faces one of an underside of the anvil or a deck of the staple cartridge;

(b) moving the anvil toward the staple cartridge to a closed position and thereby causing the adhesive material to adhere to the one of the underside of the anvil or the deck of the staple cartridge;

(c) moving the anvil away from the staple cartridge back to the open position while the buttress assembly remains secured to the one of the underside of the anvil or the deck of the staple cartridge via the adhesive material; and (d) driving the staples through the buttress assembly and forming the staples with the anvil such that at least some of the staples engage the mesh of the buttress body.

15. The method of claim 14, wherein the polydioxanone comprises a layer of polydioxanone in contact with the buttress body.

16. The method of claim 15, wherein the layer of polydioxanone is interposed between the buttress body and the adhesive material.

17. The method of claim 14, further comprising heating at least a portion of the buttress assembly before causing the adhesive material to adhere to the one of the underside of the anvil or the deck of the staple cartridge.

18. A method of applying a buttress assembly to a surgical stapler end effector having an anvil and a staple cartridge that houses a plurality of staples, wherein the buttress assembly includes a buttress body comprising a mesh and an adhesive layer disposed over and coupled with the buttress body independently of the surgical stapler end effector, wherein the adhesive layer includes a plurality of discretely formed adhesive regions arranged non-uniformly over the buttress body, wherein at least some of the adhesive regions have a varying thickness and are flowable and absorbable in the absence of an external heat source, the method comprising:

(a) positioning the buttress assembly between the anvil and the staple cartridge while the anvil is in an open position relative to staple cartridge, wherein the adhesive layer faces one of an underside of the anvil or a deck of the staple cartridge;

(b) moving the anvil toward the staple cartridge to a closed position and thereby compressing the adhesive regions with a non-homogeneous pressure distribution and causing the adhesive regions to adhere to the one of the underside of the anvil or the deck of the staple cartridge;

(c) moving the anvil away from the staple cartridge back to the open position while the buttress assembly remains secured to the one of the underside of the anvil or the deck of the staple cartridge via the adhesive layer; and (d) driving the staples through the buttress assembly and forming the staples with the anvil such that at least some of the staples engage the mesh of the buttress body.

19. The method of claim 18, wherein the buttress assembly further comprises a barrier layer interposed between the buttress body and the adhesive layer, wherein the barrier layer is configured to at least partially inhibit permeation of the adhesive regions into the buttress body.

* * * * *